United States Patent
Takahashi et al.

(10) Patent No.: US 9,662,114 B2
(45) Date of Patent: May 30, 2017

(54) METHOD OF FORMING THROUGH HOLE

(71) Applicant: OLYMPUS CORPORATION, Tokyo (JP)

(72) Inventors: Shinji Takahashi, Tokyo (JP); Kunihide Kaji, Tokyo (JP); Masatoshi Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 780 days.

(21) Appl. No.: 13/968,034

(22) Filed: Aug. 15, 2013

(65) Prior Publication Data
US 2014/0058419 A1     Feb. 27, 2014

Related U.S. Application Data

(63) Continuation of application No. 12/171,816, filed on Jul. 11, 2008, now abandoned, and a continuation of
(Continued)

(51) Int. Cl.
*A61B 17/11* (2006.01)
*A61B 17/064* (2006.01)
(Continued)

(52) U.S. Cl.
CPC ........ *A61B 17/1114* (2013.01); *A61B 17/064* (2013.01); *A61B 17/32002* (2013.01);
(Continued)

(58) Field of Classification Search
CPC .... A61B 2017/0649; A61B 2017/1103; A61B 2017/1107; A61B 2017/1117;
(Continued)

(56) References Cited

U.S. PATENT DOCUMENTS

| 5,536,274 A | 7/1996 | Neuss |
| 5,540,701 A * | 7/1996 | Sharkey ................. A61B 17/11 606/153 |

(Continued)

FOREIGN PATENT DOCUMENTS

| JP | 05070549 U | 9/1993 |
| JP | 07308331 A | 11/1995 |

(Continued)

OTHER PUBLICATIONS

Chinese Office Action dated Feb. 11, 2014 in corresponding Chinese Patent Application No. 201210193072.3.
(Continued)

*Primary Examiner* — Dianne Dornbusch
(74) *Attorney, Agent, or Firm* — Scully, Scott, Murphy & Presser, P.C.

(57) ABSTRACT

This tissue fastening apparatus is a tissue fastener for clamping first biological tissue and second biological tissue so as to be in close contact with each other, including: a first tissue fixation portion, made of an elastic wire wound in a coil, that is locked on the first biological tissue; and a second tissue fixation portion, made of an elastic wire wound in a coil, that is locked on the second biological tissue, the second tissue fixation portion continuing into the first tissue fixation portion, in which when falling off first and second biological tissue necrotized by being clamped between the first tissue fixation portion and the second tissue fixation portion, the tissue fastener moves only from the second tissue fixation portion to the first tissue fixation portion side and falls off.

15 Claims, 75 Drawing Sheets

Related U.S. Application Data application No. 12/430,442, filed on Apr. 27, 2009, now abandoned.

(51) Int. Cl.
*A61B 17/32* (2006.01)
*A61B 17/068* (2006.01)
*A61B 17/00* (2006.01)
*A61B 17/3207* (2006.01)

(52) U.S. Cl.
CPC ... *A61B 17/068* (2013.01); *A61B 2017/00685* (2013.01); *A61B 2017/00867* (2013.01); *A61B 2017/0649* (2013.01); *A61B 2017/320032* (2013.01); *A61B 2017/320775* (2013.01)

(58) Field of Classification Search
CPC .... A61B 2017/1132; A61B 2017/1135; A61B 2017/1139; A61B 2017/1142; A61B 17/11; A61B 17/1114; A61B 17/115
See application file for complete search history.

(56) References Cited

U.S. PATENT DOCUMENTS

| | | | |
|---|---|---|---|
| 5,582,616 | A | 12/1996 | Bolduc |
| 5,830,221 | A | 11/1998 | Stein et al. |
| 6,113,611 | A | 9/2000 | Allen et al. |
| 6,117,157 | A | 9/2000 | Tekulve |
| 6,551,340 | B1 | 4/2003 | Konya et al. |
| 6,635,066 | B2 | 10/2003 | Tanner et al. |
| 6,663,633 | B1 | 12/2003 | Pierson, III |
| 6,790,218 | B2 | 9/2004 | Jayaraman |
| 6,837,893 | B2 | 1/2005 | Miller |
| 6,986,784 | B1 | 1/2006 | Weiser et al. |
| 7,131,979 | B2 | 11/2006 | DiCarlo et al. |
| 7,637,946 | B2 | 12/2009 | Solem et al. |
| 7,722,636 | B2 | 5/2010 | Farnan |
| 8,932,305 | B2 * | 1/2015 | Takahashi ............ A61B 17/064 606/139 |
| 2002/0013605 | A1 | 1/2002 | Bolduc et al. |
| 2003/0014127 | A1 | 1/2003 | Talja et al. |
| 2003/0225420 | A1 | 12/2003 | Wardle |
| 2004/0073237 | A1 | 4/2004 | Leinsing |
| 2005/0143763 | A1 * | 6/2005 | Ortiz .................. A61B 17/1114 606/153 |
| 2005/0267495 | A1 | 12/2005 | Ginn et al. |
| 2006/0212047 | A1 | 9/2006 | Abbott et al. |
| 2007/0225737 | A1 | 9/2007 | Messerly et al. |
| 2007/0270886 | A1 | 11/2007 | McGuckin, Jr. et al. |
| 2008/0004640 | A1 | 1/2008 | Ellingwood |
| 2008/0015633 | A1 | 1/2008 | Abbott et al. |
| 2008/0051626 | A1 * | 2/2008 | Sato .................. A61B 1/00082 600/101 |
| 2008/0208214 | A1 * | 8/2008 | Sato ..................... A61B 17/115 606/139 |
| 2009/0069822 | A1 * | 3/2009 | Takahashi ............ A61B 17/064 606/139 |
| 2010/0010508 | A1 | 1/2010 | Takahashi et al. |
| 2010/0010520 | A1 | 1/2010 | Takahashi et al. |

FOREIGN PATENT DOCUMENTS

| | | |
|---|---|---|
| JP | 2000514336 A | 10/2000 |
| JP | 2003517869 A | 6/2003 |
| JP | 2005193044 A | 7/2005 |
| JP | 2009508536 A | 3/2009 |
| WO | 9727898 A1 | 8/1997 |
| WO | 9732527 A1 | 9/1997 |
| WO | 9802100 A1 | 1/1998 |
| WO | 0145571 A1 | 6/2001 |
| WO | 0219923 A1 | 3/2002 |
| WO | 03105703 A2 | 12/2003 |
| WO | 2004026113 A2 | 4/2004 |
| WO | 2007005996 A2 | 1/2007 |

OTHER PUBLICATIONS

Japanese Office Action dated Jan. 28, 2014 in corresponding Japanese Patent Application No. 2012-113240.
Notice of Allowance dated Sep. 24, 2014 from U.S. Appl. No. 13/422,472.
Partial European Search Report dated May 3, 2010 in corresponding European Patent Application No. 09009029.1.
Partial European Search Report dated May 31, 2010 in corresponding European Patent Application No. 09008552.3.
U.S. Office Action dated Mar. 11, 2011 in related U.S. Appl. No. 12/171,816.
U.S. Office Action dated May 20, 2011 in related U.S. Appl. No. 12/430,442.
U.S. Office Action dated Jun. 16, 2011 in related U.S. Appl. No. 12/171,816.
U.S. Office Action dated Jul. 12, 2011 in related U.S. Appl. No. 12/171,817.
U.S. Office Action dated Jul. 27, 2011 in related U.S. Appl. No. 12/430,484.
U.S. Office Action dated Jul. 27, 2011 in related U.S. Appl. No. 12/430,442.
Partial European Search Report dated Oct. 25, 2011 in corresponding European Patent Application No. 11003621.7.
U.S. Office Action dated Nov. 22, 2011 in related U.S. Appl. No. 12/171,816.
U.S. Office Action dated Dec. 15, 2011 in related U.S. Appl. No. 12/430,442.
Japanese Office Action dated May 8, 2012 in corresponding Japanese Patent Application No. 2009-146917.
U.S. Office Action dated Jun. 5, 2012 in related U.S. Appl. No. 12/430,442.
U.S. Office Action dated Aug. 6, 2012 in related U.S. Appl. No. 12/171,816.
U.S. Office Action dated Oct. 26, 2012 in related U.S. Appl. No. 12/430,442.
U.S. Office Action dated Feb. 19, 2013 in related U.S. Appl. No. 12/171,816.
U.S. Office Action dated Apr. 25, 2013 in related U.S. Appl. No. 12/430,442.
U.S. Office Action dated Jun. 28, 2013 in related U.S. Appl. No. 12/171,816.

\* cited by examiner

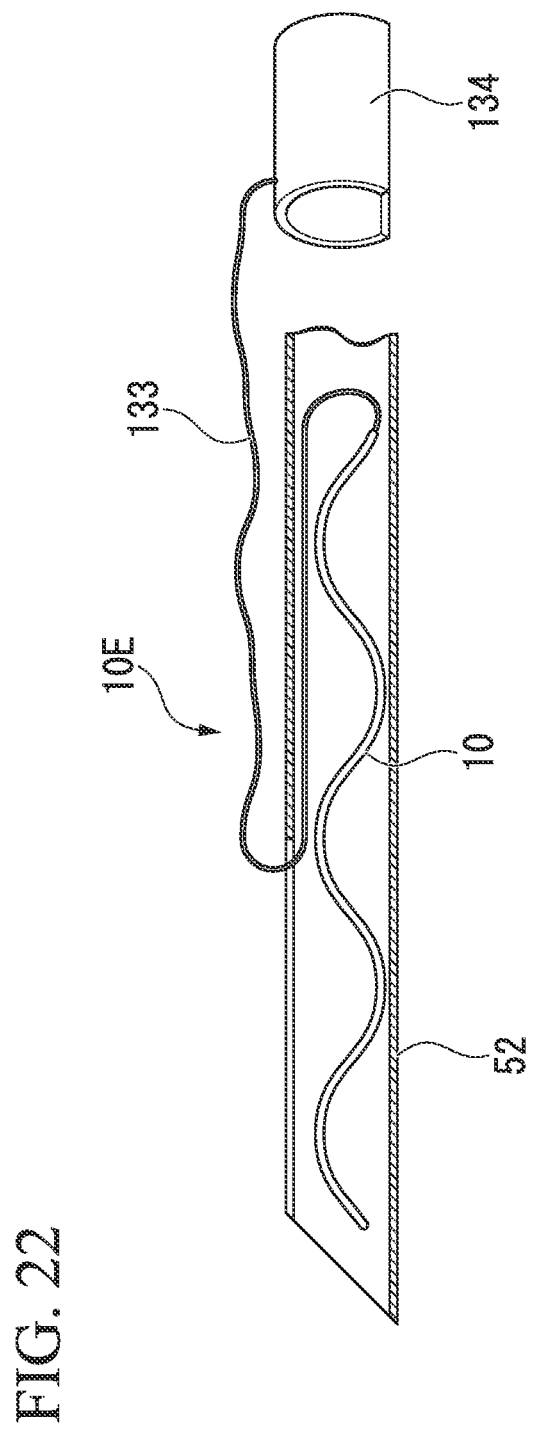

FIG. 71
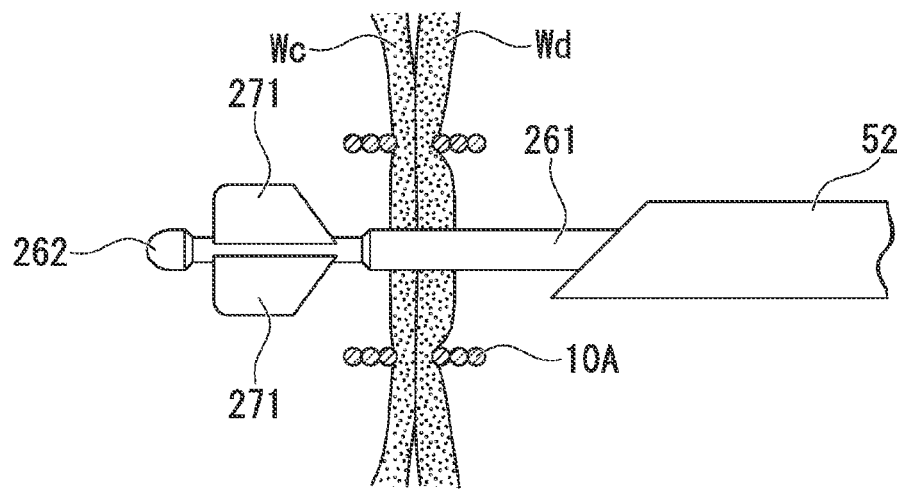
FIG. 72
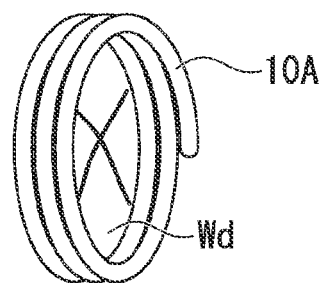
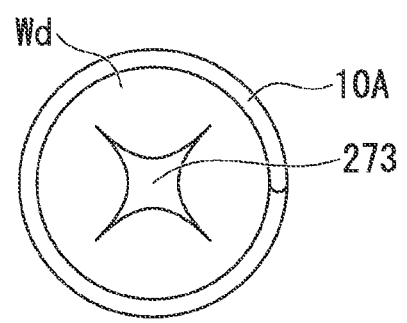

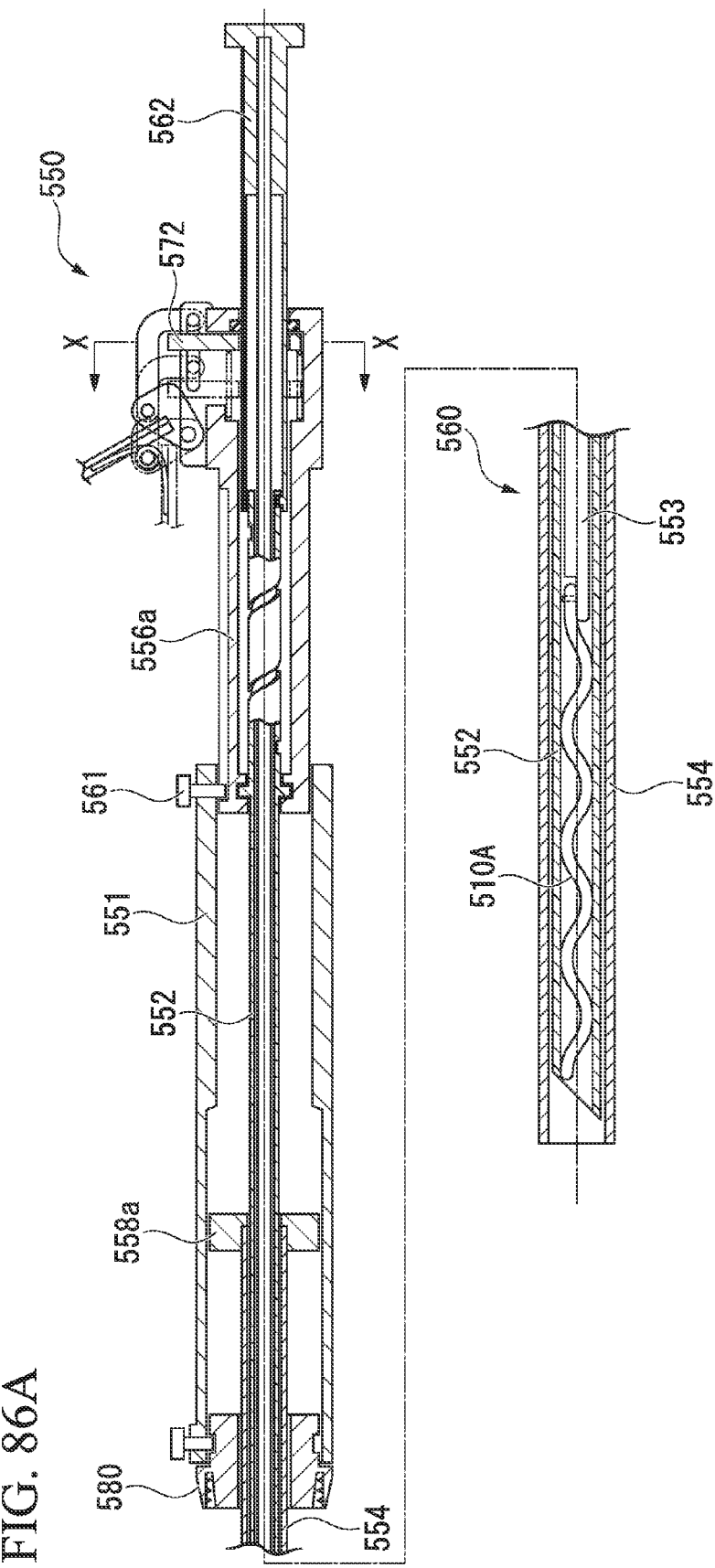
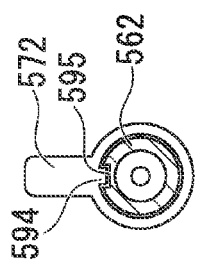
FIG. 86A
FIG. 86B

METHOD OF FORMING THROUGH HOLE

The present application is a continuation based on U.S. patent application Ser. No. 12/171,816 "Tissue Fastener" filed on Jul. 11, 2008 and U.S. patent application Ser. No. 12/430,442 "Tissue Fastening Instrument" filed on Apr. 27, 2009. The contents of both the United States Patent Applications are incorporated herein by reference.

BACKGROUND OF THE INVENTION

Field of the Invention

The present invention relates to a method of forming a through hole for fastening tissue through a natural orifice.

The present invention relates to a method of forming a through hole for fastening tissue through a natural orifice.

Description of Related Art

As a technique for performing a treatment on a human organ or the like, laparoscopic surgery is known in which a treatment device is percutaneously inserted. This requires less invasion than the case of incising an abdominal region. Therefore, an early recovery is expectable.

A treatment device for use in laparoscopic surgery has a hard shaft which is percutaneously inserted into a body. At a tip of the shaft, forceps or the like are provided. For example, Japanese Unexamined Patent Publication, First Publication No 2005-193044 discloses a treatment device for use in application for joining hollow organs. In this intraluminal anastomosis apparatus, a grip device that is freely opened/closed is attached to the tip of the shaft. Into the shaft, a fastener is inserted. The fastener is capable of being pushed out from the tip of the shaft with a plunger mechanism on the hand side. The fastener is manufactured by heat-treating a shape-memory alloy in a flat coil shape. It is inserted into the shaft in an extended state. In application, the fastener is pushed out with the plunger mechanism and piercingly inserted into a body. The fastener is heated by body temperature and is restored to its original coil shape. Hollow organs are joined by the restored fastener.

Another example of providing a clamping apparatus is disclosed in PCT International Patent Publication No. WO 2002/019923 pamphlet. Here, a fastener is pushed out from a needle and is provided to tissue. Therefore, stoppers are provided for controlling the amount of depth that the needle is piercingly inserted into tissue and/or the amount of the fastener to be supplied to the tissue. When a treatment is performed, a device containing the fastener and the needle is placed against the tissue. When the needle is moved forward and piercingly inserted into the tissue, the position of the fastener is fixed with the stoppers. After this, the needle is withdrawn from the tissue. The fastener does not move due to the presence of the stoppers. Therefore, a tip portion of the fastener is left inside the tissue. When the device is detached from the tissue, the remaining part of the fastener is left outside the tissue. When the fastener assumes its original coil shape, the tissue is clamped.

SUMMARY OF THE INVENTION

According to a first aspect of the present invention, a method of forming a through hole that communicates between a first hollow organ tissue and a second hollow organ tissue adjacent to the first hollow organ tissue, includes the steps of: inserting a needle tube which holds a tissue fastening instrument into the first hollow organ tissue and the second hollow organ tissue in an extended state, wherein the tissue fastening instrument includes a first tissue fixing portion and a second tissue fixing portion which are formed by being wound in a coil shape, and a peripheral spring portion that is wound in a shape of a spiral around periphery of the first tissue fixing portion and the second tissue fixing portion, that extends in an outer diameter direction, and that connects to the second tissue fixing portion; engaging the first tissue fixing portion, which is restored to a coil shape, with the first hollow organ tissue by allowing the tissue fastening instrument to extrude from the needle tube; pulling out the needle tube from the first hollow organ tissue and the second hollow organ tissue; holding and fastening the first hollow organ tissue and the second hollow organ tissue between the first tissue fixing portion and the second tissue fixing portion by using the second tissue fixing portion extruded from the needle tube and restored to a coil shape, after the needle tube is pulled out from the first hollow organ tissue and the second hollow organ tissue; and pressing an outside portion of the first hollow organ tissue and the second hollow organ tissue which is surrounded by the first tissue fixing portion and the second tissue fixing portion as seen from an axis direction of the tissue fastening instrument by using the peripheral spring portion extruded from the needle tube and restored to a spiral shape, after a first tissue fixing portion and a second tissue fixing portion are extruded from the needle tube.

According to a second aspect of the present invention, in the first aspect, the method further includes forming the through hole in the first hollow organ tissue and the second hollow organ tissue by causing necrosis of the first hollow organ tissue and the second hollow organ tissue which are held and fastened between the first tissue fixing portion and the second tissue fixing portion using the first tissue fixing portion and the second tissue fixing portion.

According to a third aspect of the present invention, in the second aspect, the first hollow organ tissue may be a wall of a common bile duct, and the second hollow organ tissue may be an intestinal wall of a duodenum.

BRIEF DESCRIPTION OF THE DRAWINGS

FIG. 15A to FIG. 42 show other forms of a tissue fastener.

FIG. 64 to FIG. 75 show forms of drainages.

FIG. 86A is a drawing that shows the operation during use of the same tissue fastening instrument and the same applicator.

FIG. 86B is a cross-sectional view along line X-X of FIG. 83A.

DETAILED DESCRIPTION OF THE INVENTION

Figure 1:
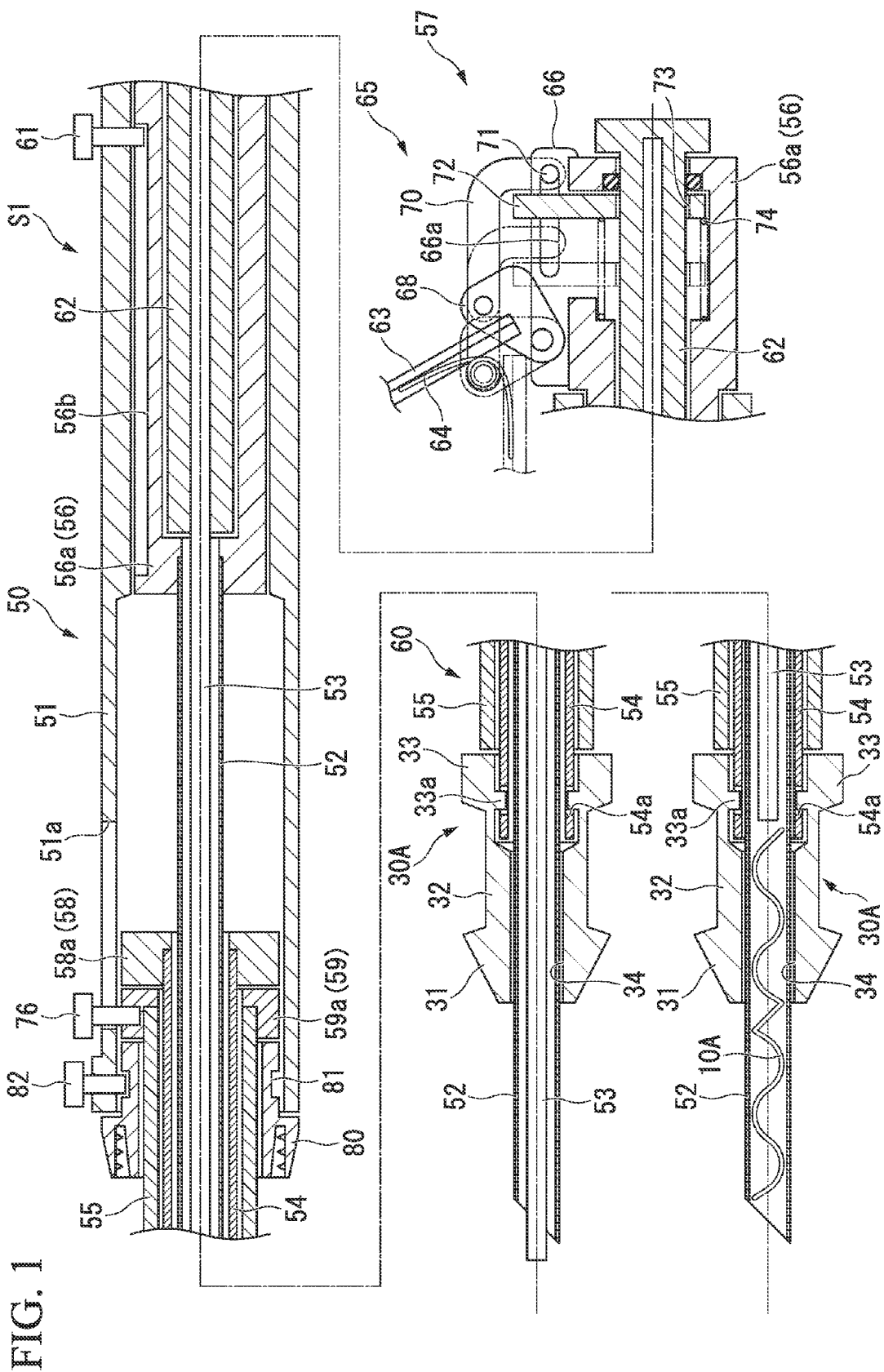
FIG. 1 shows a first embodiment of a tissue fastening apparatus of the present invention. It is a cross-sectional view showing internal structures of a tissue fastener, a stent, and an applicator that constitute the apparatus.

A first embodiment of the present invention will be described. A tissue fastening apparatus 51 of the present embodiment is, as shown in FIG. 1, an apparatus for performing a treatment of fixing second biological tissue onto first biological tissue and communicating both organs. This apparatus includes: a tissue fastener 10A; a stent 30A; and an applicator 50. Note that the first biological tissue and the second biological tissue do not necessarily refer to different organs. For example, a given region of a given organ may be taken as first biological tissue and another region of the same organ may be taken as second biological tissue, and these two regions may be fixed. In the present embodiment, a treatment of fixing a common bile duct as the second biological tissue onto a duodenum as the first biological tissue and communicating both organs will be described.

Figure 2:
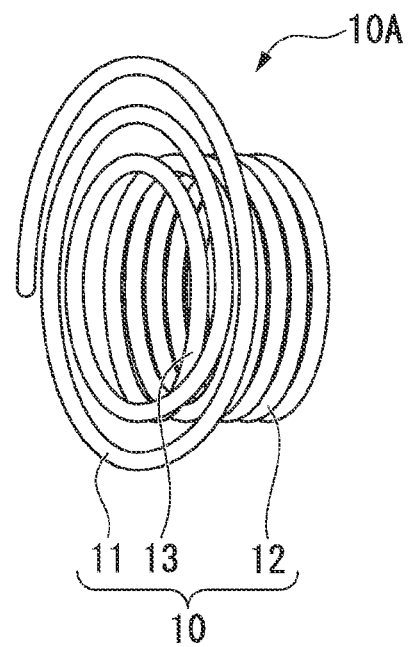
FIG. 2 is a perspective view showing the tissue fastener that constitutes the above tissue fastening apparatus.

The tissue fastener 10A is a device for clamping the duodenum and the common bile duct. It includes: a first tissue fixation portion 11 that is locked on the duodenum; and a second tissue fixation portion 12 that is locked on the common bile duct adjacent to the duodenum, as shown in FIG. 2. The tissue fastener 10A is a device for clamping the duodenum and the common bile duct. It includes: a first tissue fixation portion 11 that is locked on the duodenum; and a second tissue fixation portion 12 that is locked on the common bile duct adjacent to the duodenum, as shown in FIG. 2. Furthermore, the tissue fastener 10A includes a linking portion 13 between the first tissue fixation portion 11 and the second tissue fixation portion 12 for linking the two.

The tissue fastener 10A is made of a string of highly elastic metal wire 10 in which all the portions thereof that is, the first tissue fixation portion 11, the second tissue fixation portion 12, and the linking portion 13 are wound in a coil. Note that in this specification, the phrase "wound in a coil" includes all the cases of "wound in a cylinder," "wound in a frustum of a cone," and "wound in a vortex." In the first tissue fixation portion 11, the highly elastic metal wire 10 is wound in a vortex. In the second tissue fixation portion 12, the highly elastic metal wire 10 is wound in a cylinder. An inner diameter of the first tissue fixation portion 11 is equal to that of the second tissue fixation portion 12. An outer diameter of the first tissue fixation portion 11 is larger than that of the second tissue fixation portion.

In a part of the wire positioned between the first tissue fixation portion 11 and the linking portion 13, a bent portion 14 is formed. Similarly, in a part of the wire positioned between the linking portion 13 and the second tissue fixation portion 12, a bent portion 15 is formed. The first tissue fixation portion 11 and the second tissue fixation portion 12 form coils with the same diameter. With the provision of the linking portion 13, a gap G is formed between the two.

Figure 3:
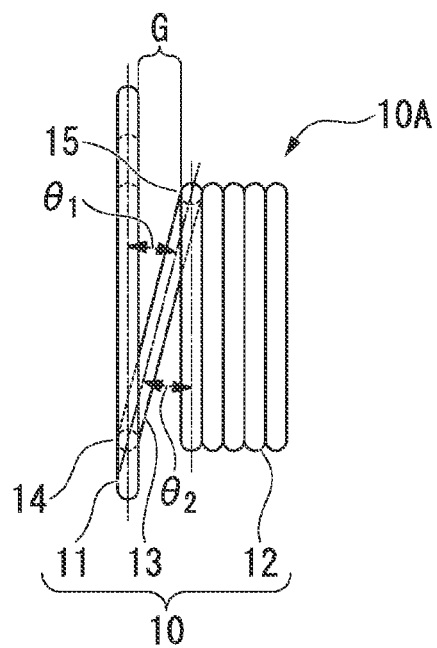
FIG. 3 is a plan view of the above tissue fastener, seen in a direction different from that of FIG. 2.

The central axis of the coil shape of the first tissue fixation portion 11 coincides with that of the coil shape of the second tissue fixation portion 12. As shown in FIG. 3, a wire portion forming the linking portion 13 has, at the bent portion 14, an angle $\theta 1$ with respect to a wire portion forming the coil of the first tissue fixation portion 11. It also has, at the bent portion 15, an angle $\theta 2$ with respect to a wire portion forming the coil of the second tissue fixation portion 12. The angle $\theta 1$ of the bent portion 14 is substantially the same as the angle $\theta 2$ of the bent portion 15.

After the tissue fastener 10A is extended, one end thereof is inserted into biological tissue. Then, the other tissue fixation portion, for example the second tissue fixation portion 12, is penetrated through an intestinal wall of the duodenum and a duct wall of the common bile duct in this order. The second tissue fixation portion 12, which has been penetrated through the intestinal wall of the duodenum and the duct wall of the common bile duct, has its restraint released in an inside of the common bile duct to assume its original coil shape (cylindrical shape), and is locked on the common bile duct. On the other hand, the first tissue fixation portion 11 has its restraint released in an inside of the duodenum to assume its original coil shape (vortex shape), and is locked on the duodenum. With the first tissue fixation portion 11 locked on the duodenum and the second tissue fixation portion 12 locked on the common bile duct, the intestinal wall of the duodenum and the duct wall of the common bile duct are clamped so as to be pressed against each other. The linking portion 13 is placed in the interiors of the clamped walls of both organs.

The stent 30A is, as shown in FIG. 1, a device for communicating the intestinal wall of the duodenum with the duct wall of the common bile duct that are clamped by the tissue fastener 10A. It includes: an extension portion 31; a placement portion 32; a slip-off prevention portion 33; and a through-hole 34, The extension portion 31 is of a cone shape whose diameter is wider from its front end to its rear end. The placement portion 32 is of a cylindrical shape, and is disposed at the rear of the extension portion 31. The placement portion 32 has a constant outer diameter, which is smaller than the maximum outer diameter of the extension portion 31. The slip-off prevention portion 33 is of a cylindrical shape, and is disposed at the rear of the placement portion 32. The slip-off prevention portion 33 has an outer diameter larger than that of the placement portion 32. The through-hole 34 penetrates through the extension portion 31 the placement portion 32, and the slip-off prevention portion 33 in the longitudinal direction of the stent 30A.

In the inside surface of the slip-off prevention portion 33, protrusions 33a that are formed in the radial directions of the stent 30A are provided. The protrusions 33a constitute a part of an attachment portion for detachably attaching the stent 30A onto a later-described sheath 54 of the applicator 50.

As a material for the stent 30A, any of stainless steel (SUS), titanium (Ti), bioabsorbable magnesium, polyethylene (PE), polyether ether ketone (PEEK), polysulfone, liquid crystal polymer, polylactic acid, polyglycolic acid, polydioxanone, polyhydroxyalkanoate, and caprolactone, or a polymer of these can be adopted. These are excellent in biocompatibility. Therefore, they will not impose an undue burden on a living body after placement of the stent 30A in the living body. Especially polylactic acid, polyglycolic acid, polydioxanone, polyhydroxyalkanoate, and caprolactone are advantageous because they are absorbed in a living body while they are placed in the living body for a long period of time, and finally no foreign matter is left in the living body.

The applicator 50 is a device for performing a treatment of placing the tissue fastener 10A and the stent 30A within a body. It includes: an applicator main unit 51; a piercing device 52; a stylet (a fastener pusher) 53; a sheath 54; and a stent pusher 55, as shown in FIG. 1. The applicator main unit 51 is of a cylindrical shape. The piercing device 52 is of a needle tube shape. It is used with the tissue fastener 10A being inserted thereinto. Note that electrodes may be provided at a tip of the piercing device 52 and that the piercing device 52 may be piercingly inserted into the intestinal wall of the duodenum and the duct wall of the common bile duct while burning the biological tissue. In this case, the tip of the piercing device 52 is not required to be formed sharp.

The stylet 53 is of a shaft shape. It is movably inserted inside the piercing device 52, and pushes out the tissue fastener 10A inserted into the piercing device 52 from the tip of the piercing device 52.

The sheath 54 has the piercing device 52 movably inserted into the inside thereof, and moves the stent 30A that is detachably attached onto the tip thereof, relatively to the piercing device 52.

The stent pusher 55 is of a sheath-like shape. It detaches the stent 30A, into the inside of which the sheath 54 is movably inserted and which is attached onto the front end thereof, from the sheath 54.

In the applicator main unit 51, a piercing device operation portion 56, a stylet operation portion (a fastener pusher operation portion) 57, a sheath operation portion 58, and a stent pusher operation portion 59 are provided. All of the piercing device 52, the stylet 53, the sheath 54, and the stent pusher 55 have flexibility, and are arranged coaxially. These constitute an insertion portion 60 that is inserted through a work channel of an endoscope. Obviously, the insertion portion 60 is longer than the work channel of the endoscope.

A tip face of the piercing device 52 is formed diagonally with respect to the longitudinal direction of the piercing device 52. As a result, a tip of the piercing device 52 is finished sharp. A base end of the piercing device 52 is connected with the piercing device operation portion 56, which is provided to a rear portion of the applicator main unit 51.

A tip of the stylet 53 is formed into a shape not sharp but smooth. A base end of the stylet 53 is connected with the stylet operation portion 57, which is provided in an interior of the piercing device operation portion 56.

A tip face of the sheath 54 is formed flat so as to orthogonally cross the longitudinal direction of the sheath 54. In the tip of the sheath 54, small holes 54a are provided and the number of which is the same as or more than that of the protrusions 33a of the stent 30A. The small holes 54a are arranged in a circumferential direction of the sheath 54. They penetrate through a duct wall of the sheath 54. The small holes 54a constitute a part of the attachment portion for detachably attaching the stent 30A on the sheath 54. When the tip of the sheath 54 is inserted into the through-hole 34 of the stent 30A from the rear end, the protrusions 33a are engaged in the small holes 54a. As a result, the stent 30A is attached onto the tip of the sheath 54. Since the sheath 54 has flexibility, when the sheath 54 is pulled in a rear direction with the stent 30A retained in position, the sheath 54 is elastically deformed and is detached from the small holes 54a. As a result, the stent 30A is disengaged from the tip of the sheath 54. Note that if the stent 30A is made of an elastic material, both of the sheath 54 and the protrusions of the stent 30A may be elastically deformed, to thereby cause the stent 30A to be disengaged from the tip of the sheath 54.

Incidentally, the small holes 54a need not penetrate through the wall portion of the sheath 54. They may be recesses formed in an outside surface of the sheath 54. Furthermore, small holes may be formed in the stent 30A, and also protrusions may be formed in the sheath 54, and then both may be engaged.

A base end of the sheath 54 is connected with a sheath operation portion 58 provided in a front portion of the applicator main unit 51.

A tip face of the stent pusher 55 is formed flat so as to orthogonally cross the longitudinal direction of the stent pusher 55. A base end of the stent pusher 55 is connected with a stent pusher operation portion 59 provided in the front portion of the applicator main unit 51.

The piercing device operation portion 56 includes a cylindrical first shaft 56a that is inserted into the inside of the applicator main unit 51 from a rear end thereof. The first shaft 56a has an outer diameter slightly smaller than an inner diameter of the rear portion of the applicator main unit 51. Therefore, the first shaft 56a is slidable with respect to an inner surface of the rear portion of the applicator main unit 51. The base end of the piercing device 52 is fixedly attached to a tip face of the first shaft 56a, which is inserted into the applicator main unit 51, so as to coincide the longitudinal direction of the piercing device 52 with that of the first shaft 56a. The piercing device 52 is capable of changing a relative position between itself and the applicator main unit 51 by sliding the first shaft 56a with respect to the applicator main unit 51.

In the rear portion of the applicator main unit 51, a female thread hole is formed in a radial direction of the applicator main unit 51. Into this female thread, a male thread 61 is screwed. A tip of the male thread 61 protrudes inside the applicator main unit 51. On the other hand, in an outside surface of the first shaft 56a, a groove 56b is formed along the longitudinal direction of the first shaft 56a. Into the groove 56b of the first shaft 56a inserted into the applicator main unit 51, the tip of the male thread 61 is loosely fitted. As a result, the groove 56b defines a range of movement of the first shaft 56a with respect to the applicator main unit 51. When the male thread 61 is further screwed into the female thread hole to press the tip thereof against a bottom surface of the groove 56b, it is possible to hold the first shaft 56a at any position with respect to the applicator main unit 51.

The stylet operation portion 57 includes: a cylindrical second shaft 62 that is inserted into an inside of the first shaft 56a from a rear end thereof; a lever 63 that is swingably supported by the first shaft 56a supporting the piercing device 52; a torsion coil spring 64 for biasing the lever 63 in a direction for spacing the lever 63 away from the applicator main unit 51; and a link mechanism 65 for transforming a swing of the lever 63 into a linear movement along the piercing device 52 of the stylet 53.

The base end of the stylet 53 is inserted into an interior of the second shaft 62 from the tip thereof. It is fixedly attached to the second shaft 62 so that the longitudinal direction of the stylet 53 is coincided with that of the second shaft 62. The stylet 53 is capable of changing a relative position between itself and the piercing device 52 by sliding the second shaft 62 with respect to the first shaft 56a.

The link mechanism 65 includes: a base material 66; a bracket 68; a bar 70; a plate member 72; and a compression coil spring 74. The base material 66 is fixed onto an outside surface of the first shaft 56a. The bracket 68 is pivotally supported by the base material 66. The lever 63 has a lower end fixed in the bracket 68. The bar 70 has one end pivotally supported by the bracket 68 and the other end pivotally supported by the base material 66. A pin 71 provided in the other end of the bar 70 is fitted into an oval hole 66a with allowance, the oval hole 66a being formed in the base material 66 along a sliding direction of the second shaft 62.

In the plate member 72, a hole 73 is formed with a diameter larger than the outer diameter of the second shaft 62. The second shaft 62 inserted into the first shaft 56a penetrates through this hole 73. The difference between the outer diameter of the second shaft 62 and the inner diameter of the hole 73 is very slight. When the plate member 72 is moved in the longitudinal direction of the second shaft 62, that is, in the insertion direction of the second shaft 62 into the first shaft 56a, as if the plate member 72 is inclined, an inner surface of the hole 73 interferes with an outer surface of the second shaft 62, thus producing friction. Thereby, the force applied to the plate member 72 acts on the second shaft 62.

The compression coil spring 74 is disposed in an interior of the first shaft 56a. It biases the plate member 72 in a direction opposite to the insertion direction of the second shaft 62 into the first shaft 56a.

When the lever 63 is moved in a direction of going closer to the applicator main unit 51, the bar 70 is pulled to the front direction of the applicator main unit 51 via the bracket 68, causing the other end of the bar 70 to move along the oval hole 66a. The plate member 72 is pressed forward by the other end of the bar 70 to move in the insertion direction of the second shaft 62 into the first shaft 56a while resisting the compression coil spring 74. At this time, the plate member 72 is slightly inclined to produce friction between itself and the second shaft 62. As a result, the force applied to the plate member 72 acts on the second shaft 62, causing the second shaft 62 to be pushed into the first shaft 56a. When the lever 63 is released, the torsion coil spring 64 spaces the lever 63 away from the applicator main unit 51. In addition, the compression coil spring 74 pushes the plate member 72 back to an initial position without producing friction between the plate member 72 and the second shaft 62.

A movement amount of the other end of the bar 70 for one operation on the lever 63 is always constant. Accordingly, an insertion length of the second shaft 62 into the first shaft 56a for one operation on the lever 63 is always constant as well. Therefore, it is possible to control the insertion length of the second shaft 62 into the first shaft 56a, that is, the insertion length of the stylet 53 into the piercing device 52 according to the number of operations on the lever 63. This means that it is possible to control the length of the tissue fastener 10A which is pushed out from the tip of the piercing device 52 according to the number of operations on the lever 63.

Here, when the tissue fastener 10A is of a coil shape as in the present embodiment, it is preferable that the insertion length of the stylet 53 for one operation on the lever 63 be substantially n times or substantially 1/n (n is a natural number) the circumference of the tissue fastener 10A. For example, if the insertion length of the stylet 53 for one operation on the lever 63 is substantially equal to the circumference of the tissue fastener 10A, one turn amount of the tissue fastener 10A is pushed out from the tip of the piercing device 52 for every one operation on the lever 63. If the length of the second tissue fixation portion 12 is equal to two turns of the tissue fastener 10A, it is possible to push out only the second tissue fixation portion 12 from the tip of the piercing device 52 through two operations on the lever 63. If the insertion length of the stylet 53 for one operation on the lever 63 is substantially equal to a half circumference of the tissue fastener 10A, a half turn amount of the tissue fastener 10A is pushed out from the tip of the piercing device 52 for every one operation on the lever 63. Furthermore, if the length of the second tissue fixation portion 12 is equal to two turns of the tissue fastener 10A, it is possible to push out only the second tissue fixation portion 12 from the tip of the piercing device 52 through four operations on the lever 63.

The sheath operation portion 58 includes a first ring member 58a that is arranged in an interior of the applicator main unit 51 and through an internal hole of which the piercing device 52 is inserted. The first ring member 58a has an outer diameter slightly smaller than an inner diameter of the front portion of the applicator main unit 51. The first ring member 58a has an inner diameter substantially the same as that of the sheath 54. Therefore, the first ring member 58a is slidable with respect to an inner surface of the front portion of the applicator main unit 51. The base end of the sheath 54 is fixedly attached to a front face of the first ring member 58a so as to coincide the center of the sheath 54 with that of the first ring member 58a. The sheath 54 is capable of changing a relative position between itself and the applicator main unit 51 by sliding the first ring member 58a with respect to the applicator main unit 51.

The stent pusher operation portion 59 is arranged especially in an anterior of the first ring member 58a in the interior of the applicator main unit 51. It includes a second ring member 59a through an internal hole of which the sheath 54 is inserted. The second ring member 59a has an outer diameter slightly smaller than an inner diameter of the front portion of the applicator main unit 51. The second ring member 59a has an inner diameter substantially the same as that of the stent pusher 55 of a sheath tube shape. Therefore, the second ring member 59a is slidable with respect to an inner surface of the front portion of the applicator main unit 51. The base end of the stent pusher 55 is fixedly attached to a front face of the second ring member 59a so as to coincide the center of the stent pusher 55 with that of the second ring member 59a. The stent pusher 55 is capable of changing a relative position between itself and the applicator main unit 51 by sliding the second ring member 59a with respect to the applicator main unit 51.

As shown in FIG. 1, in an outside surface of the second ring member 59a, a female thread hole is formed in a radial direction of the second ring member 59a. On the other hand, in the front portion of the applicator main unit 51, an oval hole 51a is formed along a sliding direction of the second ring member 59a. Into the female thread of the second ring member 59a, a male thread 76 is screwed through the oval hole 51a. As a result, the oval hole 51a defines a range of movement of the second ring member 59a with respect to the applicator main unit 51. When the male thread 76 is further screwed into the female thread hole to press the head portion of the thread against the applicator main unit 51, it is possible to hold the second ring member 59a at any position with respect to the applicator main unit 51.

Figure 4:
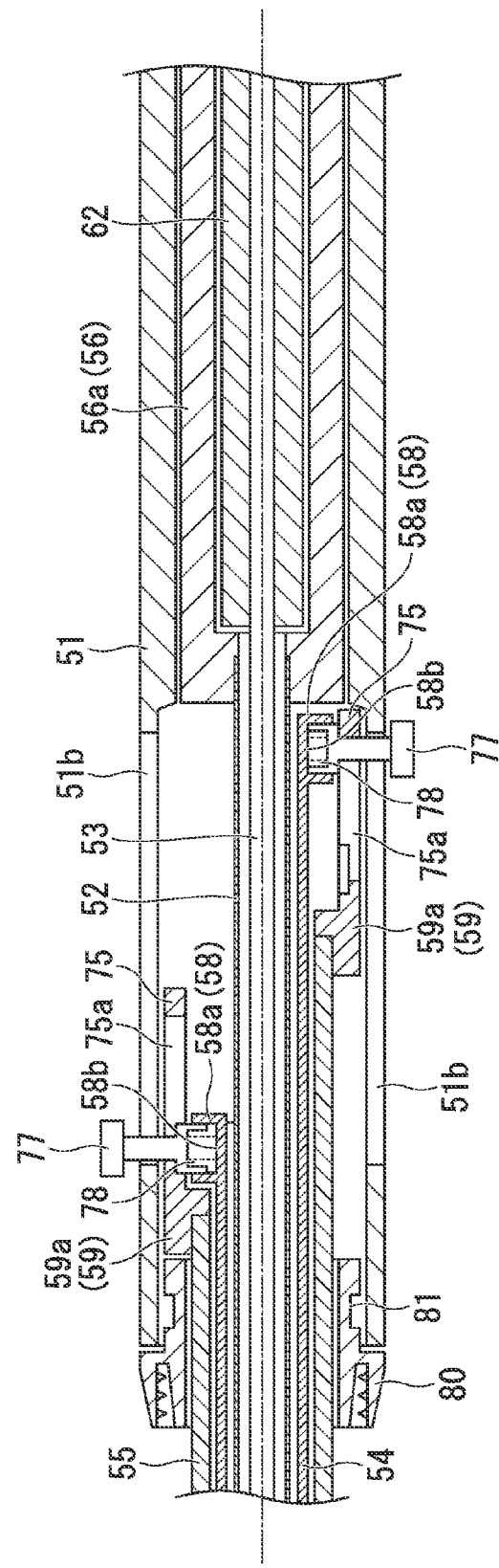
FIG. 4 shows an arrangement of first and second ring members provided in the above applicator in the interior of the apparatus. The upper half is a cross-sectional view showing a state in which the first and second ring members are arranged close to a front end of the applicator main unit. The lower half is a cross-sectional view showing a state in which the first and second ring members are arranged close to a rear end of the applicator main unit.

In an outside surface of the first ring member 58a, as shown in FIG. 4, two recessed portions 58b are formed. On the other hand, on the second ring member 59a, two bars 75 that protrude backward are provided. In the respective two bars 75, an oval hole 75a is formed along a sliding direction of the first ring member 58a with respect to the applicator main unit 51. Furthermore, in the applicator main unit 51, two oval holes 51b that extend parallel to the oval hole 75a are formed. Into the two recessed portions 58b of the first ring member 58a, the two pins 77 are inserted through the oval hole 51b of the applicator main unit 51 and the oval hole 75a of the second ring member 59a, respectively. As a result, the oval hole 75a defines a range of movement of the first ring member 58a with respect to the second ring member 59a. The second ring member 59a itself slides with respect to the applicator main unit 51. Therefore, the oval hole 51b is formed longer than the oval hole 75a in consideration of not only the range of movement of the first ring member 58a but also the range of movement of the second ring member 59a.

Figure 5:
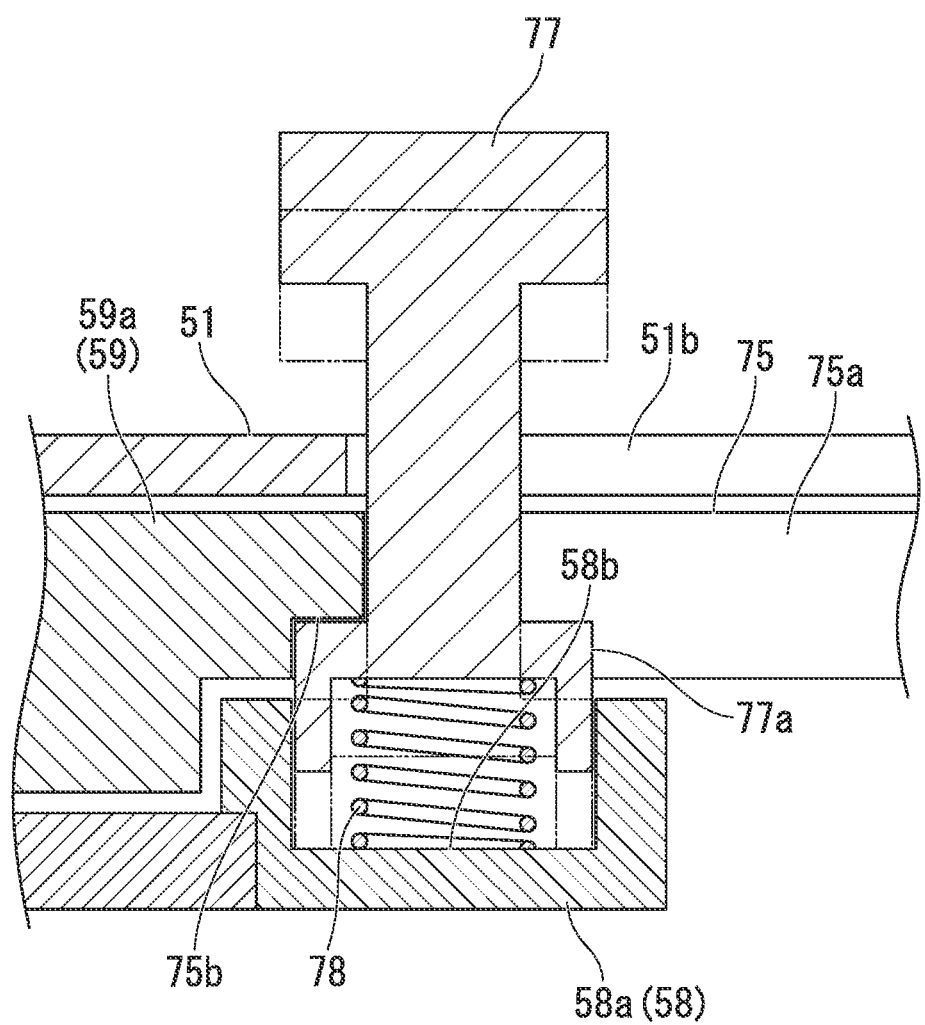
FIG. 5 is a cross-sectional view showing a structure of a pin for restraining the above first ring member on the second ring member.

Between the recessed portion 58b and a tip of the pin 77, a compression spring 78 is interposed, as shown in FIG. 5. As a result, the pin 77 is always biased outwardly in a radial direction of the second ring member 59a. In the bar 75, a recessed portion 75b is formed with which a large diameter portion 77a of the pin 77 is engaged when the first ring member 58a is arranged at the position closest to a tip face of the second ring member 59a.

When the first ring member 58a is arranged at the position closest to the tip face of the second ring member 59a, the large diameter portion 77a of the pin 77 is engaged with the recessed portion 75b of the bar 75. Therefore, the first ring member 58a is restrained by the second ring member 59a via the pin 77. When the pin 77 is pushed into the applicator main unit 51 against a biasing force of the compression spring 78, the large diameter portion 77a of the pin 77 is detached from the recessed portion 75b. Consequently, the first ring member 58a is released from the second ring member 59a, and hence becomes capable of being moved toward a rear end of the applicator main unit 51. Therefore, it is possible to move the sheath 54 to the hand side with respect to the stent pusher 55.

Into a tip of the applicator main unit 51, a pipe sleeve 80 is inserted. On the pipe sleeve 80, an inside screw is formed. By screwing this inside screw into a pipe sleeve 8 of an endoscope 2, it is possible to fix the applicator 50 to the endoscope 2. In an outside surface of 80, a groove 81 is formed along a circumferential direction. On the other hand, on the applicator main unit 51, a female thread hole is formed in a radial direction of the applicator main unit 51. Into this female thread hole, a male thread 82 is screwed. A tip of the male thread 82 protrudes inside the applicator main unit 51. Into the groove 81 of the pipe sleeve 80, the tip of the male thread 82 is loosely fitted. As a result, it is possible to freely rotate the applicator main unit 51 with respect to the pipe sleeve 80 fixed on the endoscope 2. When the male thread 82 is further screwed into the female thread hole to press the tip thereof against a bottom surface of the groove 81, it is possible to hold the applicator main unit 51 at any position with respect to the pipe sleeve 80.

Figure 6:
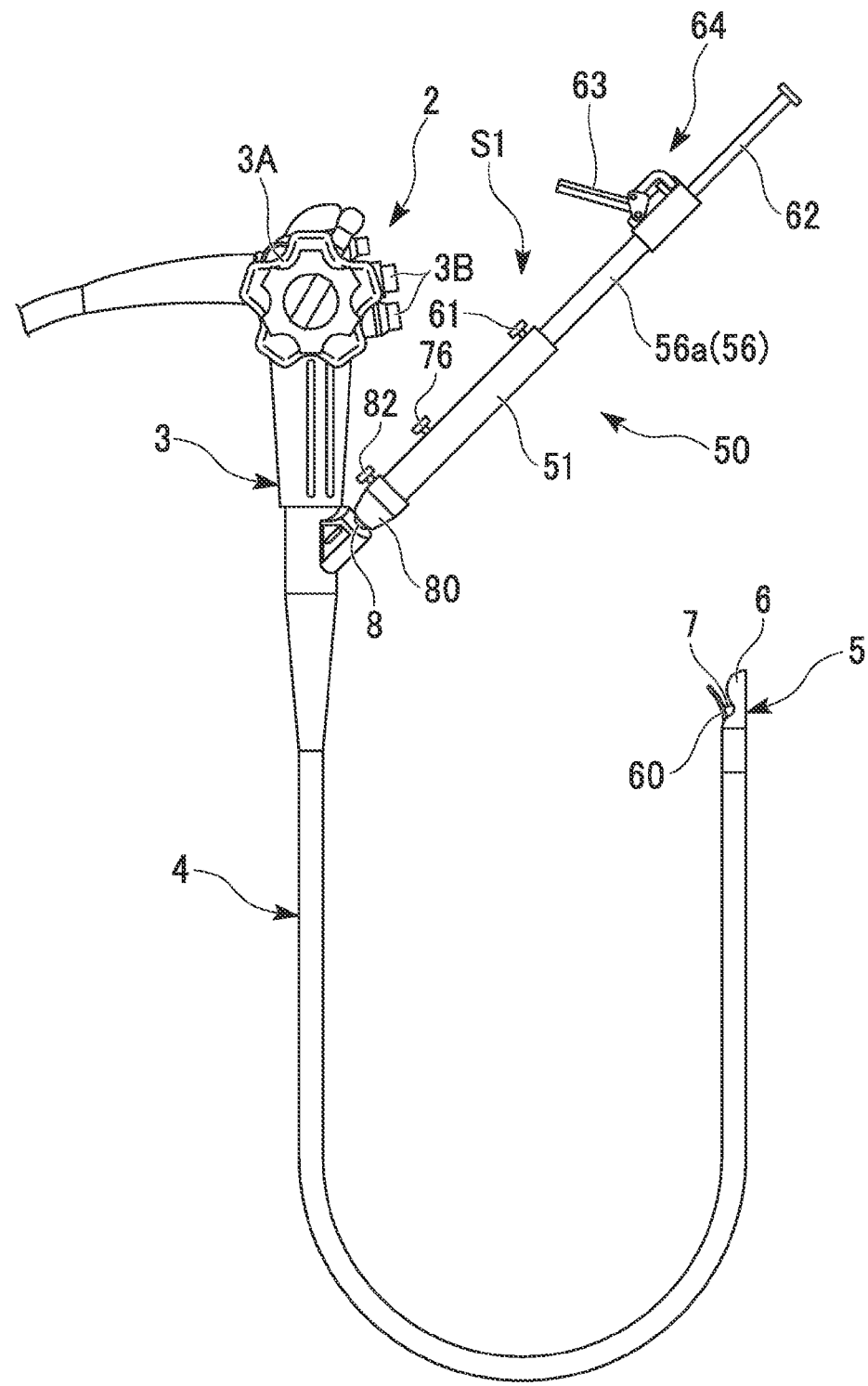
FIG. 6 shows a state in which an insertion portion of the applicator is inserted into a work channel of an endoscope.

FIG. 6 shows a linear scanning ultrasonic endoscope as an endoscope 2 for use with the tissue fastening apparatus S1. This endoscope 2 includes a flexible insertion portion 4 extending from an operation portion 3 for use outside the body. To the operation portion 3, a knob 3A for curving a tip portion of the insertion portion 4 and various buttons 3B are disposed. To a tip of the insertion portion 4, a cover 5 is attached. To this cover 5, an ultrasonic apparatus 6 is attached. The ultrasonic apparatus 6 swells out on a plane including an axis line of the insertion portion 4. It has a plurality of ultrasonic transducers arranged along an arc-shaped outer circumference. Furthermore, the endoscope 2 is provided with an elevator 7 so that the tip of the applicator 50 can be sent out laterally. With an operation on the elevator 7 at hand, it is possible to adjust an orientation of an insertion portion 60 of the applicator 50 which is sent out from the tip of the insertion portion 4. Note that the endoscope 2 may be provided with an ultrasonic apparatus of another probe type. In addition, an endoscope without an ultrasonic apparatus 6 may be used. In this case, an ultrasonic apparatus for use outside the body, or an X-ray apparatus, a magnetic resonance imaging (MRI) system, or a CT (Computerizing Tomography) apparatus is additionally used.

Figure 7:
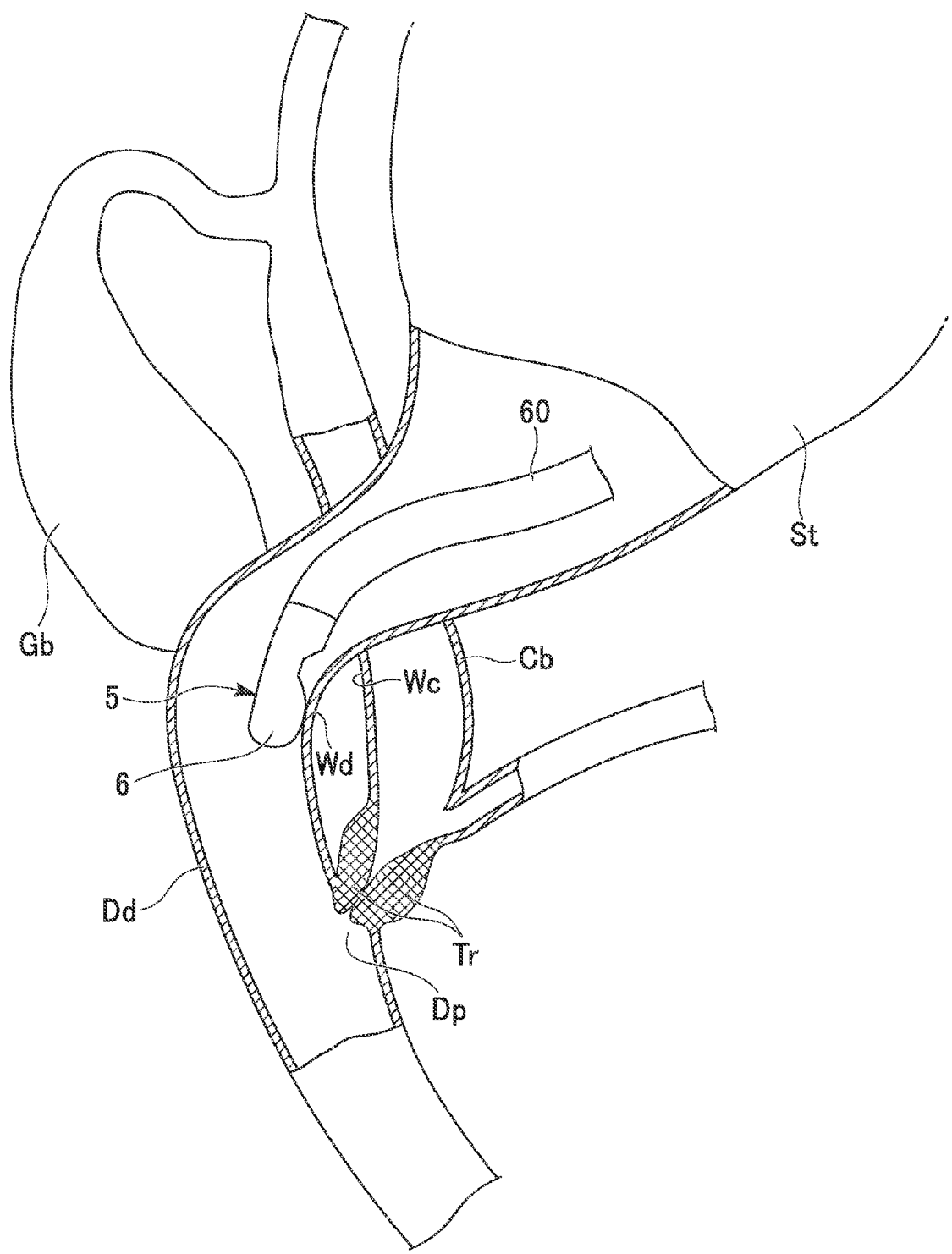
FIG. 7 shows a state in which the insertion portion of the endoscope is inserted into a duodenum.

Next is a description of a manipulation in which the tissue fastening apparatus S1 configured as above is used to fix a common bile duct on a duodenum and to communicate both. Such a manipulation is executed in the case where bile is mixed into blood to develop jaundice as a result of inability to discharge bile due to obstruction of a duodenal papilla Dp by a tumor Tr, as shown in FIG. 7. With this manipulation, it is possible to discharge bile directly from a common bile duct Cb to a duodenum Dd.

First, the insertion portion 4 of the endoscope 2 is inserted from a mouth of a patient. The endoscope 2 is inserted into the duodenum Dd, which is an upper gastrointestinal tract. With the ultrasonic apparatus 6, a state of an outside of the duodenum Dd is checked for a site appropriate for the manipulation, the site being on a side closer to a stomach St than a duodenal papilla Dp and being close to the common bile duct Cb.

Figure 8:
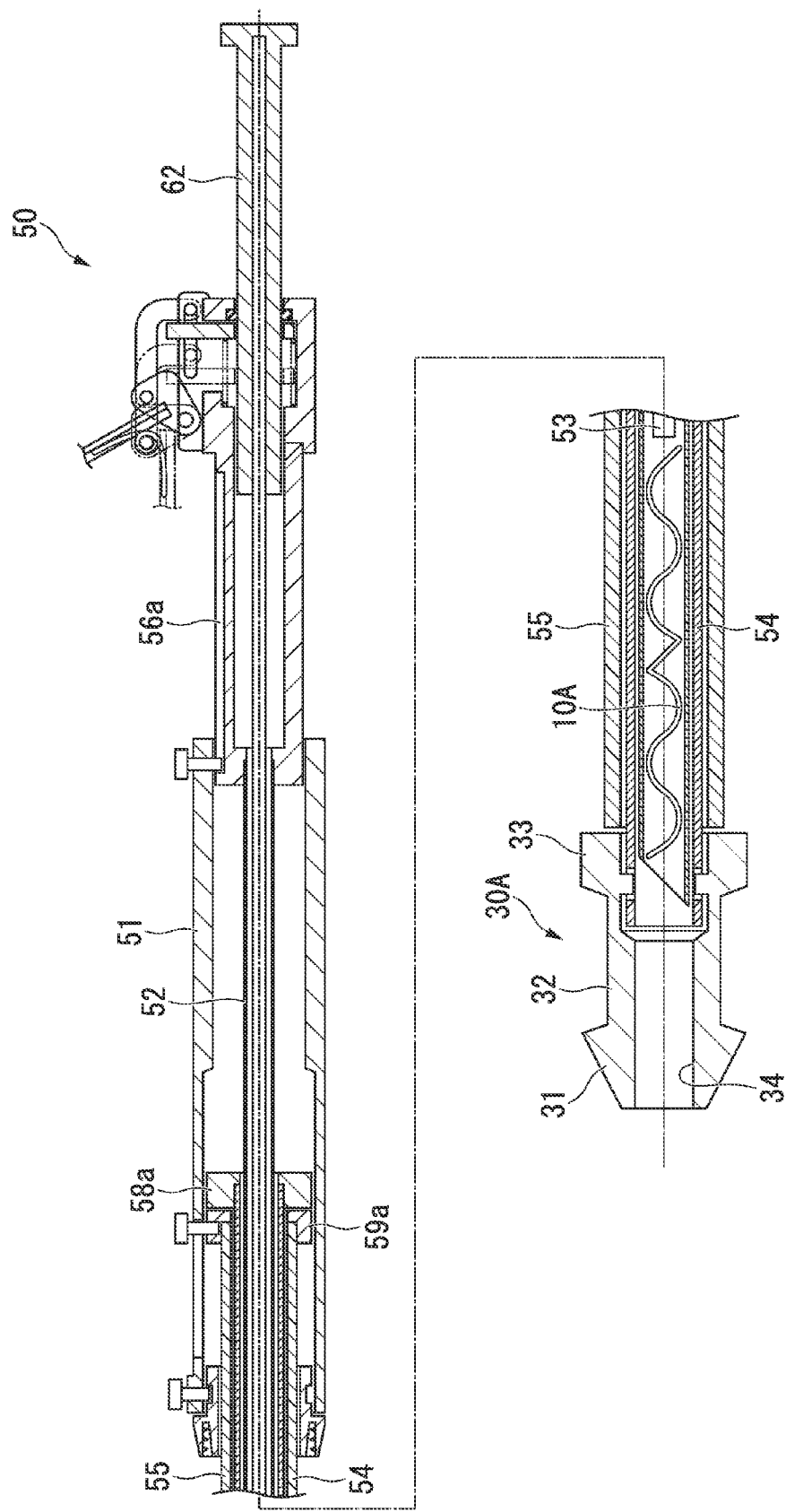
FIG. 8 to FIG. 14 are cross-sectional views showing how an applicator is used in the respective steps of performing a manipulation for fixing a common bile duct onto a duodenum and communicating both organs.

In the applicator 50, the first shaft 56a is operated in advance to move back the piercing device 52 with respect to the applicator main unit 51, and the second shaft 62 is previously operated to move back the stylet 53 with respect to the applicator main unit 51, as shown in FIG. 8. Furthermore, the first ring member 58a and the second ring member 59a are simultaneously operated in advance to move back the sheath 54 and the stent pusher 55 with respect to the applicator main unit 51. However, the first ring member 58a is arranged at a position closest to the second ring member 59a. In this condition, the piercing device 52 with the tissue fastener 10A inserted thereinto is pulled inside the sheath 54 until the tip thereof is arranged in the interior of the stent 30A.

The insertion portion 60 of the applicator 50 is inserted into a work channel of the endoscope 2 and then is moved forward, to thereby fix the applicator 50 onto the endoscope 2. As a result, the tip of the insertion portion 60 is caused to protrude from the tip of the insertion portion 4 of the endoscope 2. Then, the orientation of the protruded insertion portion 60 is adjusted with the elevator 7.

Figure 9:
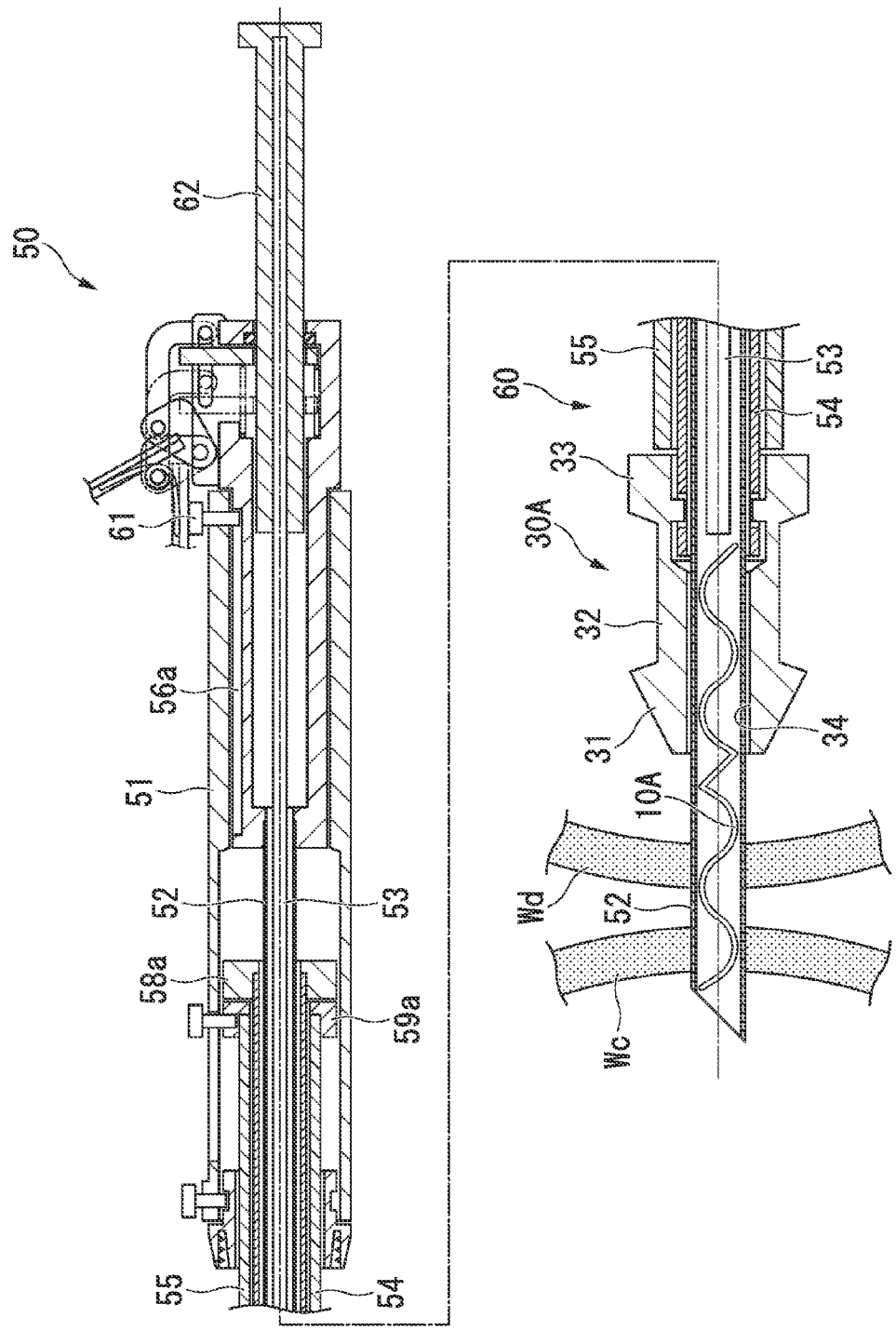

The ultrasonic apparatus 6 provided to the endoscope 2 is used to scan the common bile duct Cb across the duodenum Dd to determine a position at which the piercing device 52 is piercingly inserted into the common bile duct Cb. Then, as shown in FIG. 9, the male thread 61 is loosened and the first shaft 56a is pushed into the applicator main unit 51 to protrude the tip of the piercing device 52 from the tip of the stent 30A attached to the tip of the sheath 54. As a result, the sharp tip of the piercing device 52 is pierced through an intestinal wall Wd of the duodenum Dd from the inside to the outside, and subsequently is pierced through a duct wall Wc of the common bile duct Cb from the outside to the inside. Then, the male thread 61 is tightened to fix the first shaft 56a onto the applicator main unit 51.

Figure 10:
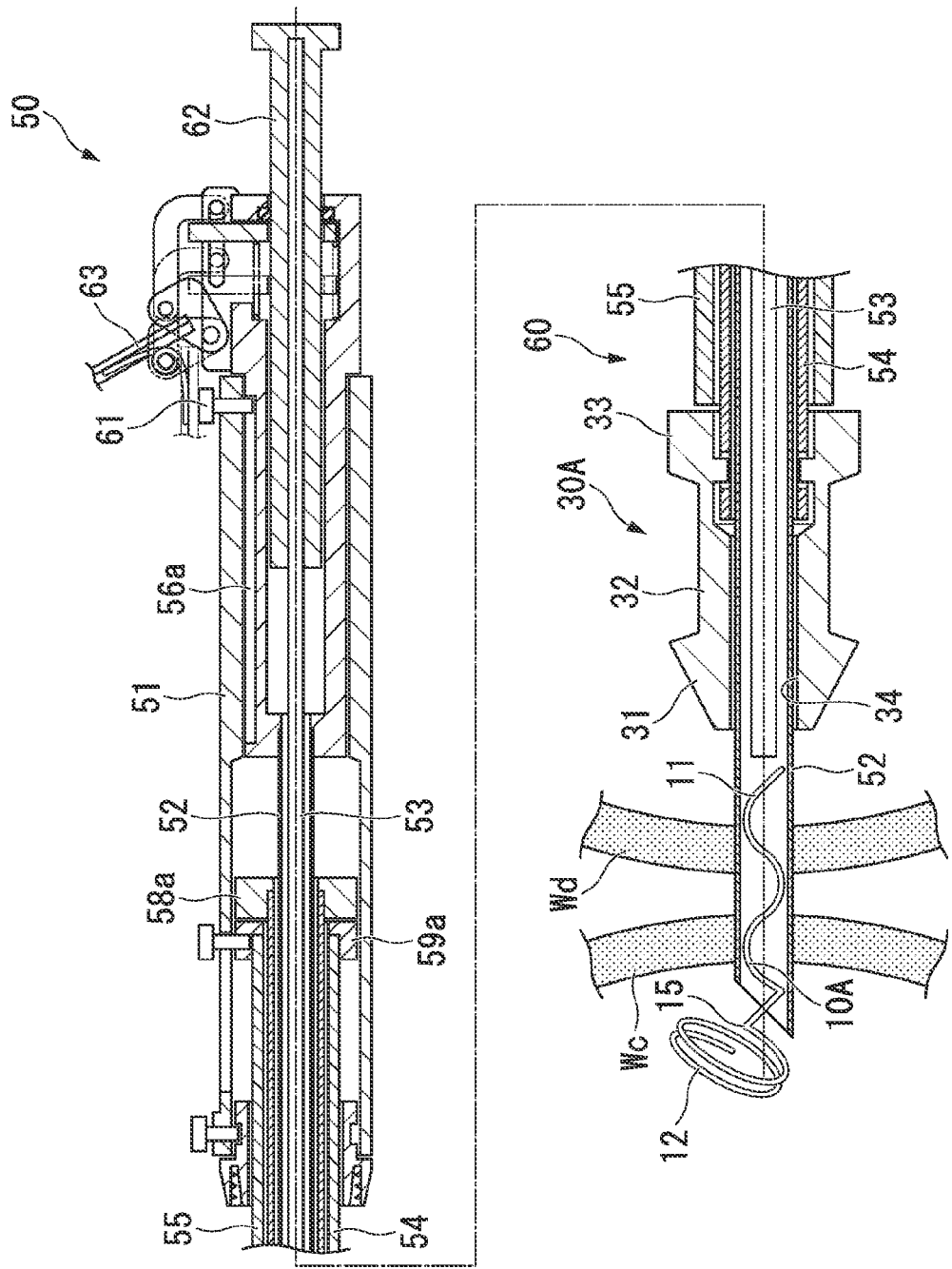

As shown in FIG. 10, the lever 63 is operated to push the second shaft 62 into the S first shaft 56a by a predetermined amount. For example, the lever 63 is operated a predetermined number of times. As a result, the stylet 53 changes its relative position to the piercing device 52. Thereby, the second tissue fixation portion 12 of the tissue fastener 10A is pushed out from the tip of the piercing device 52. The second tissue fixation portion 12, when pushed out from the piercing device 52, assumes its original coil shape, and is locked on the inside of the duct wall Wc of the common bile duct Cb.

Then, the male thread 61 is loosened, and the first shaft 56a is pulled out a little from the applicator main unit 51 to shorten the protrusion length of the piercing device 52 from the tip of the stent 30A. Furthermore, the male thread 61 is tightened to fix the first shaft 56a onto the applicator main unit 51. As a result, the tip of the piercing device 52 is spaced apart a little from the inside surface of the intestinal wall Wd of the duodenum Dd.

Figure 11:
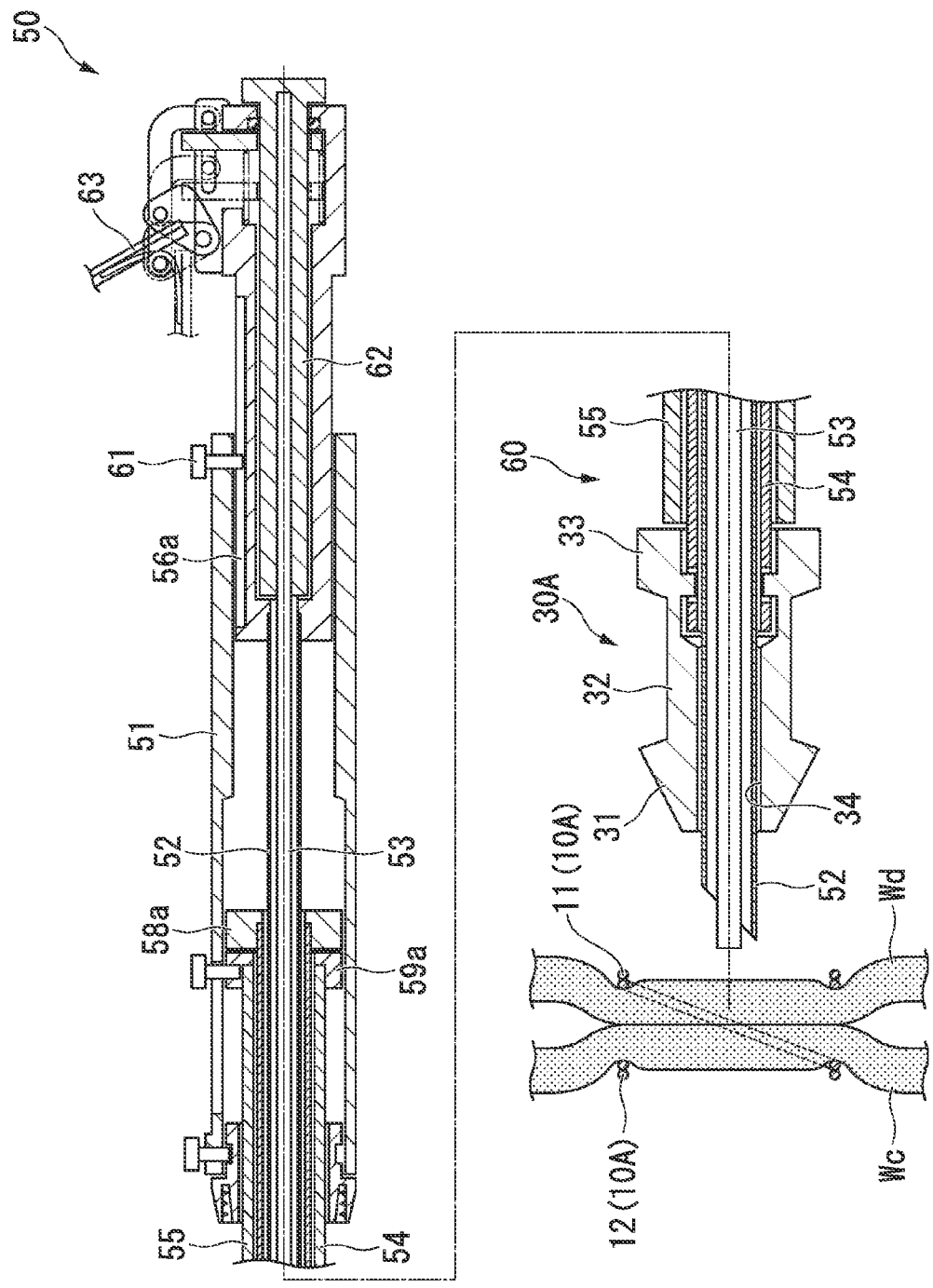

As shown in FIG. 11, the lever 63 is operated again to push the second shaft 62 into the first shaft 56a by a predetermined amount. For example, the lever 63 is operated a predetermined number of times. As a result, the stylet 53 changes its relative position to the piercing device 52. Thereby, the linking portion 13 and the first tissue fixation portion 11 of the tissue fastener 10A are pushed out from the tip of the piercing device 52. The first tissue fixation portion 11, when pushed out from the piercing device 52, assumes its original coil shape, and is locked on the inside of the intestinal wall Wd of the duodenum Dd.

The tissue fastener 10A, when pushed out from the piercing device 52, clamps the duodenum Dd and the common bile duct Cb as if to cause the intestinal wall Wd of the duodenum Dd locked on by the first tissue fixation portion 11 and the duct wall Wc of the common bile duct Cb locked on by the second tissue fixation portion 12 to press against each other.

Figure 12:
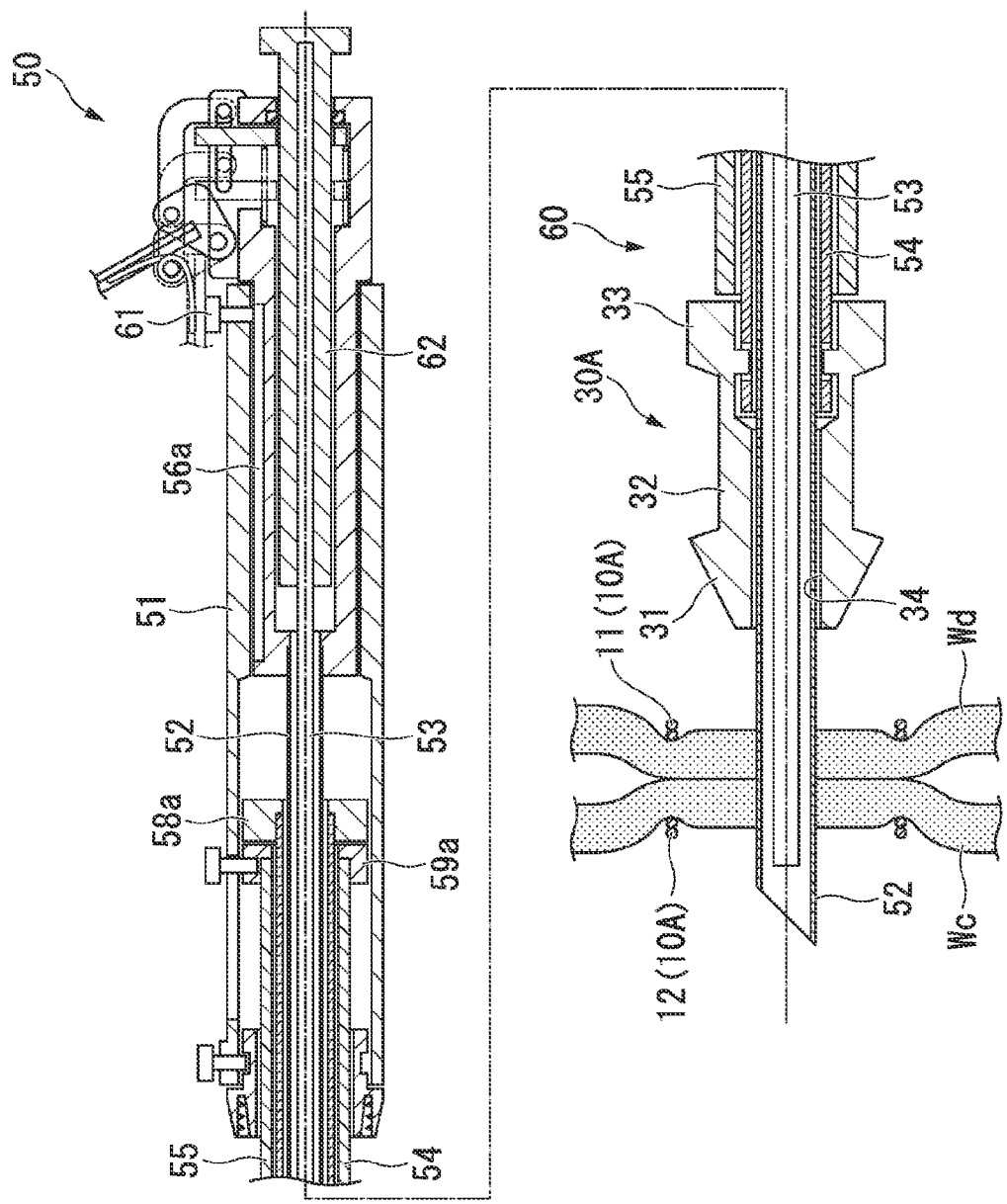

As shown in FIG. 12, the second shaft 62 is pulled a little to retract the tip of the stylet 53 inside the piercing device 52. Then, the male thread 61 is loosened, and the first shaft 56a is again pushed into the applicator main unit 51 to protrude the tip of the piercing device 52 from the tip of the stent 30A. As a result, the sharp tip of the piercing device 52 is pierced through the intestinal wall Wd of the duodenum Dd and the duct wall Wc of the common bile duct Cb inside the tissue fastener 10A. Then, the male thread 61 is tightened to fix the first shaft 56a onto the applicator main unit 51. The lever 63 is further operated to push the second shaft 62 completely into the first shaft 56a. As a result, the smooth tip of the stylet 53 is protruded from the sharp tip of the piercing device 52. Therefore, the possibility of the sharp tip of the piercing device 52 carelessly injuring the surrounding tissue is eliminated.

Figure 13:
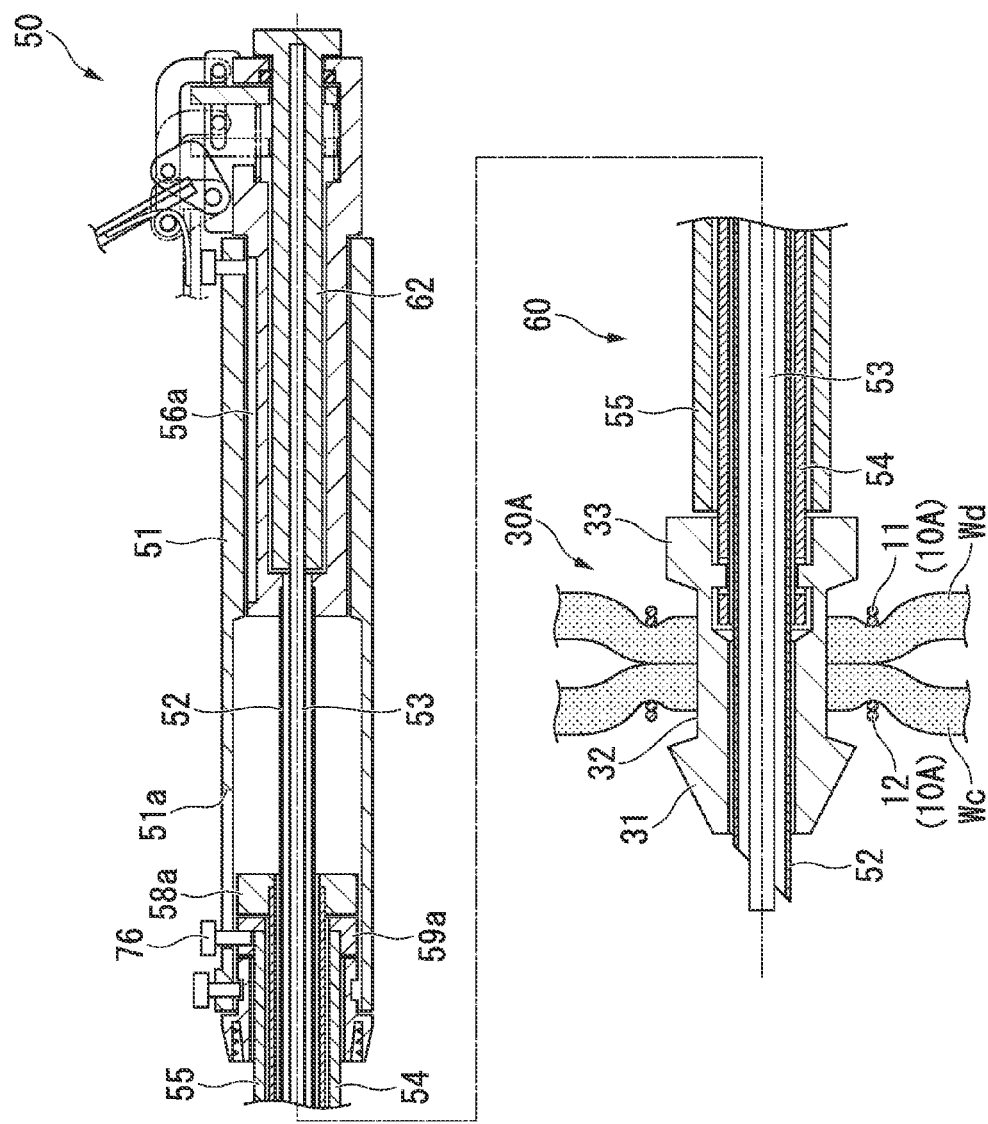

As shown in FIG. 13, the male thread 76 is loosened, and then the first ring member 58a and the second ring member 59a are moved toward the tip of the applicator main unit 51. This changes relative positions of the sheath 54 and the stent pusher 55 with respect to the piercing device 52 that is fixed onto the applicator main unit 51 via the first shaft 56a. As a result, the stent 30A is pressed forward along the piercing device 52. Then, the extension portion 31 of the stent 30A is pierced through the intestinal wall Wd of the duodenum Dd and the duct wall Wc of the common bile duct Cb from the inside of the tissue fastener 10A so as to and widen a bore that has been opened by the piercing device 52. When the extension portion 31 has penetrated through the intestinal wall Wd of the duodenum Dd and the duct wall Wc of the common bile duct Cb, the stent 30A is placed in the intestinal wall Wd of the duodenum Dd and the duct wall Wc of the common bile duct Cb in a state with the placement portion 32 being arranged within the intestinal wall Wd and the duct wall Wc, the extension portion 31 being protruded inside the common bile duct Cb, and the slip-off prevention portion 33 being left inside the duodenum Dd. After the stent 30A is placed, the male thread 76 is tightened to fix the second ring member 59a onto the applicator main unit 51.

Figure 14:
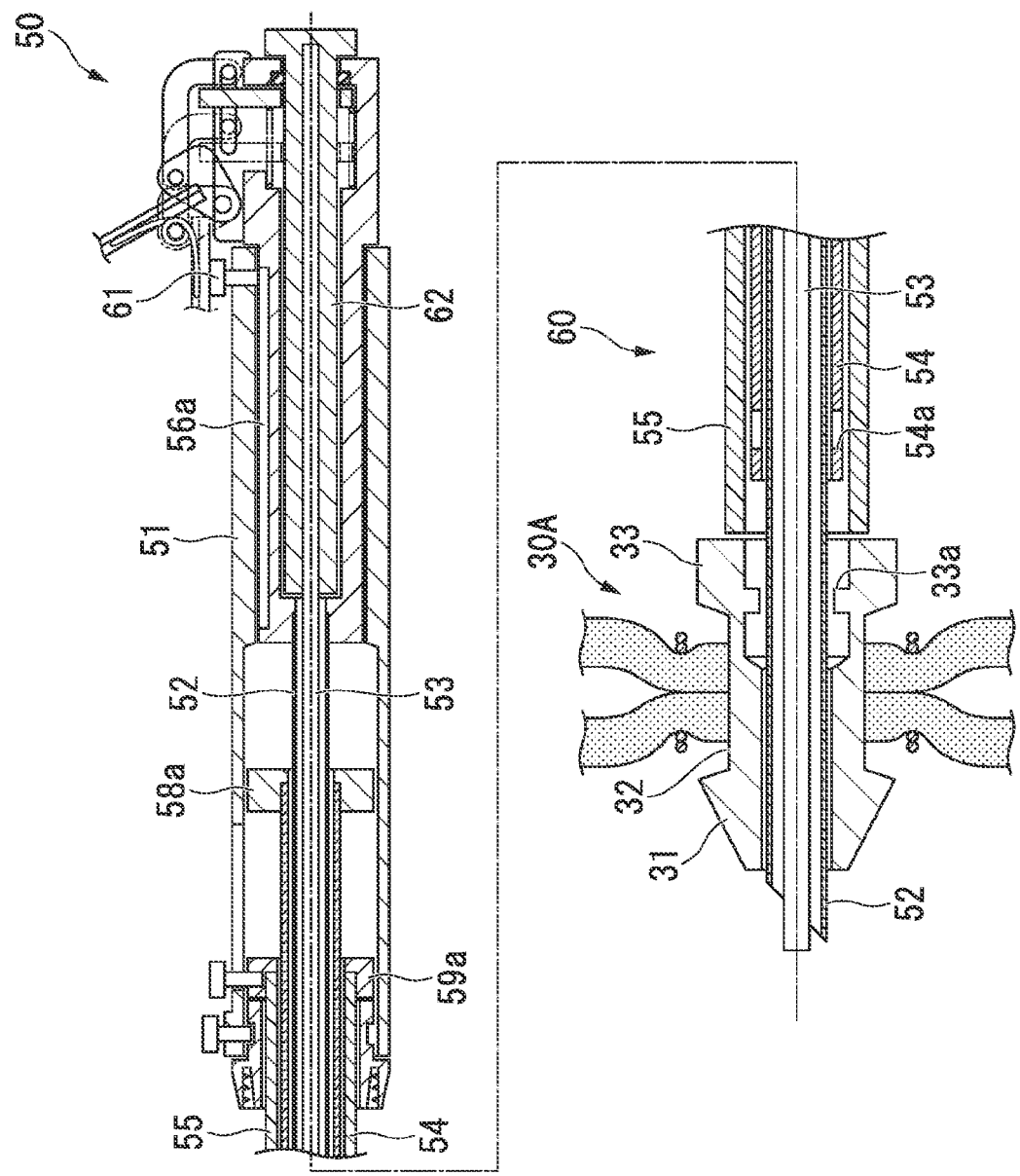

While pressing the pin 77 shown in FIG. 4 into the applicator main unit 51, the first ring member 58a is moved toward the rear end of the applicator main unit 51, as shown in FIG. 14. At this time, the second ring member 59a is fixed onto the applicator main unit 51. Therefore, the relative position between the sheath 54 and the stent pusher 55 is changed, and hence the sheath 54 is pulled to the hand side. However, the stent 30A tries to stay in position because it is abutted with the tip face of the stent pusher 55. As a result, the tip of the sheath 54 is elastically deformed, causing the protrusions 33a of the stent 30A to be detached from the small holes 54a of the sheath 54. When the protrusions 33a are detached from the small holes 54a, the tip of the sheath 54 is pulled into the stent pusher 55. As a result, the stent 30A is disengaged from the tip of the insertion portion 60 of the applicator 50.

Next, the male thread 61 is loosened, the first shaft 56a is pulled out from the applicator main unit 51, and the tip of the piercing device 52 is pulled into the tip of the sheath 54. Then, the male thread 61 is tightened to fix the first shaft 56a onto the applicator main unit 51. Subsequently, the applicator 50 is removed from the endoscope 2. Thus, the fastening of the intestinal wall Wd of the duodenum Dd and the duct wall Wc of the common bile duct Cb by the tissue fastener 10A is finished, and also the placement of the stent 30A in the interiors of the intestinal wall Wd of the duodenum Dd and the duct wall Wc of the common bile duct Cb is finished. As a result, the duodenum Dd and the common bile duct Cb are communicated through the through-hole 34 of the stent 30A. Thereby, bile is discharged from the common bile duct Cb to the duodenum Dd.

When the tissue fastener 10A is left in a living body, the intestinal wall Wd of the duodenum Dd and the duct wall Wc of the common bile duct Cb are compressed by the tissue fastener 10A, thus putting the biological tissue inside the tissue fastener 10A in an ischemic state. A continued ischemic state necrotizes the biological tissue. On the other hand, outside the tissue fastener 10A, the intestinal wall Wd and the duct wall Wc are adhered over the entire circumference of the tissue fastener 10A. As a result, the necrotized biological tissue and the tissue fastener 10A and the stent 30A fall off from the intestinal wall Wd and the duct wall Wc. The tissue fastener 10A and the stent 30A are excreted later. In the intestinal wall Wd and the duct wall Wc from which the necrotized biological tissue has fallen off, an anastomotic fistula is formed. Through this anastomotic fistula, the duodenum Dd and the common bile duct Cb are communicated, and hence bile is discharged from the common bile duct Cb to the duodenum Dd. The margin of the anastomotic fistula is adhered over the entire circumference. Therefore, bile will not leak into the abdominal cavity from between the intestinal wall Wd and the duct wall Wc.

According to the applicator 50, an operation on the lever 63 as if to hold it lightly allows the tissue fastener 10A to be pushed out from the piercing device 52 easily and accurately. Furthermore, it is possible to separate the stent 30A from the tip of the sheath 54 at a proper timing. As a result, it is possible to suitably place the tissue fastener 10A and the stent 30A at a desired position in a living body.

In addition, according to the applicator 50, when the sheath 54 and the stent pusher 55 are used to press the stent 30A against the intestinal wall Wd of the duodenum Dd and the duct wall Wc of the common bile duct Cb, the piercing device 52 is immovably held in position. As a result, organs will not be injured unexpectedly by the piercing device 52, and the safety operation can be performed.

Next is a description of a behavior of the tissue fastener 10A that is pushed out from the tip of the piercing device 52.

First of all, a method of forming a through hole that communicates between a first hollow organ tissue and a second hollow organ tissue which is adjacent to the first hollow organ tissue, includes the steps of: inserting a needle tube which holds a tissue fastening instrument into the first hollow organ tissue and the second hollow organ tissue in an extended state, wherein the tissue fastening instrument includes a first tissue fixing portion and a second tissue fixing portion which are formed by being wound in a coil shape, and a peripheral spring portion that is wound in a shape of a spiral around periphery of the first tissue fixing portion and the second tissue fixing portion, that extends in an outer diameter direction, and that connects to the second tissue fixing portion; engaging the first tissue fixing portion, which is restored to a coil shape, with the first hollow organ tissue by allowing the tissue fastening instrument to extrude from the needle tube; pulling out the needle tube from the first hollow organ tissue and the second hollow organ tissue; holding and fastening the first hollow organ tissue and the second hollow organ tissue between the first tissue fixing portion and the second tissue fixing portion by using the second tissue fixing portion extruded from the needle tube and restored to a coil shape, after the needle tube is pulled out from the first hollow organ tissue and the second hollow organ tissue; and pressing an outside portion of the first hollow organ tissue and the second hollow organ tissue which is surrounded by the first tissue fixing portion and the second tissue fixing portion as seen from an axis direction of the tissue fastening instrument by using the peripheral spring portion extruded from the needle tube and restored to a spiral shape, after the first hollow organ tissue and the second hollow organ tissue are extruded from the needle tube.

Specifically, the tissue fastener 10A is first pushed out so as to protrude only the second tissue fixation portion 12 from the tip of the piercing device 52 that has penetrated through the intestinal wall Wd of the duodenum Dd and the duct wall Wc of the common bile duct Cb. The second tissue fixation portion 12, in the process of being pushed out from the tip of the piercing device 52, successively assumes its original coil shape, and is locked on the duct wall Wc of the common bile duct Cb.

The second tissue fixation portion 12, in the process of being pushed out from the tip of the piercing device 52, generates force for restoring its own shape to its original coil shape. With this force acting on the duct wall Wc of the common bile duct Cb, the tissue fastener 10A may be pulled inside the common bile duct Cb by an amount more than the push-out amount of the stylet 53. However, the tissue fastener 10A is provided with the linking portion 13 between the first tissue fixation portion 11 and the second tissue fixation portion 12. In addition, the bent portion 15 is formed between the second tissue fixation portion 12 and the linking portion 13. As a result, if the whole of the second tissue fixation portion 12 is pushed out, the second tissue fixation portion 12 changes orbit from one in the process of being pushed out from the tip of the piercing device 52, as shown in FIG. 10. This is because when the bent portion 15 of the tissue fastener 10A is pushed out from the tip of the piercing device 52, the second tissue fixation portion 12 that is released from the restraint by the piercing device 52 changes its orientation depending on the angle of the bent portion 15. With the change in orientation of the second tissue fixation portion 12, even if force is generated in the second tissue fixation portion 12 for restoring its own shape to its original coil shape, the force ceases to act on the duct wall Wc of the common bile duct Cb. Therefore, the tissue fastener 10A will not be pulled inside the common bile duct Cb by more than a push-out amount of the stylet 53.

After that, the whole tissue fastener 10A including the remaining first tissue fixation portion 11 is pushed out from the tip of the piercing device 52, which has been pulled out from the intestinal wall Wd of the duodenum Dd and the duct wall Wc of the common bile duct Cb. The first tissue fixation portion 11, in the process of being pushed out from the tip of the piercing device 52, successively assumes its original coil shape, and is locked on the intestinal wall Wd of the duodenum Dd.

With the first tissue fixation portion 11 locked on the intestinal wall Wd of the duodenum Dd and the second tissue fixation portion 12 locked on the duct wall Wc of the common bile duct Cb, the intestinal wall Wd and the duct wall Wc are clamped. The linking portion 13 is placed in the interiors of the intestinal wall Wd and the duct wall Wc that are clamped. Because the gap G is provided between the first tissue fixation portion 11 and the second tissue fixation portion 12, the intestinal wall Wd and the duct wall Wc are clamped so that they press against each other with uniform force.

It is preferable that the angle θ1 of the linking portion 13 with respect to the first tissue fixation portion 11 and the angle θ2 of the linking portion 13 with respect to the second tissue fixation portion 12 be both 45° or less (see FIG. 3). when the angles θ1, θ2 are larger than 45°, the bent portion 14 forming the angle θ1 and the bent portion 15 forming the angle θ2 come into contact with the inner surface of the piercing device 52 in the process of pushing out the tissue fastener 10A from the tip of the piercing device 52, resulting in production of strong frictional force. This makes it difficult to smoothly push out the tissue fastener 10A from the piercing device 52.

It is preferable that the gap G between the first tissue fixation portion 11 and the second tissue fixation portion 12 be 15 mm or less. When the gap G is 15 mm or less, it is possible to fix biological tissue by use of the applicator 50, in substantially all the organs which can be approached using the endoscope 2.

However, plural types of tissue fastener 10A with difference in the size of the gap G are provided in order to offer an optional selection according to the thickness of the organ to be treated or to characteristics of individual patients. Appropriate selection and use of these makes it possible to perform a suitable treatment in various situations.

Figure 15A:
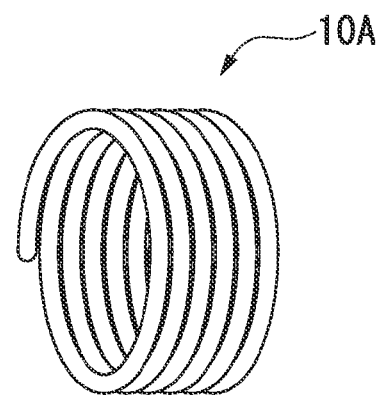
Figure 15B:
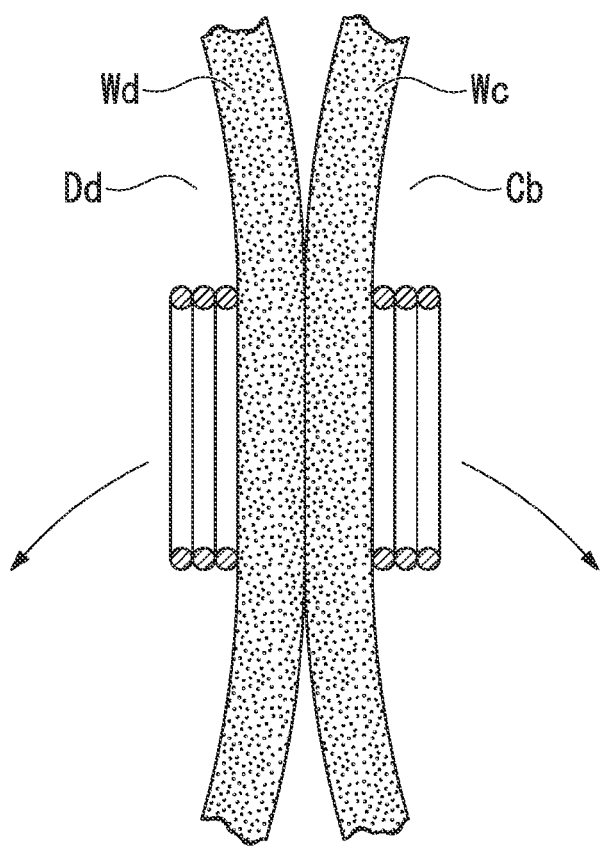

As described above, the portion of the intestinal wall Wd of the duodenum Dd and the duct wall Wc of the common bile duct Cb inside the tissue fastener 10A is compressed by the tissue fastener 10A into an ischemic state. Later, the portion is necrotized and the tissue fastener 10A and the stent 30A fall off the other portions of the intestinal wall Wd and the duct wall Wc. At that time, as shown in FIG. 15B, there are cases where the tissue fastener 10A and/or the stent 30 fall(s) off to the intestinal wall Wd side of the duodenum Dd and to the duct wall Wc side of the common bile duct Cb. If the tissue fastener 10A and/or the stent 30 fall(s) off to the intestinal wall Wd side of the duodenum Dd, they are (it is) excreted out of the body via the small intestine and the large intestine as a result of natural processes. Therefore, this poses no problem. However, if the tissue fastener 10A and/or the stent 30 fall(s) off to the duct wall Wc side of the common bile duct Cb, they are (it is) left there.

Figure 15C:
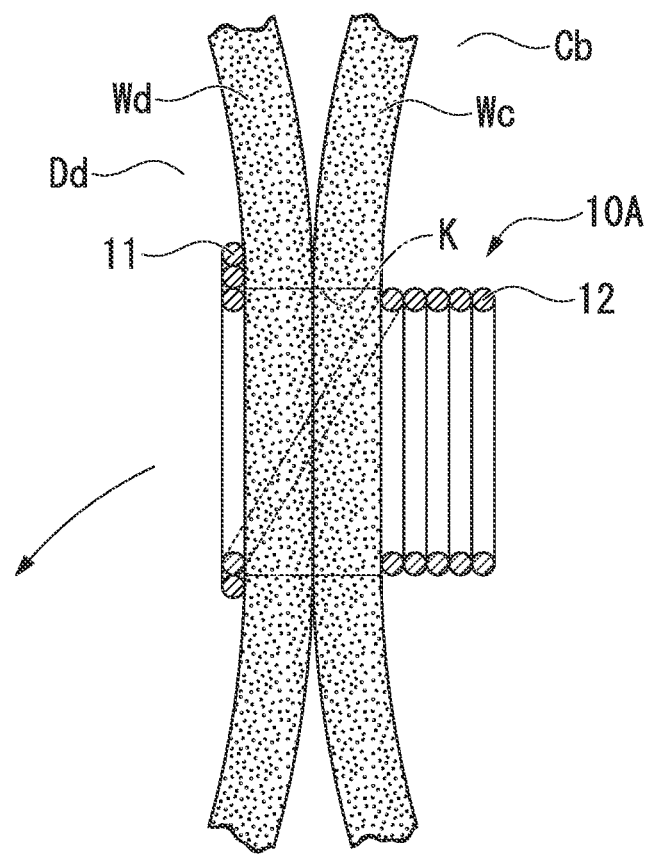

To avoid such inconvenience, the outer diameter of the first tissue fixation portion 11 is made larger than that of second tissue fixation portion 12 in this embodiment, as shown in FIG. 2. That is, as shown in FIG. 15C, an inner diameter of a anastomotic fistula K formed after living tissue, which has been clamped by the tissue fastener 10A into necrosis, falls off becomes substantially the same as an outer diameter of the second tissue fixation portion 2 (in FIG. 15C, the stent 30A is omitted.). The second tissue fixation portion 12 is capable of passing through this anastomotic fistula K, but the first tissue fixation portion 11 is not. Therefore, when the tissue fastener 10A and the necrotized tissue fall off from the intestinal wall Wd and the duct wall Wc, there is a higher probability that the tissue fastener 10A moves only to the intestinal wall Wd side of the duodenum Dd and falls off.

Note that in the above embodiment, the first tissue fixation portion 12 is made of a highly elastic metal wire wound in a vortex. However, the shape is not limited to this.

Figure 16A:
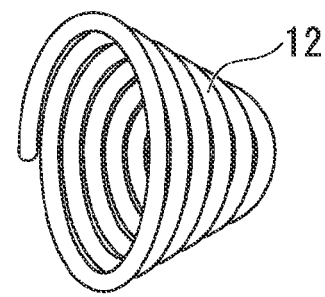
Figure 16B:
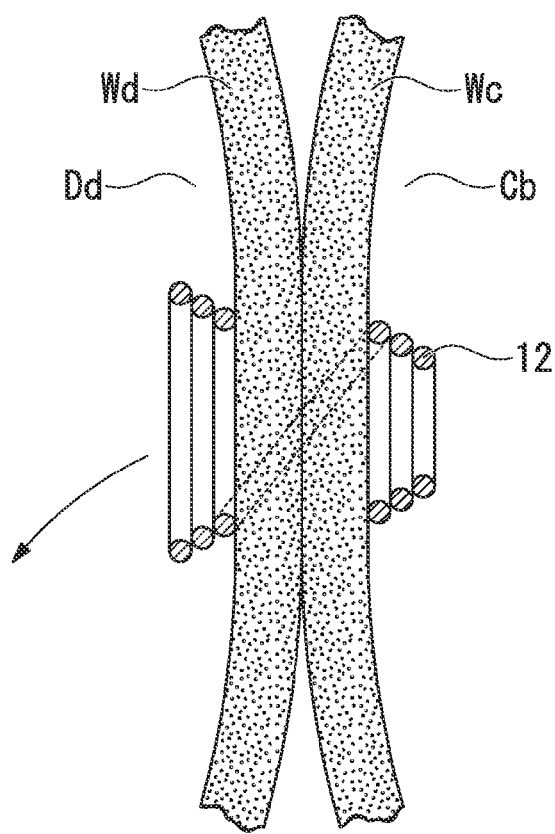

As shown in FIGS. 16A, 16B, the first tissue fixation portion 12 may be made of a highly elastic metal wire wound in a frustum of a cone, or may be made by outwardly protruding a part of a highly elastic metal wire wound in a cylinder. It is essential only that at least a part of the above first tissue fixation portion 11 be protruded outward more than the outer diameter of the second tissue fixation portion 12.

Modifications

Hereunder is a description of modifications of the above embodiment. For convenience of description, like constituent parts to those described in the above embodiment may be designated with like reference numerals to omit repetitious explanation.

Figure 17A:
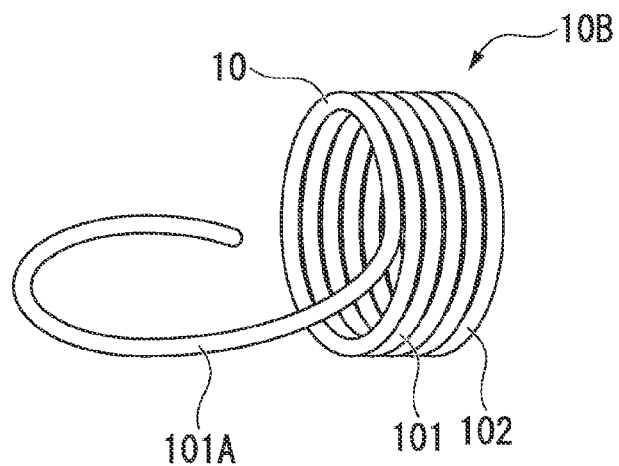
Figure 17B:
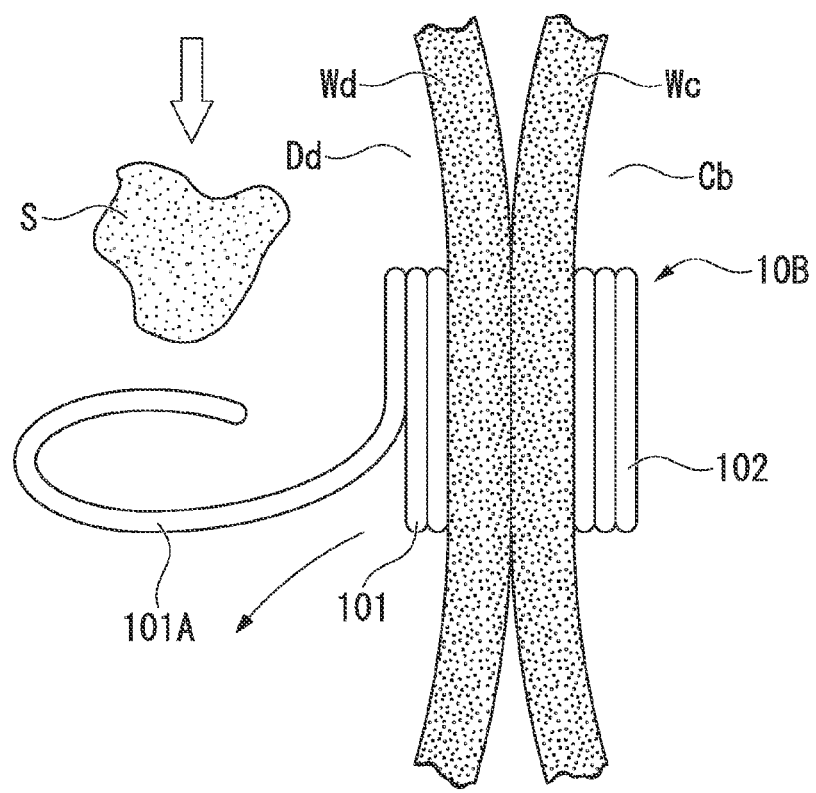

The structure of the tissue fastener is not limited to one described in the above embodiment. For example, a tissue fastener 10B shown in FIGS. 17A, 17B has a first tissue fixation portion 101 and a second tissue fixation portion 102, both of which are made of a highly elastic metal wire 10 wound in a coil. A tip portion of the first tissue fixation portion 101, for example one turn portion 101A at the tip is inclined approximately 90 degrees with respect to the other portion of the first tissue fixation portion 101.

In this modification, for example, food S passes through a duodenum Dd on which the first tissue fixation portion 101 is locked. When passing along an intestinal wall Wd, this food S hits a tip portion 101A of the first tissue fixation portion 101 to thereby press the tip portion 101A to a small intestine side. As a result, when the tissue fastener 10B and the necrotized tissue fall off from the intestinal wall Wd and the duct wall Wc, there is a higher probability that the tissue fastener 10B moves to the intestinal wall Wd side of the duodenum Dd and falls off.

In the case where the tip portion 101A of the first tissue fixation portion 101 is inclined, the number of turns at the tip need not be one. For example, it may be one and a half or two. Furthermore, the inclination angle of the tip portion 101A need not be 90 degrees. The angle at which the tip portion 101A is inclined may be for example in the range of 45 degrees to 135 degrees. It is essential only that the food S hits the tip portion of the first tissue fixation portion 101.

Furthermore, in the case of this modification, no linking portion is provided between the first tissue fixation portion 101 and the second tissue fixation portion 102. The first tissue fixation portion 101 is directly linked with the second tissue fixation portion 102. However, there may be provided a linking portion 13 between the two, as shown in FIG. 2. This may be employed in the following modifications.

Figure 18A:
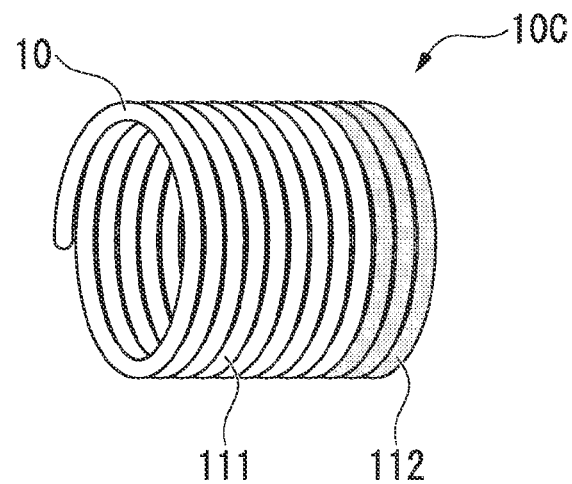
Figure 18B:
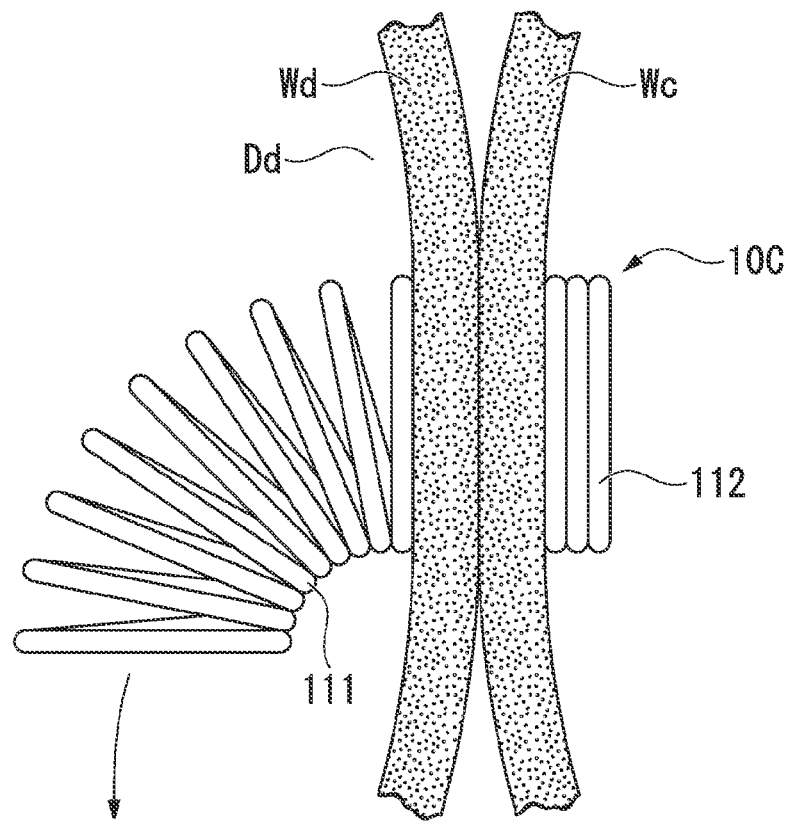

A tissue fastener 10C shown in FIGS. 18A, 18B has a first tissue fixation portion 111 and a second tissue fixation portion 112, both of which are made of a highly elastic metal wire 10 wound in a coil (a cylinder). The number of coil turns of the first tissue fixation portion 111 is larger than that of the second tissue fixation portion 112.

In this modification, the first tissue fixation portion 111 is heavier than the second tissue fixation portion 112 by the increased number of coil turns. Therefore, when the tissue fastener 10C and the necrotized tissue fall off from the intestinal wall Wd and the duct wall Wc, there is a higher probability that the tissue fastener 10A moves to the side of the first tissue fixation portion 111 which is set heavier, that is, to the intestinal wall Wd side of the duodenum Dd and falls off.

When the number of coil turns of the first tissue fixation portion 111 is set to larger than that of the second tissue fixation portion 111, it is preferable that the number be set to a degree such that the difference in weight between these tissue fixation portions is evident, for example to 1.5 or more times than that of the second tissue fixation portion 111.

Figure 19A:
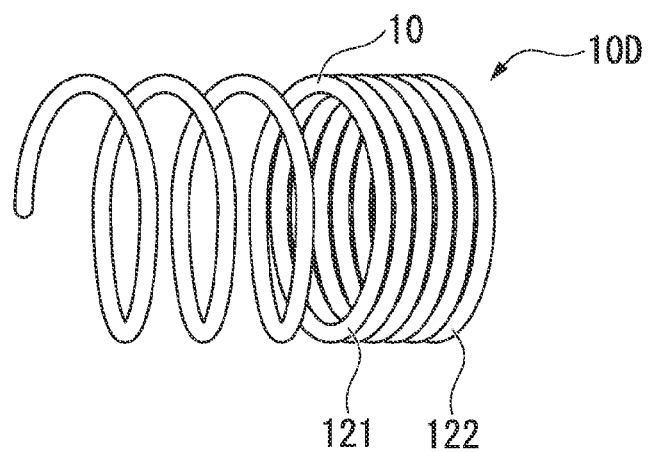
Figure 19B:
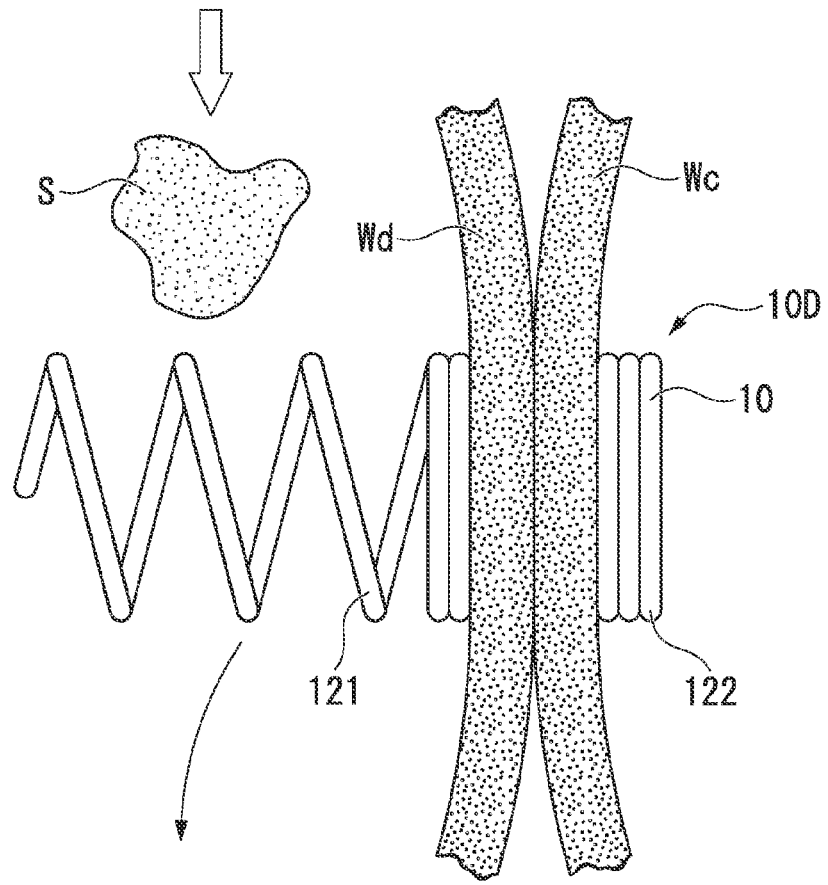

A tissue fastener 10D shown in FIGS. 19A, 19B has a first tissue fixation portion 121 and a second tissue fixation portion 122, both of which are made of a highly elastic metal wire 10 wound in a coil (a cylinder). The coil turn density of the first tissue fixation portion 121 is less than that of the second tissue fixation portion 122. That is, the coil of the highly elastic metal wire of the first tissue fixation portion 121 is roughly wound, and the coil of the highly elastic metal wire of the second tissue fixation portion 121 is densely wound.

In this embodiment, when food S passes along the intestinal wall Wd of the duodenum Dd, there is a higher probability that the food hits the roughly-wound first tissue fixation portion 121. As a result, when the tissue fastener 10D and the necrotized tissue fall off from the intestinal wall Wd and the duct wall Wc, the tissue fastener 10D moves to the intestinal wall Wd side of the duodenum Dd and falls off.

Figure 20:
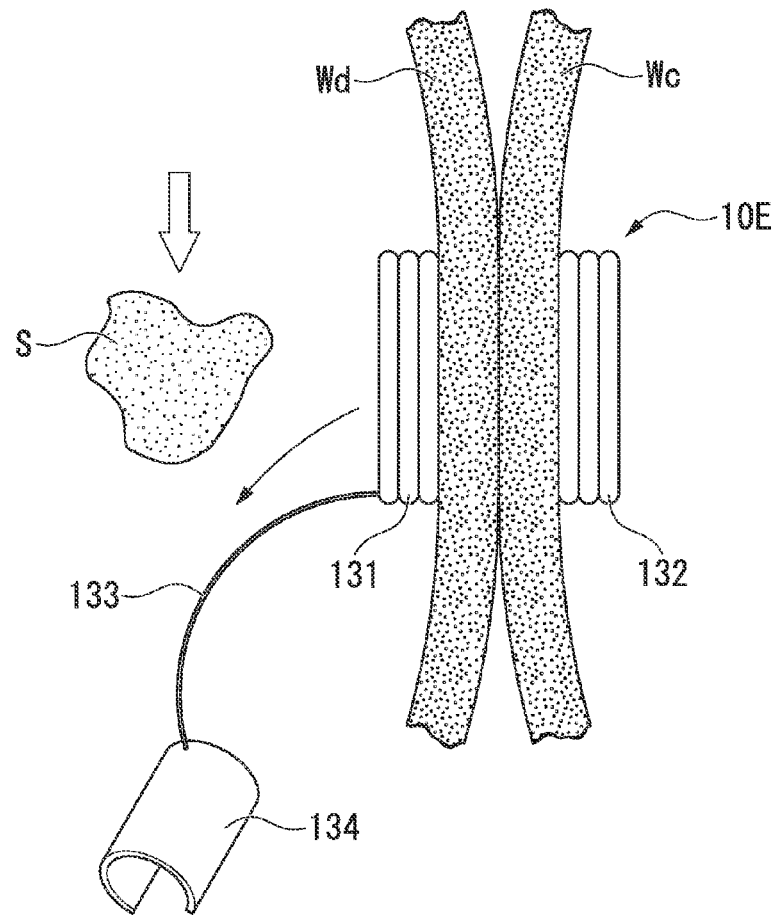

A tissue fastener 10E shown in FIG. 20 has a first tissue fixation portion 131 and a second tissue fixation portion 132, both of which are made of a highly elastic metal wire wound in a coil (a cylinder). To the first tissue fixation portion 131, a resisting entity (anchoring body) 134 is linked via a string member 133. The resisting entity 134 is of a cylindrical shape a part of which is cut out along an axis line direction for easy load in the applicator, as will be described later.

In this modification, when food passes along the intestinal wall Wd of the duodenum Dd, there is a higher probability that this food hits the resisting entity 134. As a result when the tissue fastener 10E and the necrotized tissue fall off from the intestinal wall Wd and the duct wall Wc, there is a higher probability that the tissue fastener 10E moves to the intestinal wall Wd side of the duodenum Dd and falls off. Furthermore, the resisting entity 134 has a weight of its own to some degree. Also due to this weight, there is a higher probability that the tissue fastener 10E moves to the intestinal wall Wd side of the duodenum Dd and falls off.

Figure 21:
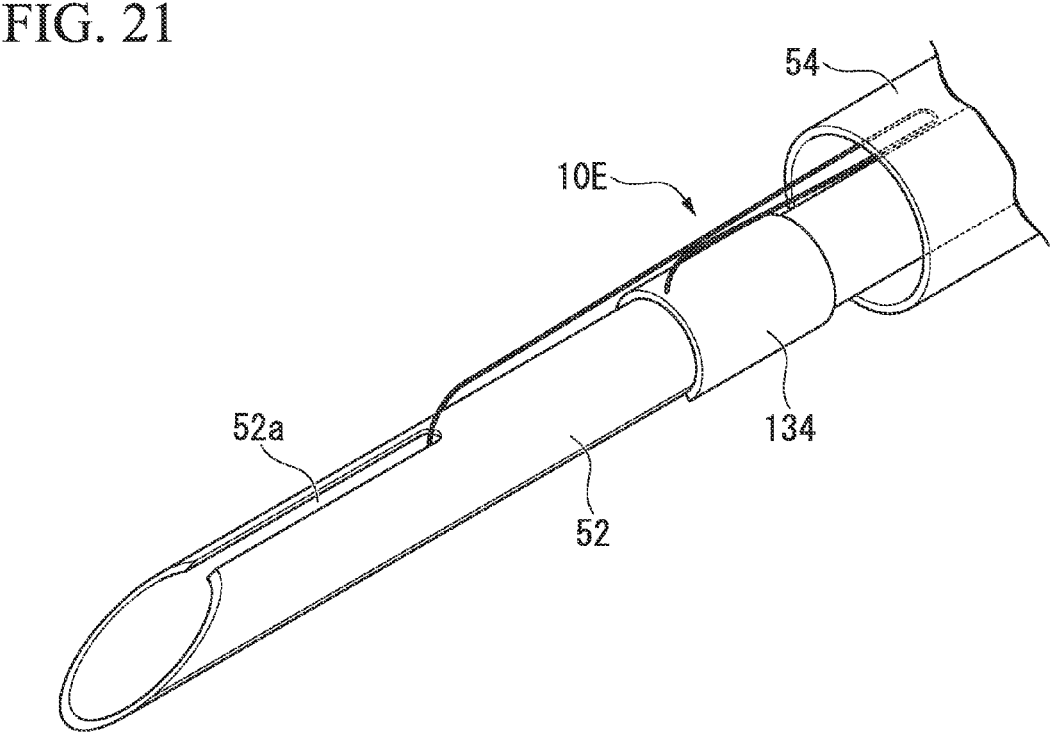

When the resisting entity 134 is loaded in the applicator, a gap between a piercing device 52 and a sheath 54 is utilized as shown in FIG. 21 and FIG. 22. Therefore, a radius of the resisting entity 134 is set between an outer radius of the piercing device 52 and an inner radius of the sheath 54. Furthermore, in the piercing device 52, a slit 52a is formed from its tip to its base end. The string member 133 is arranged by being pulled out from this slit 52a. Thereby, it is loaded on the applicator in a state with the first and second tissue fixation portions 131, 132 loaded inside the piercing device 52 being linked with the resisting entity 134 loaded outside the piercing device.

Figure 23A:
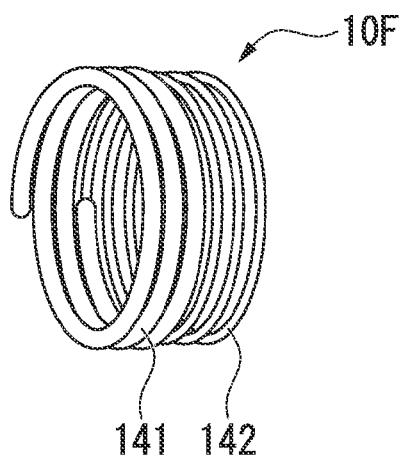
Figure 23B:
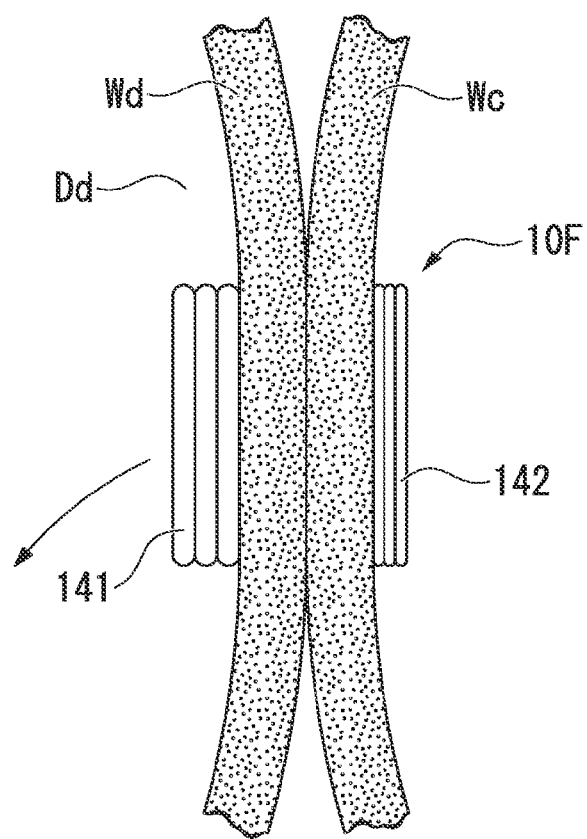

A tissue fastener 10F shown in FIGS. 23A, 23B has a first tissue fixation portion 141 and a second tissue fixation portion 142, both of which are made of a highly elastic metal wire 10 wound in a coil (a cylinder). The first tissue fixation portion 141 and the second tissue fixation portion 142 have substantially the same length. However, a diameter of the highly elastic metal wire constituting the first tissue fixation portion 141 is set to be larger than a diameter of the highly elastic metal wire, which is made of the same material as that for the above, constituting the second tissue fixation portion 142.

In this modification, the first tissue fixation portion 141 is heavier than the second tissue fixation portion 142 by the difference in wire diameter, the former being set to be larger than the latter. Therefore, when the tissue fastener 10F and the necrotized tissue fall off from the intestinal wall Wd and the duct wall Wc, there is a higher probability that the tissue fastener 10A moves to the side of the first tissue fixation portion 141 which is set heavier, that is, to the intestinal wall Wd side of the duodenum Dd and falls off.

Figure 24:
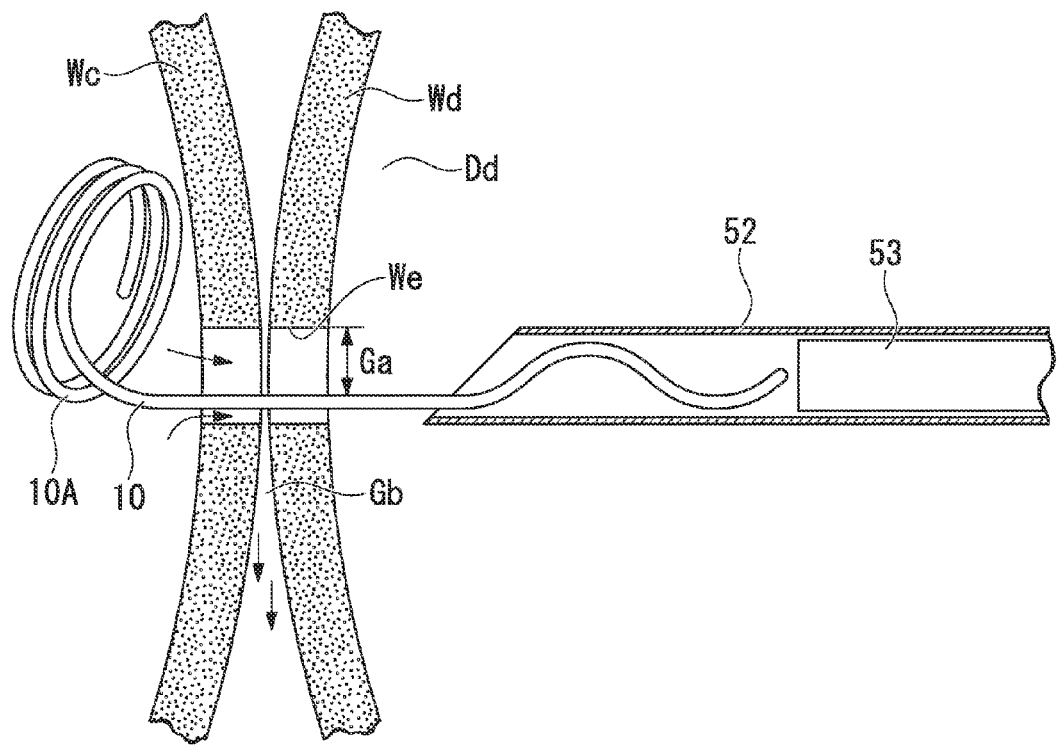

FIG. 24 shows a problem when the tissue fastener 10A is placed in a living body.

Figure 25A:
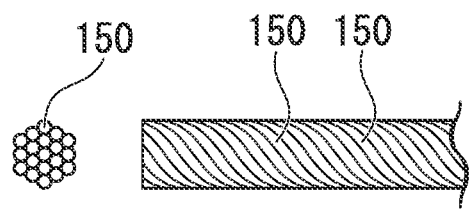
Figure 25B:
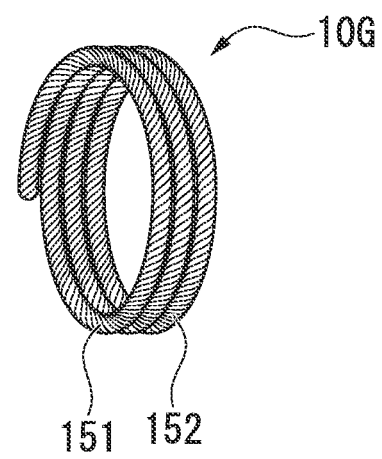

That is, when the tissue fastener 10A is placed in a living body by clamping first biological tissue and second biological tissue so as to be in close contact with each other, firstly a tip of a piercing device 52 of a needle tube shape is piercingly inserted into the intestinal wall Wd and the duct wall Wc. Then, a second tissue fixation portion 12, which is a part of the tissue fastener 10A, is placed in the second biological tissue. After that, when the piercing device 52 is pulled back from these intestinal wall Wd and duct wall Wc, a gap Ga is formed between a hole We that is formed in the intestinal wall Wd and the duct wall Wc when the piercing device 52 is piercingly inserted, and the wire 10 that constitutes the tissue fastener 10A. In the case where liquid is filled in the second biological tissue, which is a lumen, a phenomenon occurs in which the liquid flows through this gap Ga, and further flows through a gap Gb between the intestinal wall Wd and the duct wall Wc, to thereby leak into an abdominal cavity. This situation occurs even after the tissue fastener 10A is placed in the living body. Here, if the liquid that leaks into the abdominal cavity is for example bile, which shows strong alkalinity, there is a possibility of producing bile peritonitis. To prevent such an undesirable situation, a variety of contrivances are adopted as follows:

FIG. 25A, 25B shows a structure in which a highly elastic metal wire constituting a tissue fastener 10G is made of a multitude of highly elastic thin wires 150, not of a single highly elastic thin wire. That is, a first tissue fixation portion 151 and a second tissue fixation portion 152 are made of the multitude of highly elastic thin wires 150 being stranded.

Here, a stranded wire has less elasticity than a single wire. Therefore, supposing that tissue fasteners with the same spring strength are formed, one made of stranded wires allows use of a wire with larger diameter than one made of a single wire.

In this modification, the tissue fastener 10G is made of a multitude of highly elastic thin wires 150, not of a single highly elastic thin wire. This allows use of wires with a diameter larger by that much, for example wires with a diameter substantially the same as an inner diameter of the piercing device 52, for wires constituting the tissue fastener 10G. Thereby, the gap Ga between the hole We of the intestinal wall Wd and the duct wall Wc formed when the piercing device 52 is piercingly inserted can be made as small as possible. As a result, it is possible to prevent a body fluid such as bile from leaking out into an abdominal cavity through this gap Ga.

Note that one shown in FIGS. 25A, 25B has a structure in which the multitude of highly elastic thin wires 150 are stranded over an entire region of the tissue fastener 10G. However, the structure is not limited to this. It will suffice that at least only a linking portion between the first tissue fixation portion 151 and the second tissue fixation portion 152, more specifically, a portion that penetrates through the duct wall Wc and its neighboring area be made of the multitude of highly elastic thin wires 150 being stranded Therefore, the other portions may be made of a single wire.

Figure 26A:
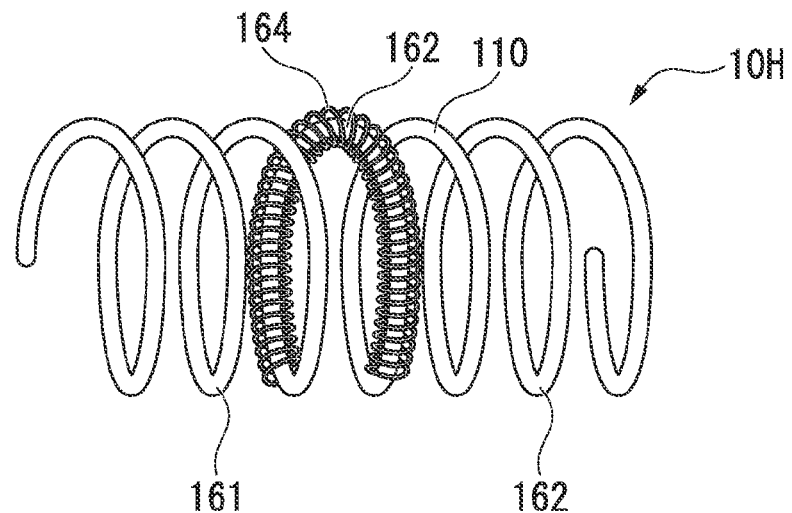
Figure 26B:
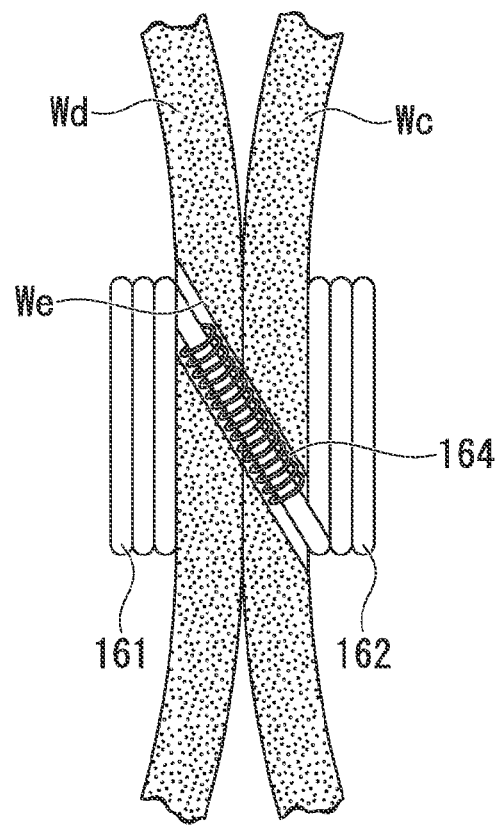

A tissue fastener 10H shown in FIG. 26 has a first tissue fixation portion 161 and a second tissue fixation portion 162, both of which are made of a highly elastic metal wire 10 wound in a coil Around an outer circumference of a linking portion 163 between the first tissue fixation portion 161 and the second tissue fixation portion 162, a thin wire 164 is wound with a smaller diameter than that of the highly elastic metal wire 10. The substantial diameter thereof is set to be approximately equal to an inner diameter of the piercing device.

In this modification, the thin wire 164 is wound around the linking portion 163 between the first tissue fixation portion 161 and the second tissue fixation portion 162 of the tissue fastener 10H, to thereby make its substantial diameter larger. As a result, the gap Ga between the hole We of the intestinal wall Wd and the duct wall Wc formed when the piercing device 52 is piercingly inserted can be made as small as possible, to thereby make it possible to prevent a body fluid such as bile from leaking out into an abdominal cavity through this gap Ga.

Note that in one shown in FIG. 26, the thin wire 164 is wound around a part of the tissue fastener 10H. However the structure is not limited to this. The thin wire 164 may be wound around an entire region of the tissue fastener 10H.

Figure 27:
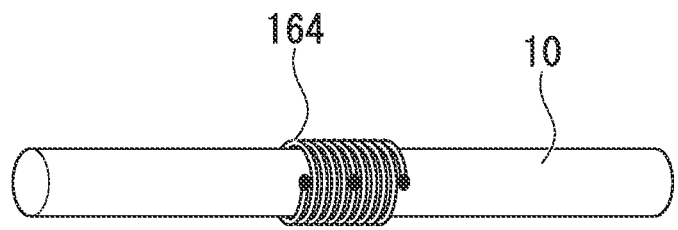
Figure 28A:
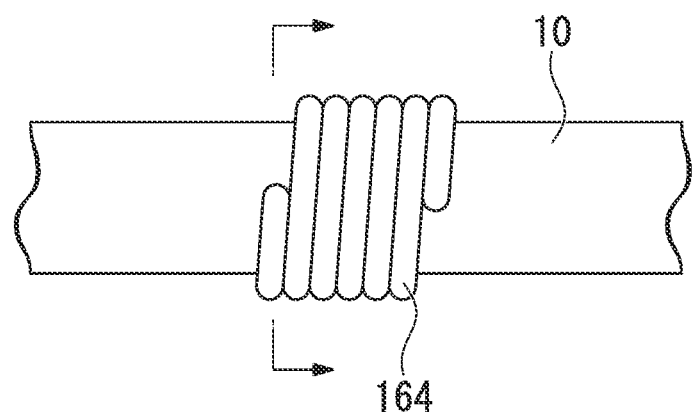
Figure 28B:
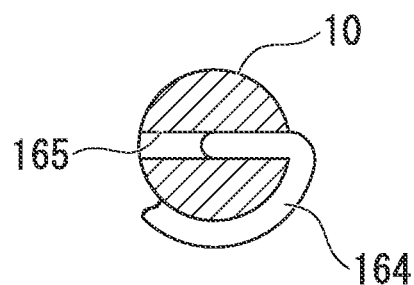

Fixation methods of the thin wire 164 onto the highly elastic metal wire 10 include: a method in which the thin wire 164 is wound around the outer circumference of the highly elastic metal wire 10 for fixation by friction between the two; a method in which after the thin wire 164 is wound, the highly elastic metal wire 10 is fixed onto the thin wire 164 at a plurality of points on the outer circumference by welding or with an adhesive harmless to a human body, as shown in FIG. 27; and a method in which a hole 165 is bored in the highly elastic metal wire 10 and a tip of the thin wire 164 is inserted into this hole 165 for fixation, as shown in FIGS. 28A, 28B.

Furthermore, the thin wire 164 is of a coil shape. Therefore, the end portion of the thin wire 164 is unlikely to come off the hole 165. However, other methods of making the end portion further unlikely to come off are conceivable. They include: a method of press-inserting the end portion of the thin wire 164; a method of fixedly attaching the end portion with an adhesive; a method of applying external force on the highly elastic metal wire 10 in a state with the end portion of the thin wire 164 inserted, to thereby deform the end portion (caulking); and a method of welding the insertion portion.

Figure 29A:
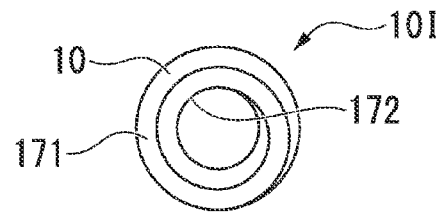
Figure 29B:
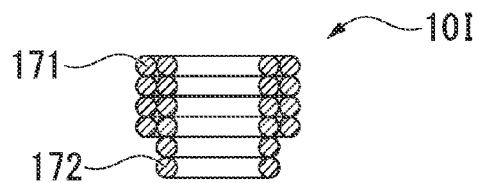

A tissue fastener 101 shown in FIGS. 29A, 29B has a first tissue fixation portion 171 and a second tissue fixation portion 172, both of which are made of a highly elastic metal wire 10 wound in a coil (a cylinder). Around an outer circumference of the second tissue fixation portion 172, the first tissue fixation portion 171 is arranged. That is, the tissue fastener 10I is of a double coil shape made of an inner and outer coils.

Figure 30:
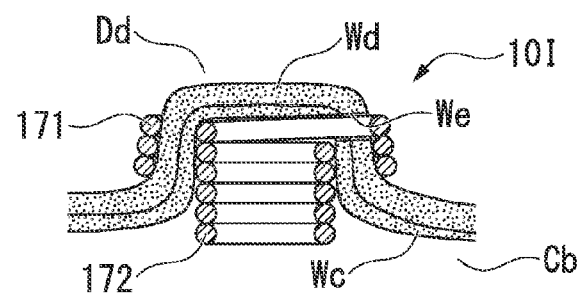

In this modification, as shown in FIG. 30, the second tissue fixation portion 172 on the inner circumference side is locked on the duct wall Wc of the common bile duct Cb as second biological tissue, and the first tissue fixation portion 171 on the outer circumference side is locked on the intestinal wall Wd of the duodenum Dd. In this case, the intestinal wall Wd and the duct wall Wc are brought into close contact with each other by the first tissue fixation portion 171 and the second tissue fixation portion 172, and are clamped in a radial direction. As a result, the intestinal wall Wd and the duct wall Wc, which are on the outer circumference side than the hole We formed when a piercing device 52 is piercingly inserted, that is, on the outer circumference side of an area through which the wire of the tissue fastener 10I penetrates, are clamped into close contact with each other. Therefore, a body fluid such as bile will not leak out from between the intestinal wall Wd and the duct wall Wc into a body cavity through the hole We.

Figure 31:
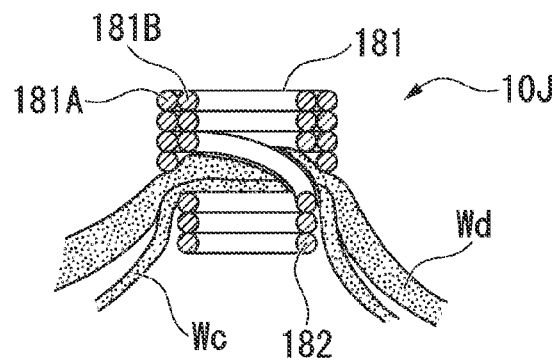

A tissue fastener 10J shown in FIG. 31 has a first tissue fixation portion 181 and a second tissue fixation portion 182, both of which are made of a highly elastic metal wire 10 wound in a coil (a cylinder). The first tissue fixation portion 181 has a large coil-shaped portion 181A formed of two-tier large and small coils, and a small coil-shaped portion 181B. The large coil-shaped portion 181A and the small coil-shaped portion 181B have their upper ends at the same height. However, at their lower ends, the large coil-shaped portion 181A stretches out over the small coil-shaped portion 181B. The second tissue fixation portion 182 has the same diameter as the small coil-shaped portion 181B so as to continue into the small coil-shaped portion. This tissue fastener 10J is the same in general shape as the one shown in FIG. 29A, 29B. The difference lies in the position at the tissue fastener is locked on the first tissue and the second biological tissue.

In this modification, when the tissue fastener is placed in living tissue, the intestinal wall Wd and the duct wall Wc are sandwiched between the small coil-shaped portion 181B of the first tissue fixation portion and the second tissue fixation portion 182, and also on the outer circumference side thereof, the lower end of the large coil-shaped portion 181 on the outer circumference side of the first tissue fixation portion 181 presses the intestinal wall Wd of the duodenum Dd in the downward direction in the figure. As a result, the intestinal wall Wd and the duct wall Wc are clamped into close contact with each other on the outer circumference side than the hole We formed when the piercing device 52 is piercingly inserted. Therefore, a body fluid such as bile will not leak out from between the intestinal wall Wd and the duct wall Wc into a body cavity through the hole We, similarly to the one shown in FIG. 30 described above.

Figure 32A:
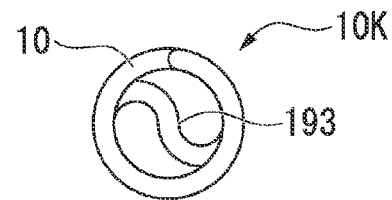
Figure 32B:
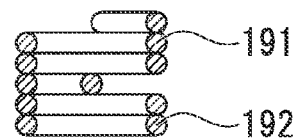

A tissue fastener 10K shown in FIGS. 32A, 32B has a first tissue fixation portion 191 and a second tissue fixation portion 192, both are made of a highly elastic metal wire 10 wound in a coil (a cylinder). A linking portion 193 for linking the first tissue fixation portion 191 and the second tissue fixation portion 192 is bent in an S shape so as to pass through a central portion between those coil-shaped portions.

Figure 33A:
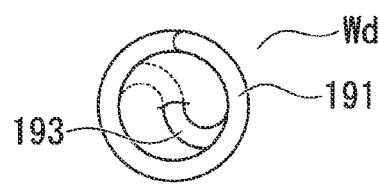
Figure 33B:
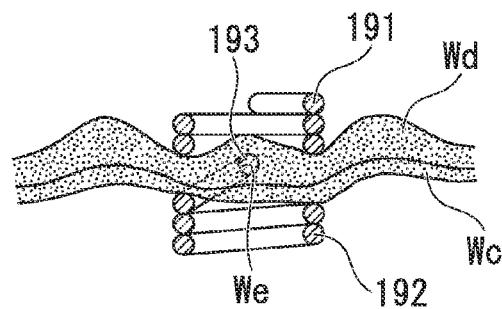

In this modification, when the tissue fastener is placed in a living body as shown in FIGS. 33A, 33B, the hole We formed when the piercing device 52 is piercingly inserted, that is, an area through a wire of the tissue fastener 10K penetrates is inside the intestinal wall Wd and duct wall Wc portions clamped by the first tissue fixation portion 191 and the second tissue fixation portion 192. As a result, the intestinal wall Wd and the duct wall Wc are clamped into close contact with each other on the outer circumference side than the hole We formed when the piercing device 52 is piercingly inserted. Therefore, a body fluid such as bile will not leak out from between the intestinal wall Wd and the duct wall Wc into a body cavity through the hole We, similarly to the ones shown in FIG. 30 and FIG. 31 described above.

Figure 34:
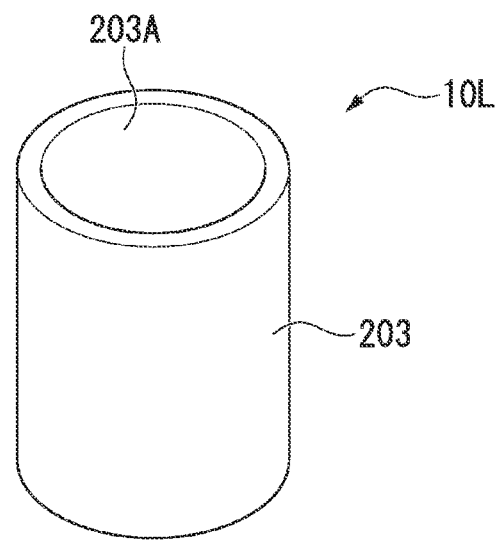
Figure 37:
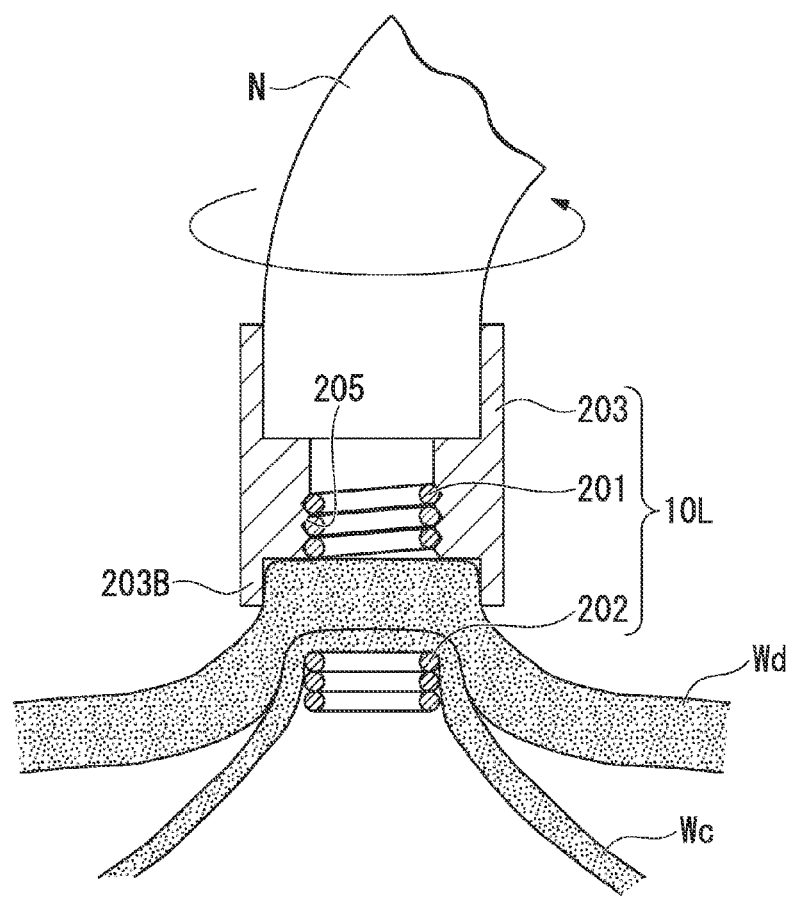

A tissue fastener 10L shown in FIG. 34 has: a first tissue fixation portion 201 and a second tissue fixation portion 202, both are made of a highly elastic metal wire wound in a coil (a cylinder); and a cap 203 (see FIG. 37). The cap 203 is formed in a cylindrical shape. An outer diameter thereof is set to be larger than that of the first tissue fixation portion 201 and the second tissue fixation portion 202. In a central portion of the cap 203, a small diameter portion 204 is formed. In an inner circumference thereof, a female thread portion 205 is formed to be fit onto the coil-shaped first tissue fixation portion 201. In the cap 203, an upper opening portion functions as a fitting portion 203A to be fit into a tip of an endoscope N, and a lower end portion functions as a ring-shaped stretching portion 203B that stretches toward the second tissue fixation portion 202 side when the lower end portion fits the female thread portion onto the first tissue fixation portion 201.

Figure 35:
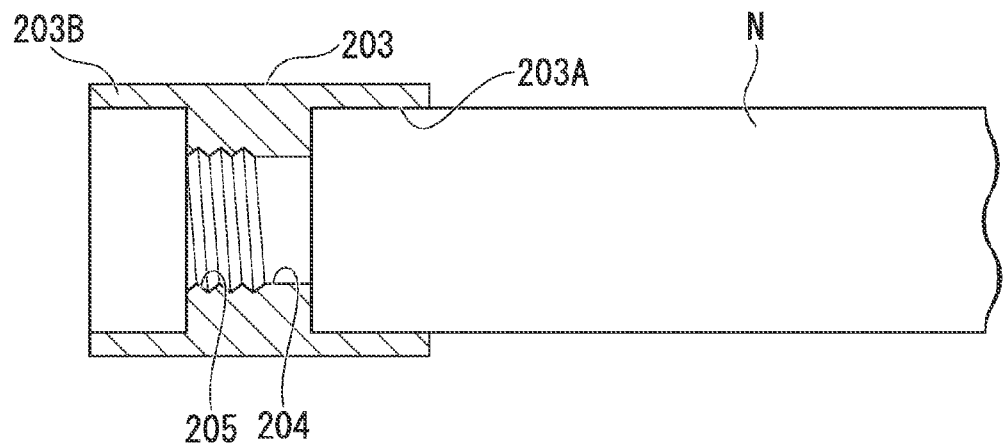
Figure 36:
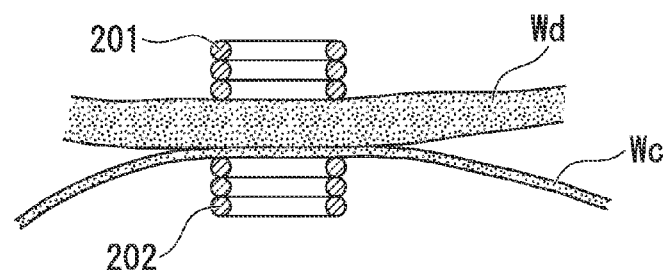

To place the tissue fastener 10L of this modification in a living body, the fitting portion 203A of the cap 203 is previously fitted onto the tip of the endoscope N, as shown in FIG. 35. Then, as shown in FIG. 36, the first tissue fixation portion 201 and the second tissue fixation portion 202 are placed in a living body so as to clamp the intestinal wall Wd and the duct wall Wc, as described in the above embodiment.

Next, the prepared endoscope N with the cap is inserted into the living body. Then, as shown in FIG. 37, the cap 203 fitted onto the tip is abutted against the first tissue fixation portion 201 while positioning the cap 203 so as to be coaxial with the first tissue fixation portion 201. In this condition, the cap 203 is rotated to screw the female thread portion 205 onto the first tissue fixation portion 201. At this time, the more the female thread portion 205 is screwed, the more the first tissue fixation portion 201 penetrates into the cap 203. As a result, the intestinal wall Wd and the duct wall Wc are drawn into the cap 203 side while being clamped by the first tissue fixation portion 201 and the second tissue fixation portion 202. Then, the outer circumference side of the portion of the intestinal wall W that is locked on by the first tissue fixation portion 201 is strongly pressed to the duct wall Wc side by the stretching portion 203B of the cap 203.

As a result, the intestinal wall Wd and the duct wall Wc are clamped into close contact with each other on the outer circumference side than the hole We formed when the piercing device is piercingly inserted. Therefore, a body fluid such as bile will not leak out from between the intestinal wall Wd and the duct wall Wc into a body cavity through the hole We.

Figure 38:
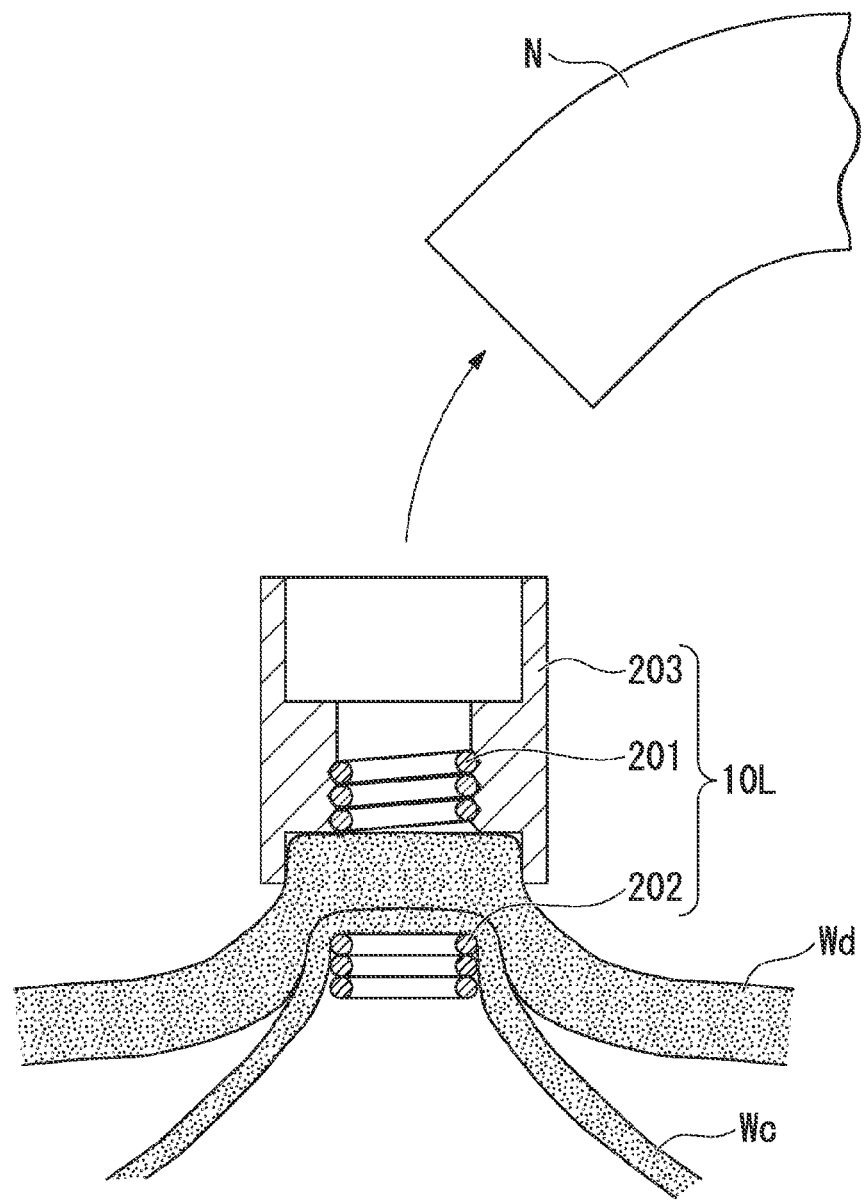
Figure 39A:
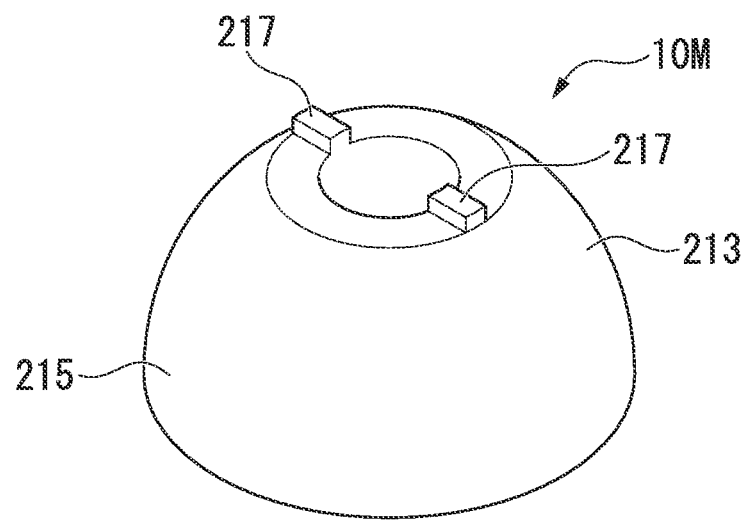
Figure 39B:
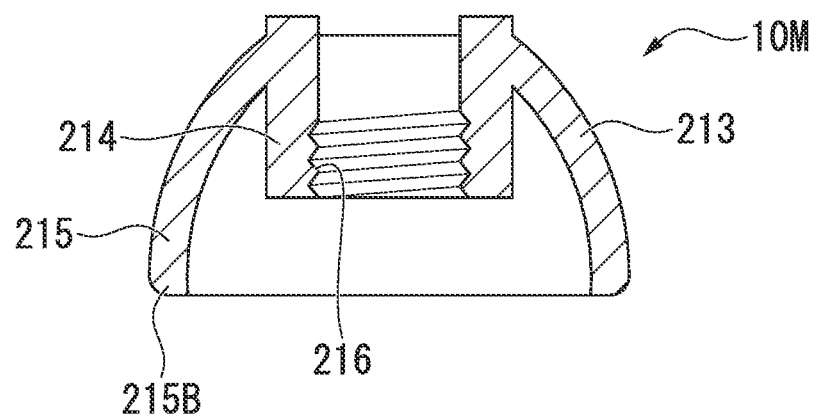
Figure 40:
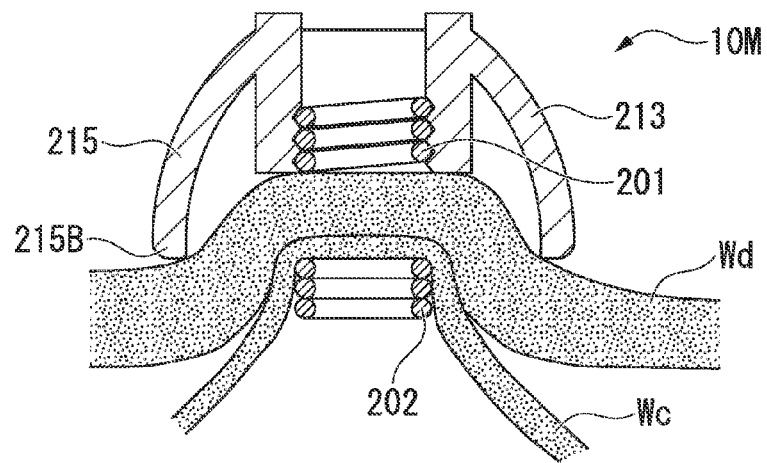
Figure 41:
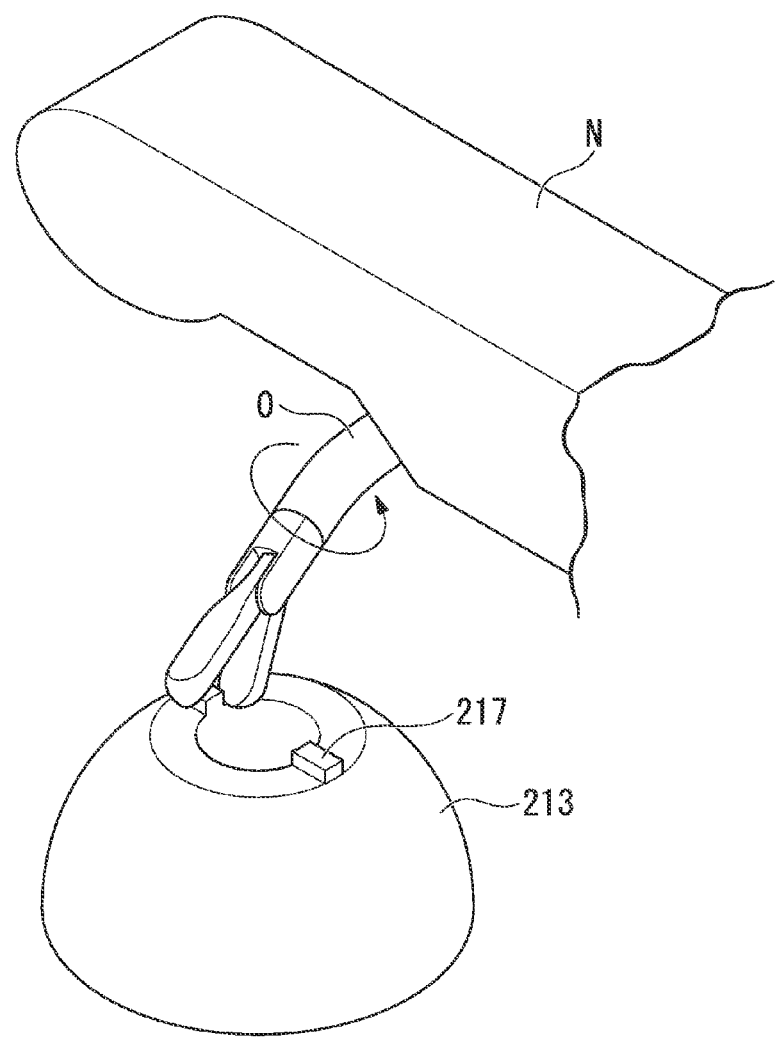

Note that after the cap 203 is screwed onto the first tissue fixation portion 201, the endoscope N is detached from the cap 203, and the endoscope N is pulled out with the cap 203 being placed in the living body, as shown in FIG. 38.

A tissue fastener 10M shown in FIG. 39A to FIG. 41 has: a first tissue fixation portion 201 and a second tissue fixation portion 202, both are made of a highly elastic metal wire 10 wound in a coil (a cylinder); and a cap 213. The cap 213 has: an internal barrel portion 214; and a hemisphere portion 215 that expands down from an upper portion of the internal barrel portion 214 while gradually extending outwardly. In an inner circumferential lower end portion of the internal barrel portion 214, a female thread portion 216 is formed. This female thread portion 216 fits onto the coil-shaped first tissue fixation portion 201. A lower end of the hemisphere portion 215 extends lower than a lower end of the internal barrel portion 214. Therefore, this lower end functions as a ring-shaped stretching portion 215B that outwardly stretches toward the second tissue fixation portion 202, when the female thread portion 214 is fitted onto the first tissue fixation portion 201. Furthermore, an upper portion of the hemisphere portion 213 is made flat. On this flat portion, knob portions 217 that extend in a straight line are formed.

This modification is the same as the one described above in that the first tissue fixation portion 201 and the second tissue fixation portion 202 are placed in a living body so as to clamp the intestinal wall Wd and the duct wall Wc.

Here, next, an endoscope is used to insert the cap 213 into the living body. The knob portions 217 of the cap 213 are held by straight grasping forceps O that are inserted into the living body via a channel of the endoscope The cap 213 is rotated while being positioned so as to be coaxial with the first tissue fixation portion 201, to thereby screw the female thread portion 216 onto the first tissue fixation portion 201. At this time, similarly to the above, the outer circumference side of the portion that is locked on by the first tissue fixation portion 201 of the intestinal wall W is strongly pressed to the duct wall Wc side by the stretching portion 215B of the cap 203. As a result, the intestinal wall Wd and the duct wall Wc which are clamped into close contact with each other on the outer circumference side than the hole We formed when the piercing device is piercingly inserted. As a result a body fluid such as bile will not leak out from between the intestinal wall Wd and the duct wall Wc into a body cavity through the hole We.

Figure 42:
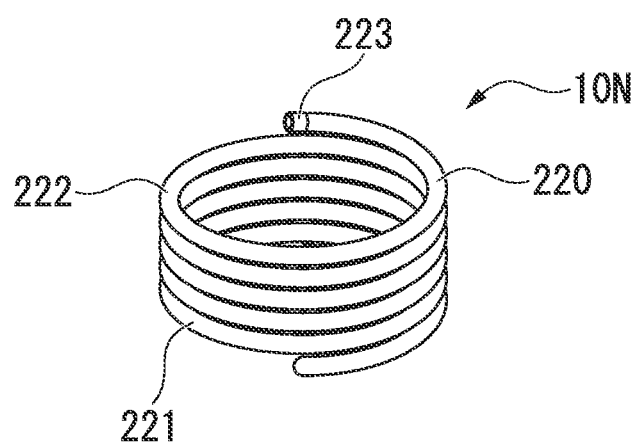

A tissue fastener 10N shown in FIG. 42 has a first tissue fixation portion 221 and a second tissue fixation portion 222, both are made of a highly elastic material 220 wound in a coil (a cylinder). Here, the highly elastic material 220 is tubular in shape, and an inner diameter thereof is set to be larger than an outer diameter of the piercing device 52 of the applicator. Furthermore, a tip portion of the highly elastic material 220 is formed into a tapered portion 223 that is gradually narrowed.

Figure 43:
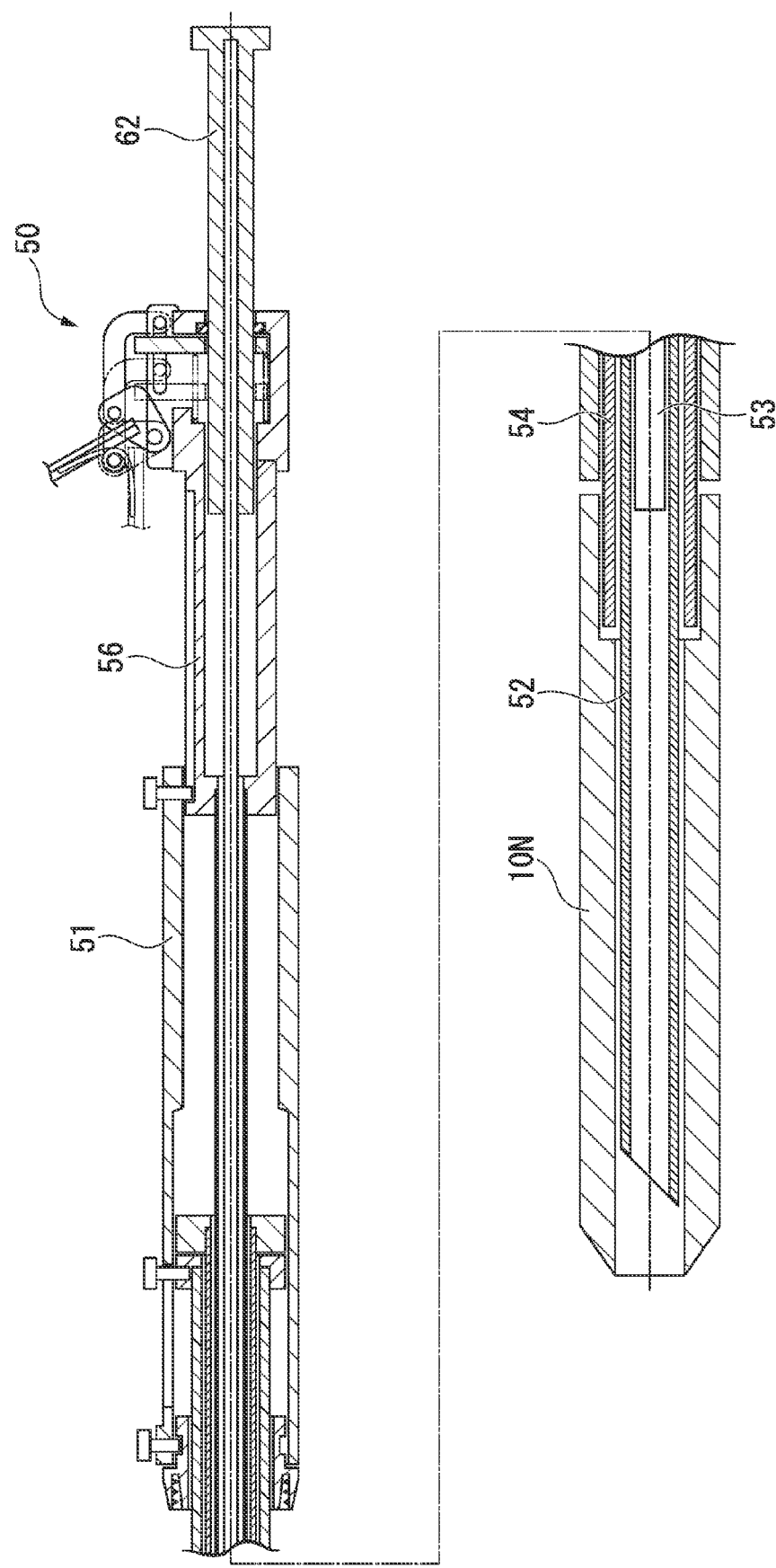
FIG. 43 to FIG. 48 show a procedure of placing the tissue fastener shown in FIG. 42.
Figure 44:
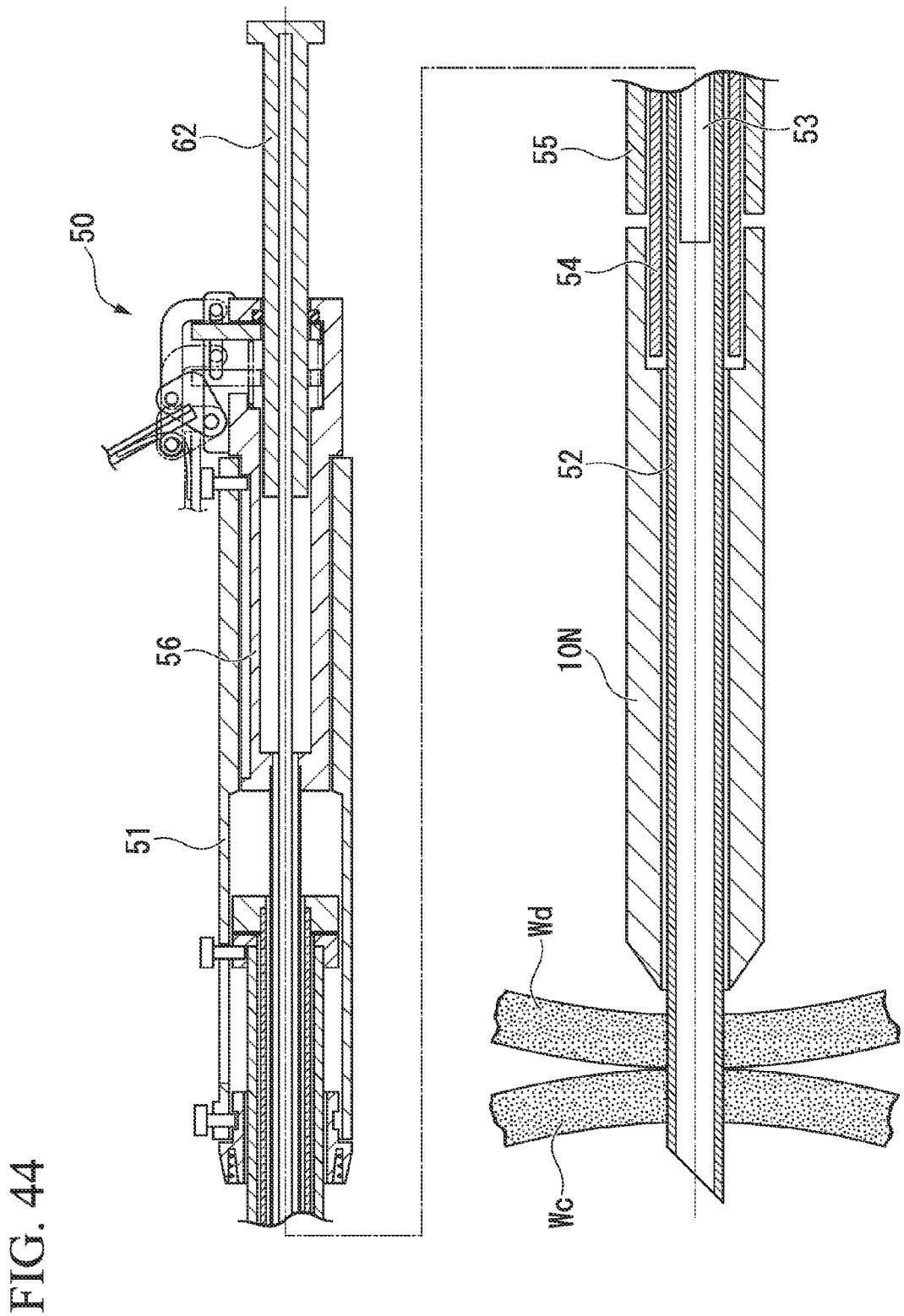
Figure 45:
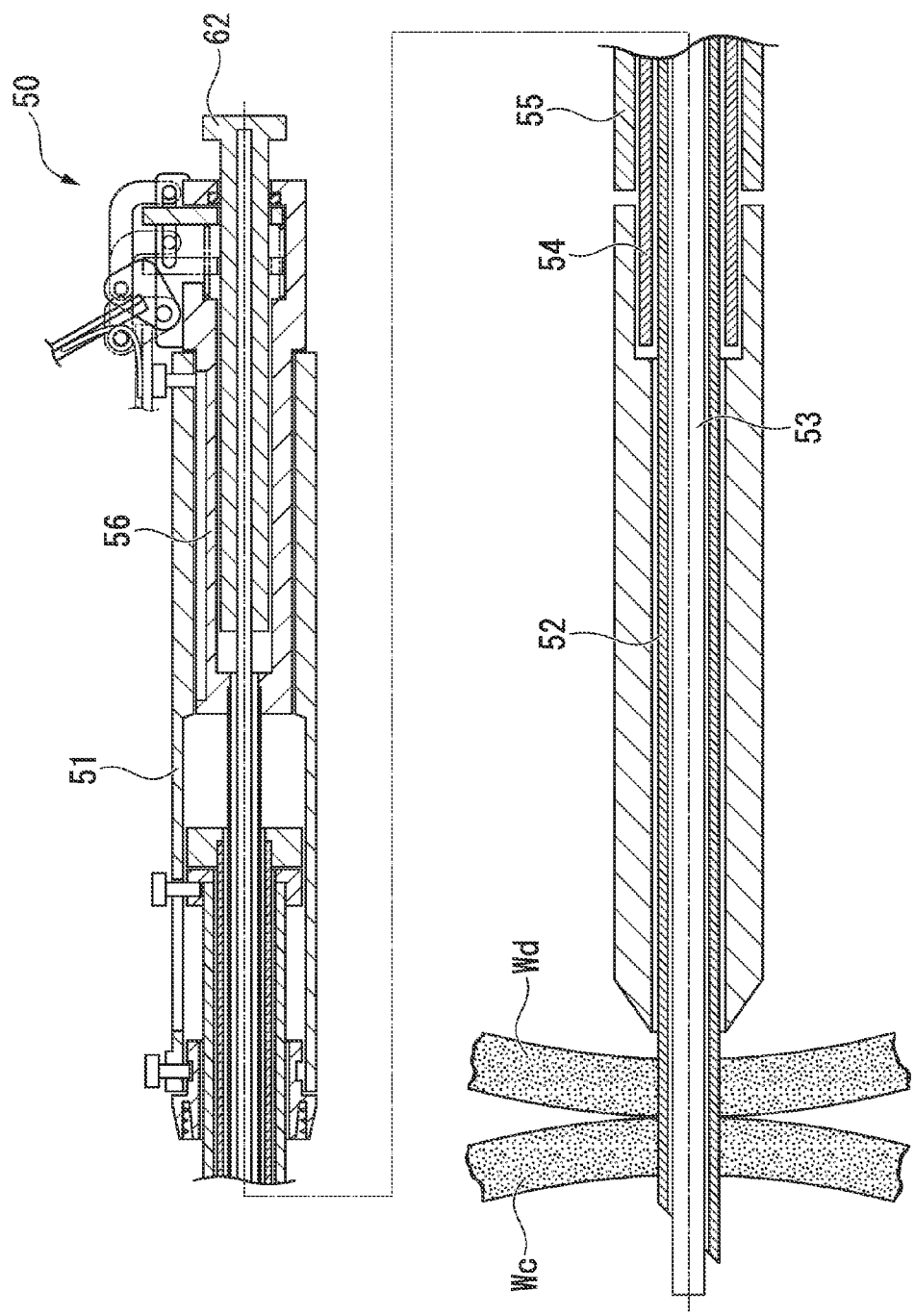

To place this tissue fastener 10N in a living body, the tissue fastener 10N is first arranged around an outer circumference of the piercing device 52, as shown in FIG. 43. At this time, a base end side of the tissue fastener 10N is previously fitted into a sheath 54 by friction. Next, as shown in FIG. 44, a piercing device operation portion 56 is moved forward to piercingly insert the piercing device 52 into first biological tissue and second biological tissue, here, into an intestinal wall Wd of a duodenum and a duct wall Wc of a common bile duct. Next, as shown in FIG. 45, a stylet 53 is moved forward to protrude past a tip of the piercing device 52.

Figure 46:
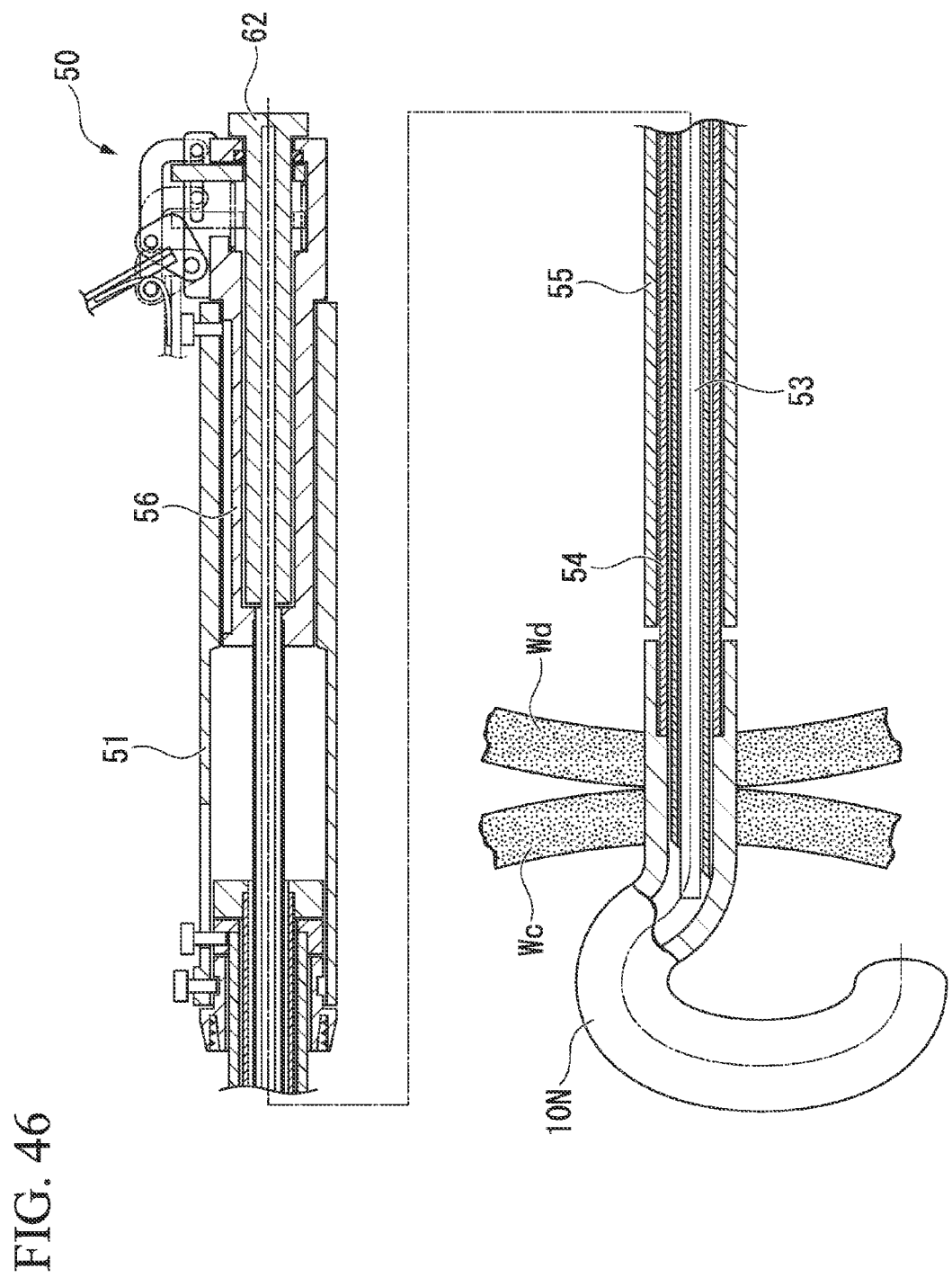
Figure 47:
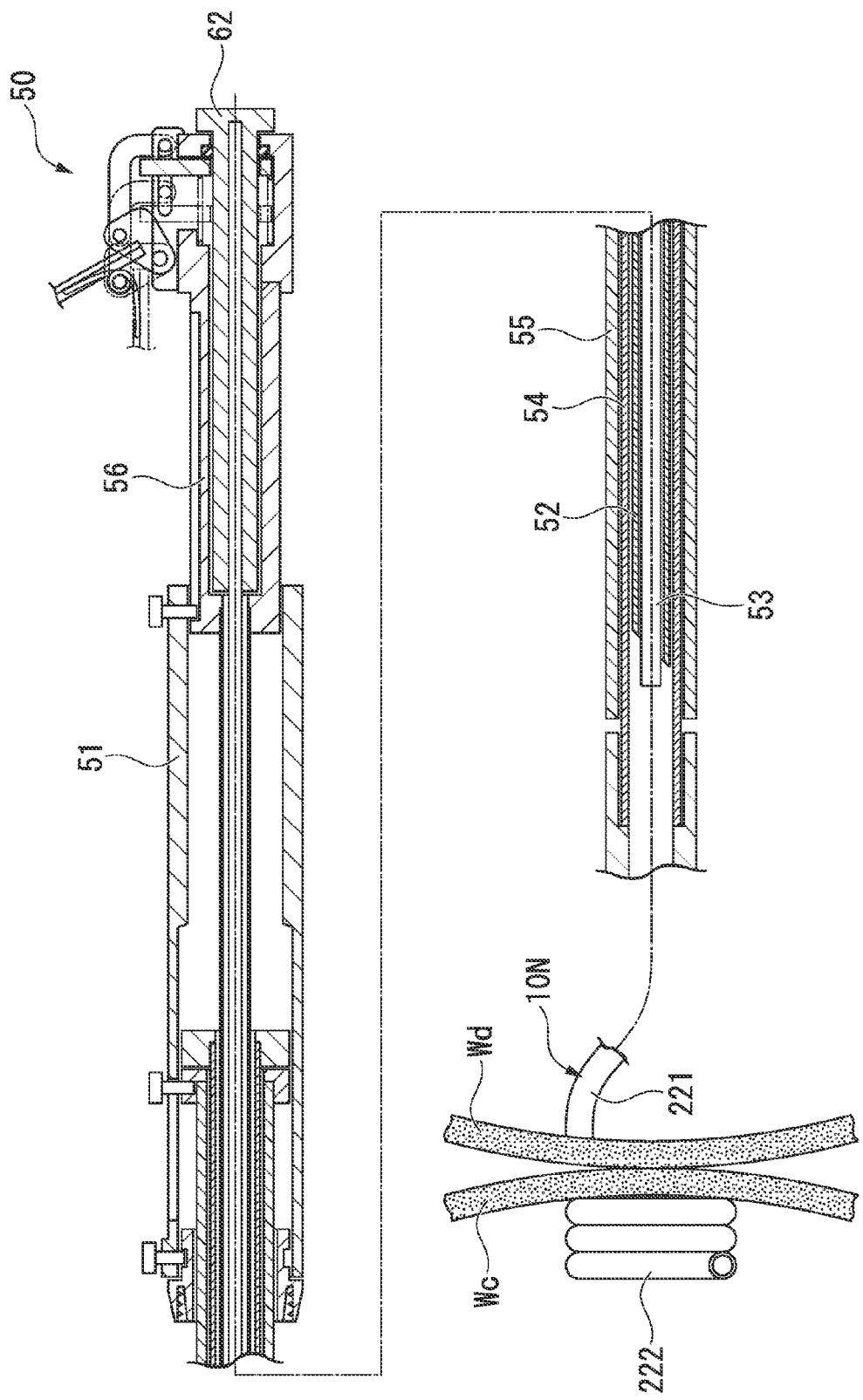
Figure 48:
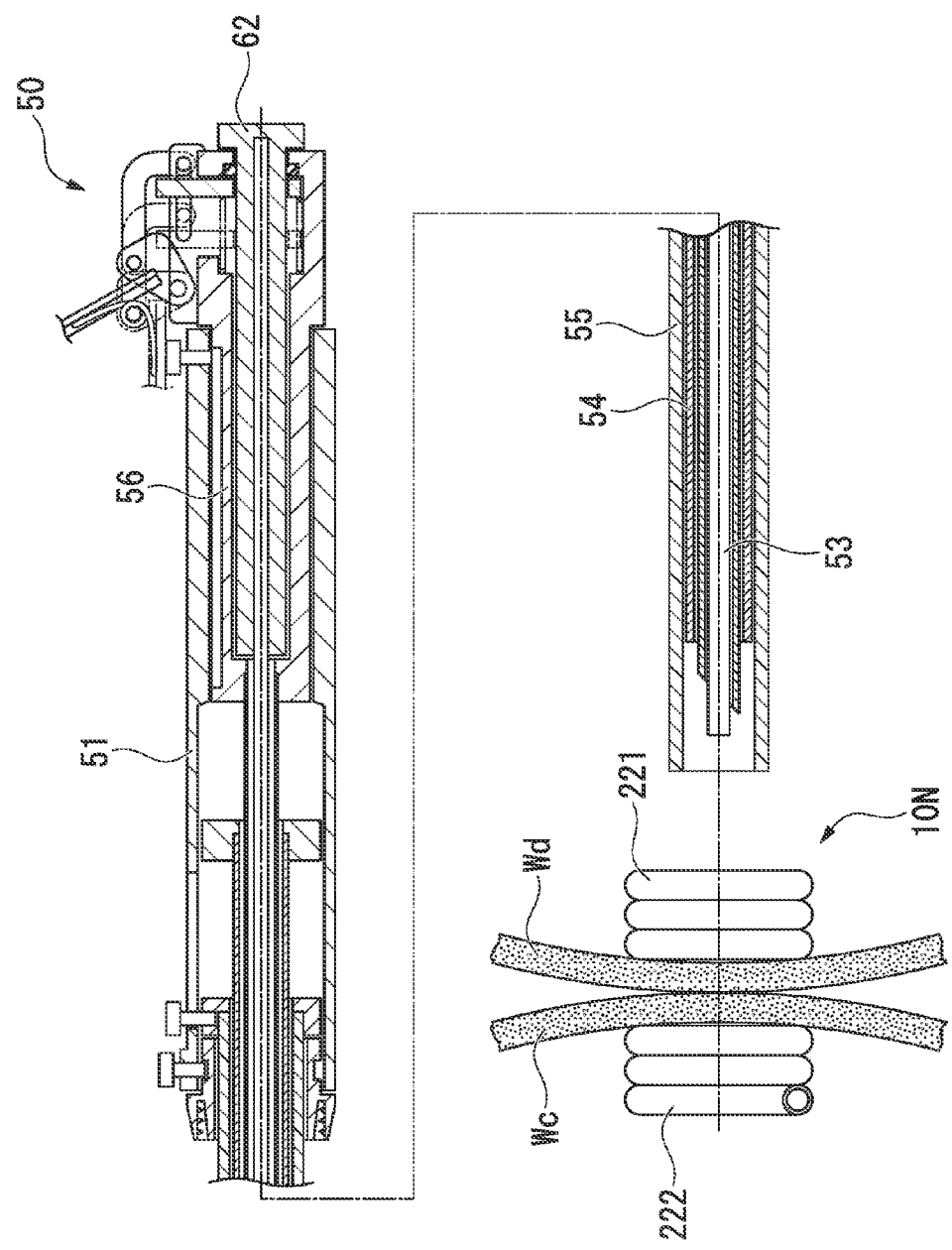

Next, as shown in FIG. 46, the sheath 54 and a pusher 55 are moved forward to place a part of the tissue fastener 10N in the duct wall Wc of the common bile duct. A portion of the tissue fastener 10N exposed in the common bile duct returns its original coil shape by its own elastic action, and is placed therein. Subsequently, as shown in FIG. 47, the piercing device 52 and the stylet 53 are pulled back from the first and the second biological tissue Wd to the hand side. Next, as shown in FIG. 48, the sheath 54 is moved backward to the hand side, to thereby separate the applicator from the tissue fastener 10N.

As a result, it is possible to place the tissue fastener 10N in the living body.

Here, the outer diameter of the tissue fastener 10N is larger than that of the piercing device, that is, larger than a hole We in the living tissue formed by the piercing device. Consequently, no gap is produced between the hole and the tissue fastener. Therefore, a body fluid will not leak out from the gap between the hole and the tissue Fastener.

In addition, the tissue fastener 10N is made of a tubular material. Therefore, it is possible to allow a body fluid such as bile to flow from the duct wall Wc side of the common bile duct to the intestinal wall Wd side of the duodenum through a lumen of the tubular material, without using a stent.

Figure 49:
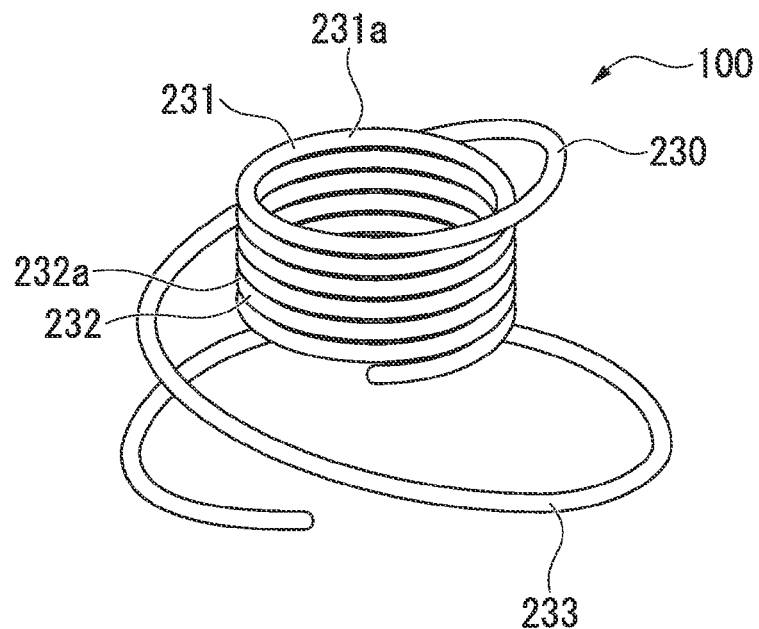
FIG. 49 to FIG. 63 show still other forms of a tissue fastener.

A tissue fastener 10O shown in FIG. 49 has a first tissue fixation portion 231 and a second tissue fixation portion 232, both of which are made of a highly elastic metal wire 230 wound in a coil (a cylinder). The first tissue fixation portion 231 and the second tissue fixation portion 232, in a state with the first tissue fixation portion 231 being locked on an intestinal wall Wd of a duodenum and the second fixation portion 232 being locked on a duct wall Wc of a common bile duct, clamp these intestinal wall Wd and duct wall Wc so as to be brought in close contact with each other. To be more specific, the first tissue fixation portion 231 is made of a first inner circumference spring portion 231a to be locked on the intestinal wall Wd of the duodenum, and the second tissue fixation portion 232 is made of a second inner circumference spring portion 232a to be locked on the duct wall Wc of the common bile duct. From a tip of the first inner circumference spring portion 231a, an outer circumference spring portion 233 is provided so as to extend outwardly in a radial direction and also to return to the second inner circumference spring portion 232a side to be locked on the intestinal wall Wd of the duodenum.

Figure 50:
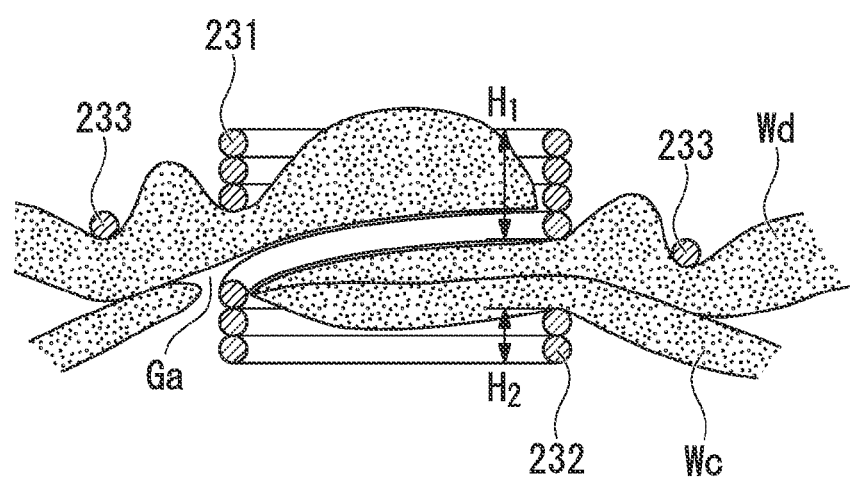

Furthermore, the inner circumference spring portions 231a, 232a are provided with an initial tension. This initial tension is set to a degree such that in placing the tissue fastener 10O in a living body, even if a tip of the outer circumference spring portion 233 presses the intestinal wall Wd downwardly and then receives a reaction force from there, the first inner circumference spring portion 231a is not pulled away from the intestinal wall Wd, and that no gap is produced between the portions of the highly elastic metal wire 230 as shown in FIG. 50. A description of this will be given later. Furthermore, a height H1 of the first inner circumference spring portion 231a and a height H2 of the second inner circumference spring portion 232a are set to heights such that when the tissue fastener 10O is placed in the living body, the two spring portions protrude past the living tissue as the placement target moves outwardly in an axial direction. For example, in the case of the first inner circumference spring portion 231a that is placed in the intestinal wall Wd of the duodenum, the height H1 is set to 1.5 mm or more. The duct wall Wc of the common bile duct is thinner than the intestinal wall Wd of the duodenum. Therefore, the height H2 of the second inner circumference spring portion 232a that is placed in the duct wall Wc of the common bile duct is 0.5 mm or more.

In the tissue fastener 10O with the above structure, as shown in FIG. 50, the first inner circumference spring portion 231a is locked on the intestinal wall Wd of the duodenum and the second inner circumference spring portion 232a is locked on the duct wall Wc of the common bile duct. Thereby, the intestinal wall Wd and the duct wall Wc are clamped so as to be brought in close contact with each other by those inner circumference spring portions 231a, 232a. Furthermore, the outer circumference spring portion 233 presses the intestinal wall Wd of the duodenum to the duct wall Wc side of the common bile duct.

Figure 51:
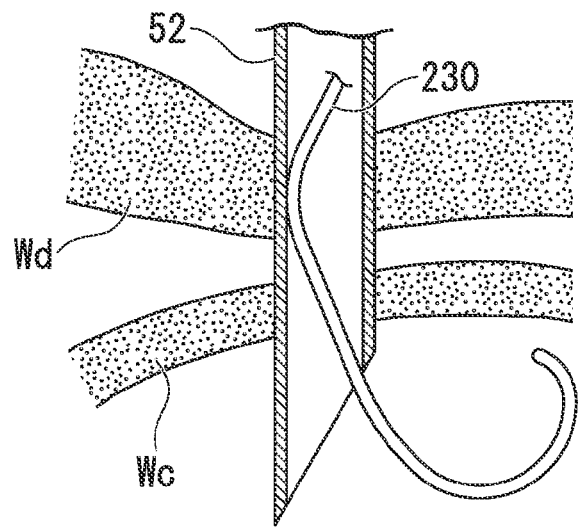
Figure 52:
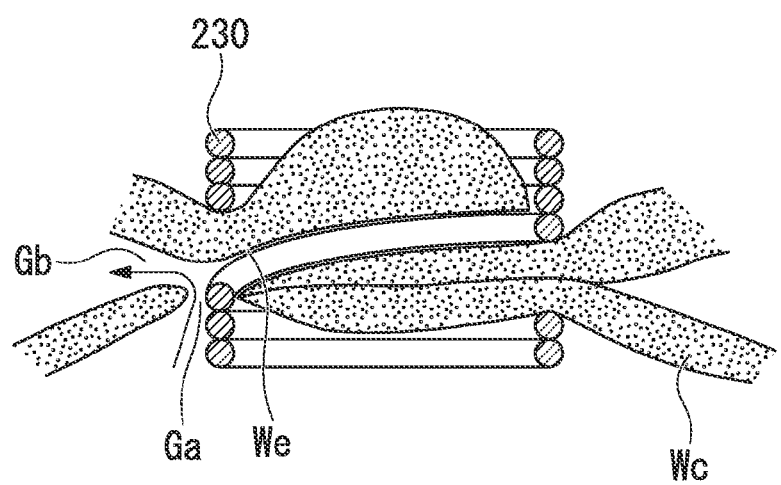

Here, the case without the outer circumference spring portion 233 will be described. When the tissue fastener is placed in a living body, the highly elastic metal wire 230 is previously inserted and set in the piercing device 52 in an extended manner, as shown in FIG. 51. This piercing device 52 is then piercingly inserted into the intestinal wall Wd of duodenum and the duct wall Wc of the common bile duct, and the highly elastic metal wire 230 is pushed out from a tip thereof to place the tissue fastener. As a result, a gap Ga is formed between the hole We formed in the duct wall Wc of the common bile duct when the piercing device 52 is piercingly inserted and the highly elastic metal wire 230 is penetrated and arranged through this hole We. Therefore, there arises a phenomenon in which a body fluid such as bile flows out through this gap Ga, and furthermore flows through a gap Gb between the intestinal wall Wd of the duodenum and the duct wall Wc of the common bile duct, to thereby leak into an abdominal cavity. If the body fluid is bile, there is a possibility of producing bile peritonitis.

However, in this modification, the outer circumference side of the portion of the intestinal wall Wd of the duodenum clamped by the first and second inner circumference spring portions 231a, 232a is pressed to the duct wall Wc side of the common bile duct by the outer circumference spring portion 233, as shown in FIG. 50. Therefore, no gap is produced between the intestinal wall Wd of the duodenum and the duct wall Wc of the common bile duct. As a result, even if a body fluid such as bile leaks out through the gap Ga, this body fluid will not leak into an abdominal cavity through the gap between the intestinal wall Wd of the duodenum and the duct wall Wc of the common bile duct.

Furthermore, the insides of the portions of the intestinal wall Wd of the duodenum and the duct wall Wc of the common bile duct clamped by the inner circumference spring portions 231a, 232a have a flow of blood prevented and develops pressure necrosis. At the same time, around the inner circumference spring portions, the intestinal wall Wd and the duct wall Wc are adhered and joined. Then, the tissue fastener and the necrotized tissue fall off from the other tissue. At this time, the inner circumference spring portions 231a, 232a are always biased to a duodenal lumen side by the outer circumference spring portion 233. Therefore, when the tissue fastener falls off, the tissue fastener inevitably falls off to the lumen side of the duodenum. As a result, the tissue fastener is promptly excreted out of the body through the small intestine and the large intestine.

Figure 53:
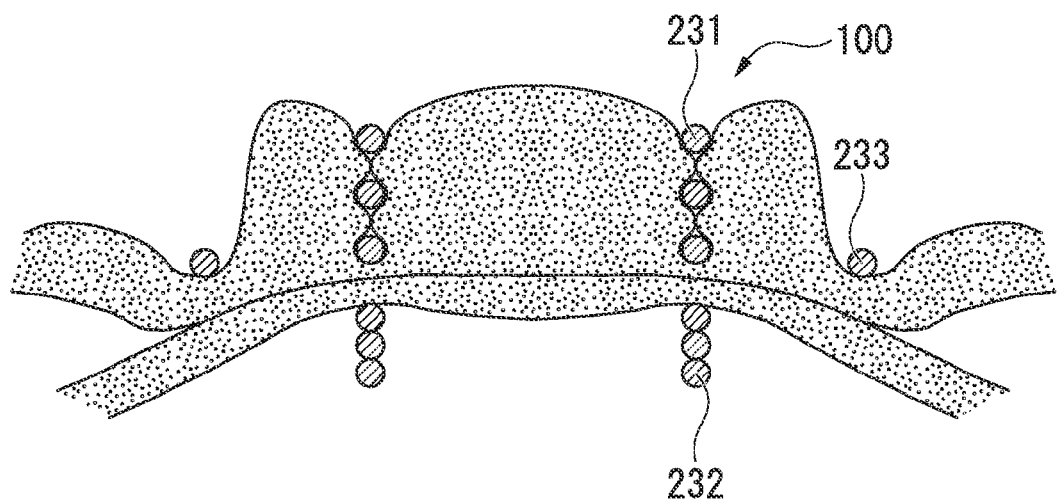

As described above, the outer circumference spring portion 233 presses the intestinal wall Wd of the duodenum to the duct wall Wc side of the common bile duct. The reactive force at that time also functions as force to separate the first inner circumference spring portion 231a from the intestinal wall Wd. Therefore, if an initial tension of the inner circumference spring portion is smaller than a biasing force of the outer circumference spring portion, a clamping force between the first inner circumference spring portion 231a and the second inner circumference spring portion 232a is weakened, and also a gap is produced between the portions of the highly elastic metal wire 230 of the first inner circumference spring portion 231a, as shown in FIG. 53.

In this manner, if the force generated between the inner circumference spring portions 231a, 232a for clamping the intestinal wall Wd and the duct wall Wc is weakened, it is not possible to sufficiently prevent a flow of blood in the intestinal wall Wd and the duct wall Wc. Furthermore, if a gap is produced between the portions of the highly elastic metal wire 230 constituting the inner circumference spring portion, tissue surrounded by the inner circumference spring portion is brought into contact with tissue outside thereof through the gap between the portions of the highly elastic metal wire 230, allowing a flow of blood to occur between the two. It follows that the tissue surrounded by the inner circumference spring portion will not be necrotized. Therefore, the tissue will not fall off, and it is not possible to form a subsequent healed hole.

In this modification, the initial tension of the inner circumference spring portion, especially of the first inner circumference spring portion, is set to a degree such that in placing the tissue fastener 10O in a living body, even if a tip of the outer circumference spring portion 233 presses the intestinal wall Wd downwardly and then receives a reaction force from there, the first inner circumference spring portion 231a is not pulled away from the intestinal wall Wd, and that no gap is produced between the portions of the highly elastic metal wire 230, as shown in FIG. 50. Therefore, when the tissue fastener is placed, no gap is produced between the portions of the highly elastic metal wire 230 of the inner circumference spring portion, and hence it is possible to maintain the close contact condition. As a result, a flow of blood is prevented between the tissue surrounded by the inner circumference spring portions 231a, 232a and the outside tissue, and then the tissue surrounded by the inner circumference spring portions 231a, 232a is necrotized. Subsequently, the tissue fastener and the necrotized tissue fall off, and a healed hole for communicating the intestinal wall Wd of the duodenum and the duct wall We of the common bile duct is formed.

Figure 54:
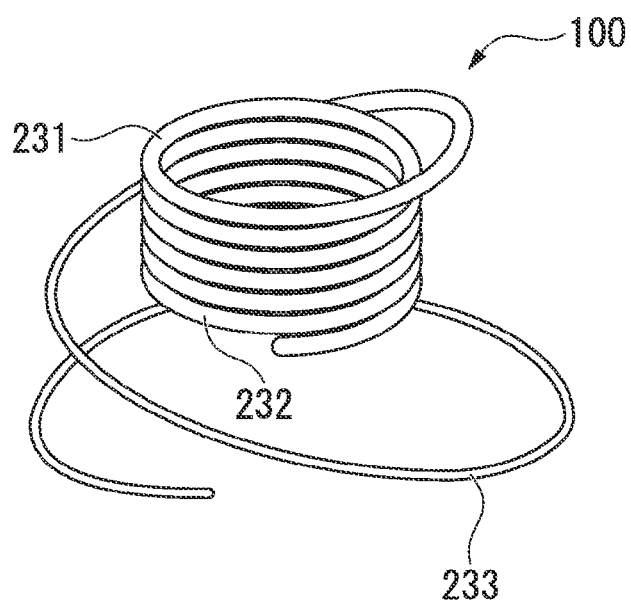

In this modification, the initial tension of the inner circumference spring portions 231a, 232a is increased. It is set to a degree such that when the tissue fastener is placed, the first inner circumference spring portion 231a is not separated from the intestinal wall Wd and that no gap is produced between the portions of the highly elastic metal wire 230. However, the structure is not limited to this. As shown in FIG. 54, a wire diameter of a highly elastic metal wire constituting an outer circumference spring portion 233 is set to be smaller than a wire diameter of a highly elastic metal wire constituting an inner circumference spring portion, to thereby make it possible to weaken a reactive force generated by the outer circumference spring portion 233. Therefore, it is possible to produce an effect similar to the one as described above.

On the other hand, if the heights of the second inner circumference spring portions 231a, 232a are too low, a flow of blood may be maintained as a result of the tissue surrounded by those first and second inner circumference spring portions 231a, 232a being brought into contact with the outside tissue through an upper side portion of the inner circumference spring portion. If the flow of blood is maintained, the tissue surrounded by the inner circumference spring portion will not be necrotized, and hence will not fall off.

However, in this modification, the heights H1, H2 of the first and second inner circumference spring portions 231a, 232a are set to heights such that when the tissue fastener 10O is placed in the living body, the two portions protrude past the living tissue as the placement target outwardly. For example, in the case of the first inner circumference spring portion 231a being placed in the intestinal wall Wd of the duodenum, the height H1 is 1.5 mm or more. In addition, because the duct wall Wc of the common bile duct is thinner than the intestinal wall Wd of the duodenum, the height H2 of the second inner circumference spring portion 232a placed in the duct wall Wc of the common bile duct is 0.5 mm or more. As a result, when the tissue fastener is placed, it is possible to prevent a flow of blood between the tissue surrounded by those first and second inner circumference spring portions 231a, 232a and the outside tissue. Therefore, it is possible to necrotize the tissue surrounded by the inner circumference spring portion and to let it fall off.

Figure 55:
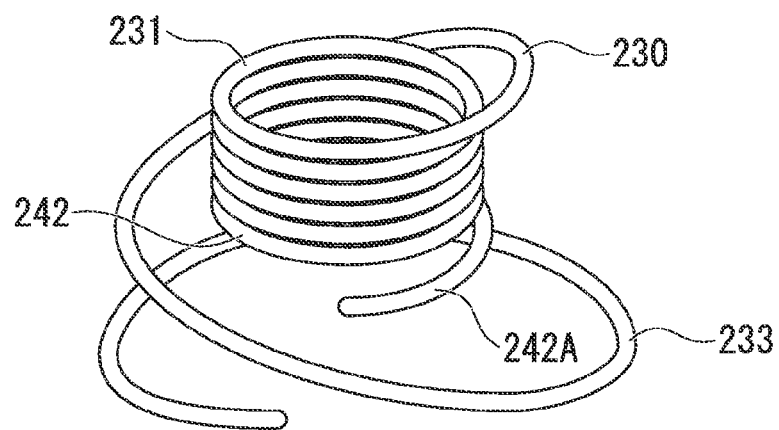

A tissue fastener 10P shown in FIG. 55 has a first tissue fixation portion (first inner circumference spring portion) 231 and a second tissue fixation portion (second inner circumference spring portion) 242, both of which are made of a highly elastic metal wire 230 wound in a coil (a cylinder), and furthermore has an outer circumference spring portion 233 that extends from a tip of the first inner circumference spring portion outwardly in a radial direction. In this point, this modification is similar to the modification described above.

In this modification, a tip portion of the second inner circumference spring portion 242, for example substantially one turn 242A is not closely wound but is wound so as to be spaced apart from the other portions.

Figure 56:
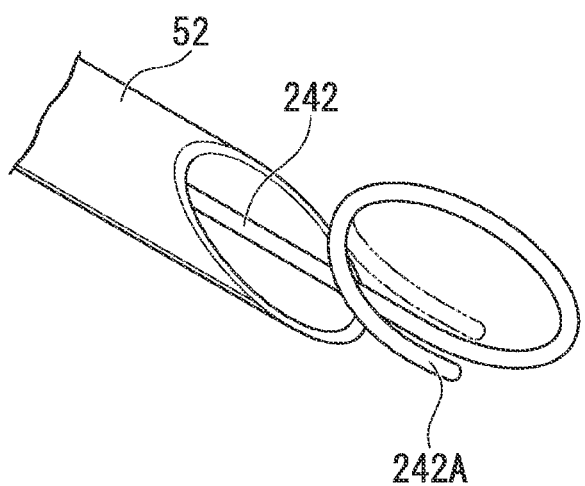

Incidentally, the first and second inner circumference spring portions are provided with an initial tension, and hence are not capable of shrinking any more. In the case where the second inner circumference spring portion is closely wound to its tip, when for example the inner circumference spring portion of a right wound coil is pushed out from the piercing device 52, the inner circumference spring portion assumes its original right wound coil shape as shown in FIG. 56, if the coil is not provided with an initial tension. However, if the inner circumference spring portion is provided with an initial tension, the coil tries to shrink. Therefore, its tip may be wound on the opposite side (on the left wound side), as shown by a double-dot line in FIG. 56. Once this occurs, the inner circumference spring portion, when pushed out from the piercing device, is forced to be of a left wound shape, although it is originally of a right wound shape. Such a situation is not preferable because the inner circumference spring portion will not assume its original coil shape, and hence will be incapable of exerting an expected biasing force.

In this modification, a tip portion of the second inner circumference spring portion 242, for example the substantially one turn 242A is not closely wound but is wound so as to be spaced apart from the other portions. Therefore, when the second inner circumference spring portion 242 is pushed out from the piercing device, no extra force acts on the one turn of the inner circumference spring portion, and hence the one turn is wound in its original shape. If the first portion is wound in its original coil shape, the subsequent portion is followingly wound in its original coil shape even if a strong initial tension is provided.

Note that the above modification is configured such that the tip portion 242A of the second inner circumference spring portion 242 is not closely wound but is wound so as to be spaced apart from the other portions. However, the structure is not limited to this. It may be configured such that a tip portion, for example substantially one turn portion 242A on the tip side, of the second inner circumference spring portion 242 is not provided with an initial tension, or is provided with a weaker initial tension than that of the other portions.

Figure 57A:
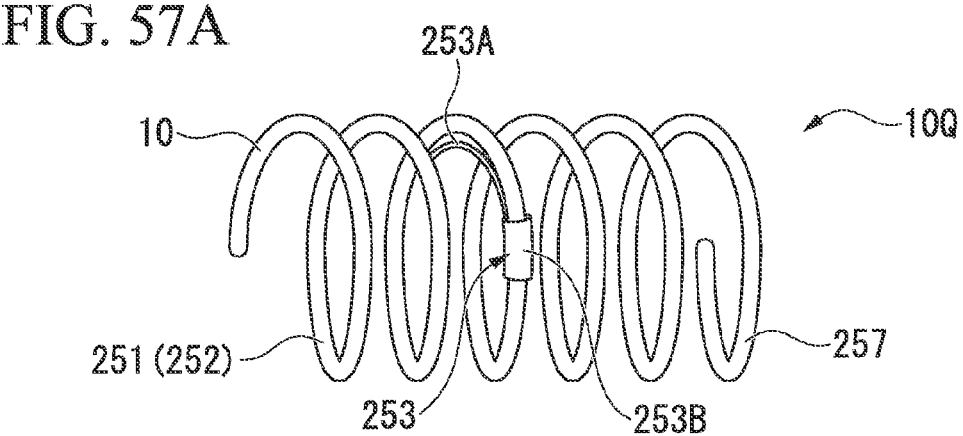
Figure 57B:
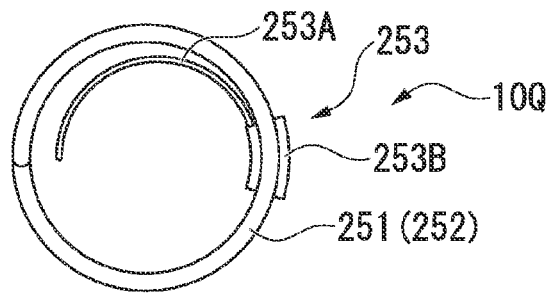

A tissue fastener 10Q shown in FIGS. 57A, 57B is provided with a stopper 253 between a first tissue fixation portion 251 and a second tissue fixation portion 252, aside from its main unit (that is, a highly elastic metal wire 10). A thin wire 253A with a diameter smaller than that of the wire 10 in a linking portion is inserted into a tube member 253B which is fitted onto the wire 10. Thereby, the stopper 253 is attached while being curved in a coil so as to be positioned inside the first and second tissue fixation portions 251, 252.

Figure 58:
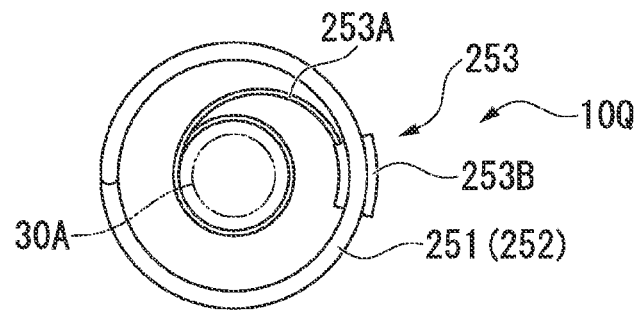
Figure 59:
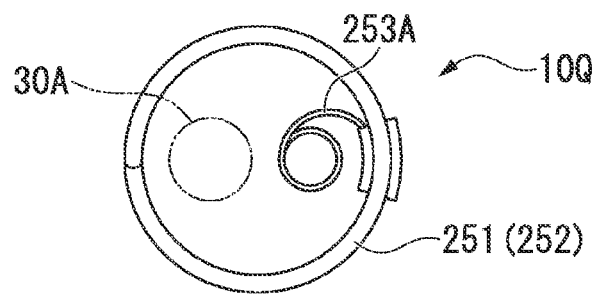

As a precondition, a diameter of the thin wire 253A at its curved portions is made smaller than an inner diameter of the coils of the first and second tissue fixation portions 251, 252. In addition, for placing a stent 30A, it is set to be larger than an outer diameter of the stent 30A, as shown in FIG. 58. Alternatively, it is set as small as possible, as shown in FIG. 59. In the latter case, this is for securing a sufficient space for placing the stent 30A between the thin wire 253A and the first and second tissue fixation portions 251, 252.

The stopper 253 is one that is locked on an intestinal wall Wd of a duodenum Dd to prevent a phenomenon where a tissue fastener 10B is pulled inside a common bile duct Cb, thus resulting in placement with an imbalance in number of coil turns between the first tissue fixation portion 251 locked on the intestinal wall Wd side of the duodenum Dd and the second tissue fixation portion 252 locked on the duct wall of the common bile duct.

As methods of fixing the thin wire 253A onto the highly elastic metal wire 10 in the linking portion between the first tissue fixation portion 251 and the second tissue fixation portion 252, the following can be listed.

Figure 60:
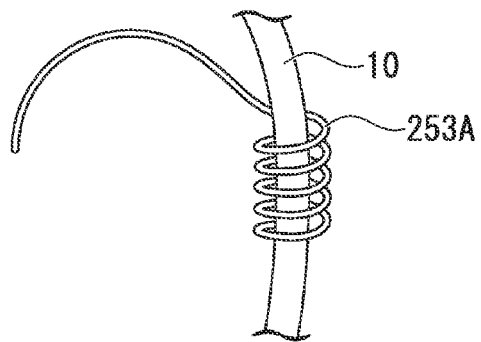
Figure 61:
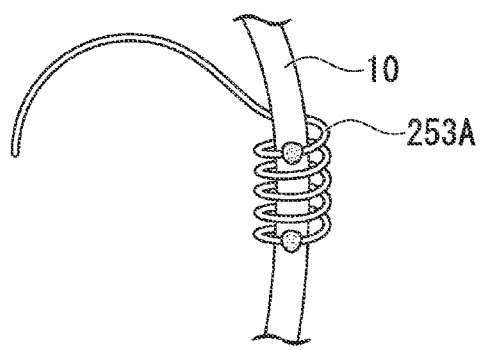
Figure 62:
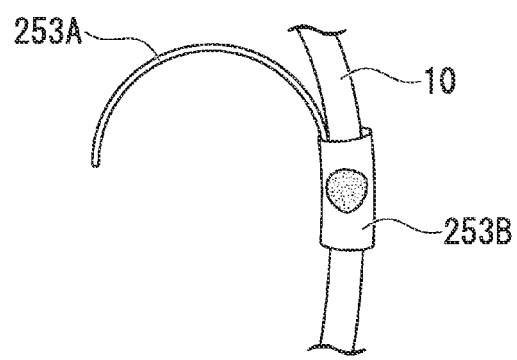
Figure 63:
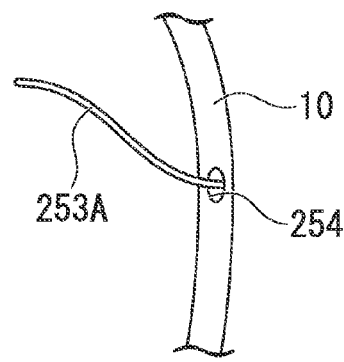

A method of winding the thin wire 253A around an outer circumference of the highly elastic metal wire 10 for fixation by friction, as shown in FIG. 60; a method of winding the thin wire 253A and welding the entire region or a plurality of points thereof as shown in FIG. 61; a method of utilizing the tube member 253B that is fitted onto the highly elastic metal wire 10, in which the tip of the thin wire 253A is inserted into the tube member 253B, and an adhesive is used or the tube member 253B is subjected to plastic deformation such as caulking for fixation, as shown in FIG. 62; and a method in which a hole 254 is bored in the highly elastic metal wire 10, and an end of the thin wire 253A is inserted into this hole to be fixed by known means such as an adhesive or caulking, as shown in FIG. 63 can be listed.

Figure 64:
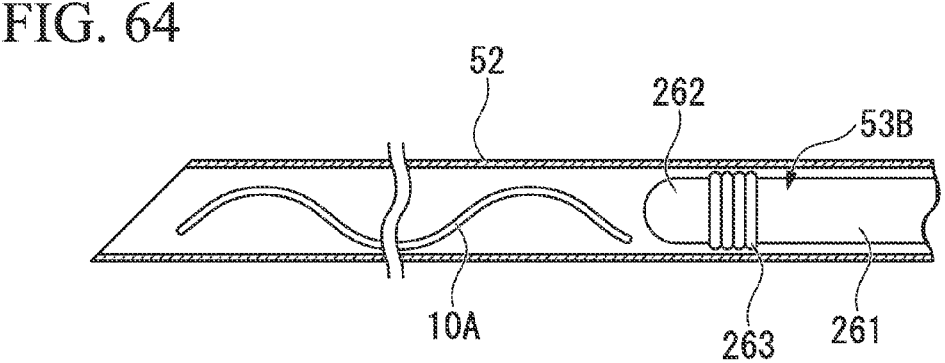

FIG. 64 shows a modification of a stylet of the applicator. A stylet, when inserted into a piercing device 2, originally has a function of pushing out a tissue fastener 10A at a tip of the piercing device 2 from the tip.

In a stylet 53B shown here, a hemispheric protrusion 262 is provided on a tip of a bar member 261, and an elastic coil 263 capable of expanding its diameter is wound around a small diameter portion 261A of the bar member 261 on a side closer to a base end than the protrusion. Furthermore, the elastic coil 263 functions as an electrode. It is configured such that to this electrode, high-frequency current is supplied from a power source (not shown in the figure) as required.

Figure 65:
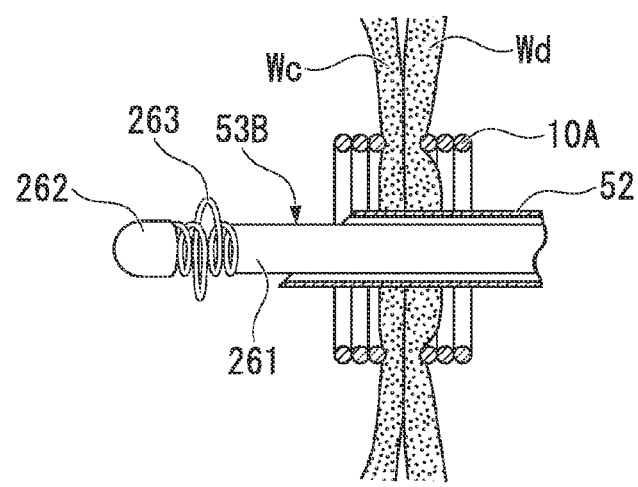
Figure 66:
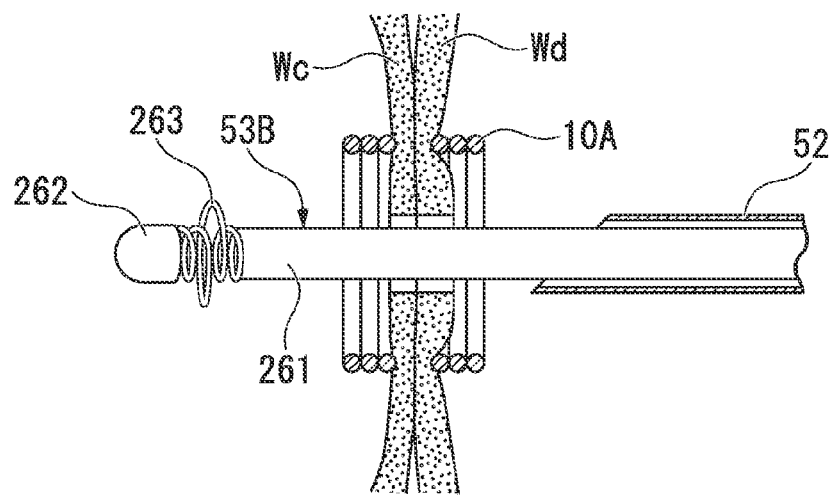
Figure 67:
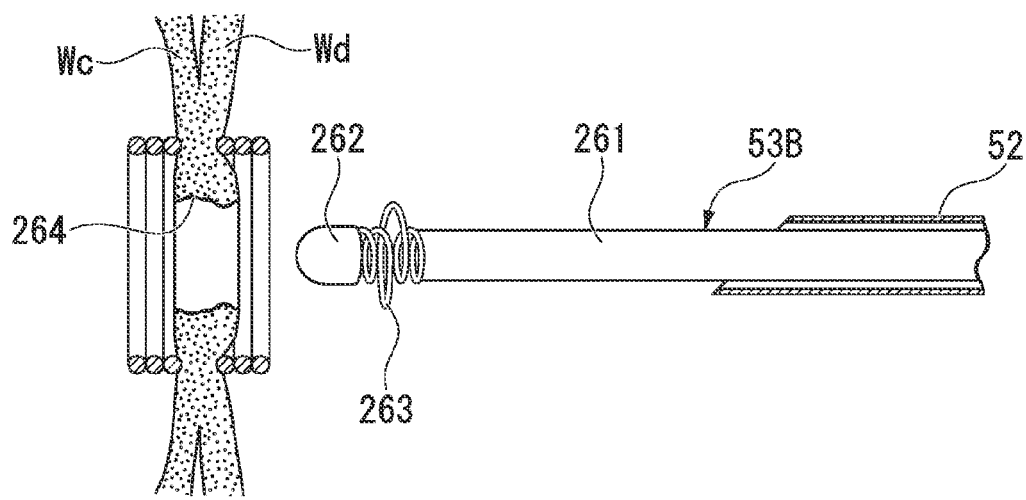

According to the stylet 53B with such a structure, forward movement causes a tissue fastener 10A inserted into the piercing device 52 to be pushed out. After that, as shown in FIG. 65, the protrusion 262 on the tip and the elastic coil 263 is protruded from the tip of the piercing device 52. At this time, the elastic coil 263 is expanded in diameter by its own elasticity. Then, in this condition, high-frequency current is supplied to the elastic coil 263 expanded in diameter. In this condition, the stylet 53B is pulled back to the hand side as shown in FIG. 66 and FIG. 67. Thereby, it is possible to burn off the intestinal wall Wd of the duodenum and the duct wall We of the common bile duct, which are clamped by the tissue fastener 10A, to form a drainage hole 264.

Figure 68:
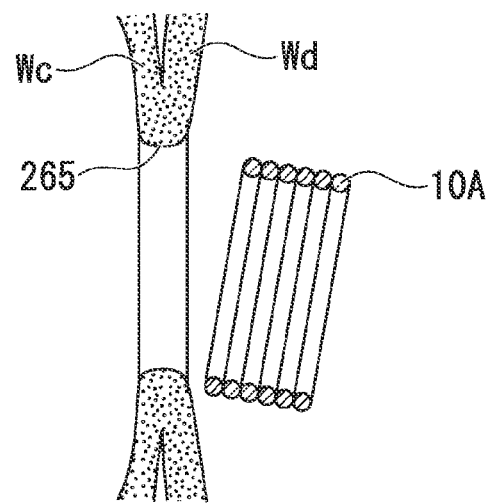

After that, as described above, the tissue fastener 10A falls off after the necrosis of the tissue, to thereby form an anastomotic fistula 265 as shown in FIG. 68.

Figure 69:
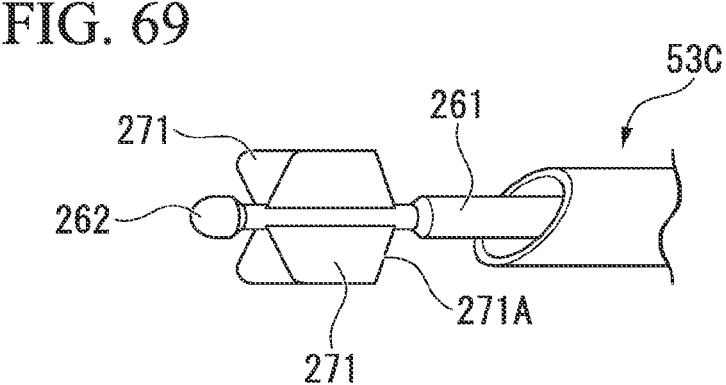
Figure 70:
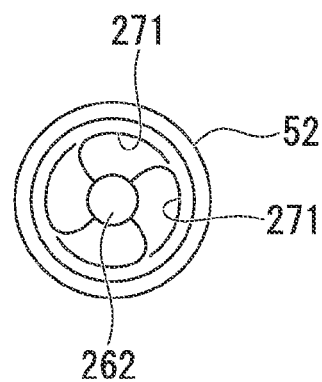

In a stylet 53C shown in FIG. 69, a hemispheric protrusion 262 is provided on a tip of a bar member 261, and cutting blades 271 are provided on the bar member 261 on a side closer to a base end than the protrusion. In a rear portion of each cutting blade 271, a blade portion 271A is provided in an inclined manner. Furthermore, the cutting blades 271 are elastic enough to be retractable in a piercing device 52 in a vortex manner seen from the front, as shown in FIG. 70.

According to the stylet 53C with the above structure, when the cutting blades 271 are protruded forward from the tip of the piercing device 52 as shown in FIG. 71 after the tissue fastener 10A inserted into the piercing device 52 is pushed out, the cutting blades 271 extend in a flat plate shape by their own elasticity. Then, they are pulled back to the hand side in this condition. As a result, it is possible to cut in the intestinal wall Wd of the duodenum and the duct wall We of the common bile duct with the blade portions 271A in the rear portion, to thereby form a drainage hole 273.

It is not configured such that high-frequency current is supplied to these cutting blades 271. However, it may be configured such that high-frequency current is supplied as required.

Figure 73:
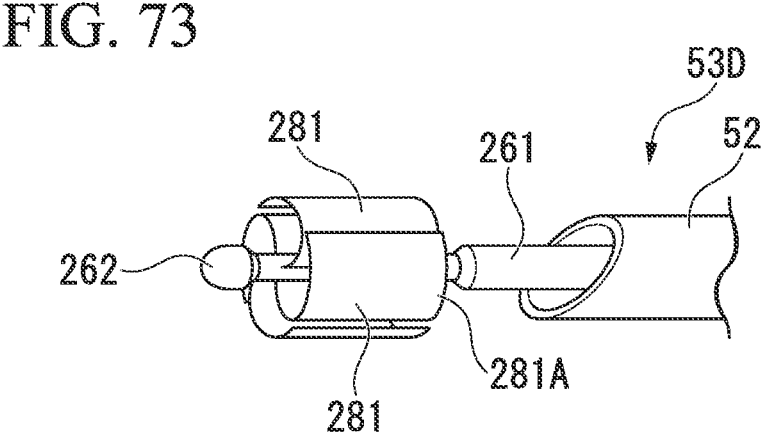
Figure 74:
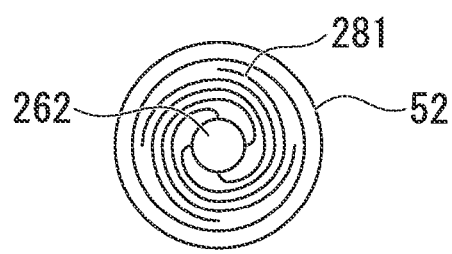
Figure 75:
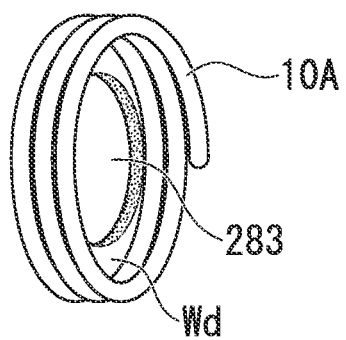

In a stylet 53D shown in FIG. 73, a hemispheric protrusion 262 is provided on a tip of a bar member 261, and cutting blades 281 are provided on the bar member 261 on a side closer to a base end than the protrusion. The cutting blades 281 are curved in an arc shape. It is configured such that the outlines thereof draw a circle as a whole. In a rear portion of each blade, a blade portion 281A is provided in an obliquely inclined manner. Furthermore, the cutting blades 281 are elastic enough to be retractable in a piercing device 52 in a vortex manner seen from the front, as shown in FIG. 74.

According to the stylet 53D with the above structure, when the cutting blades 281 are protruded forward from the tip of the piercing device 52 after the tissue fastener inserted into the piercing device is pushed out, each of the cutting blades 271 extends in an arc shape by its own elasticity so that they draw a circle as a whole. Then, they are pulled back to the hand side in this condition. As a result, it is possible to cut in the intestinal wall Wd of the duodenum and the duct wall We of the common bile duct with the blade portions 281A in the rear portion, to thereby form a circular drainage hole 283.

Figure 76:
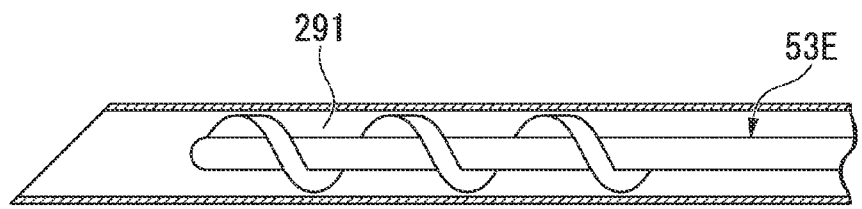
FIG. 76 shows another form of a stylet.

In a stylet 53E shown in FIG. 76, a spiral groove 291 is formed in a tip of the stylet.

When a common bile duct has an increased internal pressure due to retention of bile, it is preferable that a hole be provided in the common bile duct in advance, and that the manipulation be conducted in a state of a reduced internal pressure after the suction of the bile from this hole.

According to the stylet 53E with this structure, a base end side of the stylet 53E is connected with a suction mechanism, and the spiral groove 291 formed between the piercing device 52 and the stylet 53E can be utilized to suck the bile. In the case of using a simple stick-shaped stylet, there arise contradictory problems as follows. If to secure a bile suction passage, a gap between the stylet and the piercing device is made larger by making the diameter of the stylet smaller, it becomes difficult to push out the tissue fastener. On the contrary, if the diameter of the stylet is made larger to make the push-out of the tissue fastener favorable, it becomes difficult to secure a bile suction passage.

Figure 77:
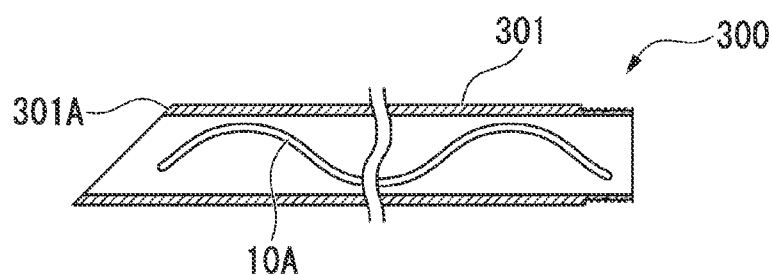
FIG. 77 to FIG. 78 show another form of a piercing device.
Figure 78:
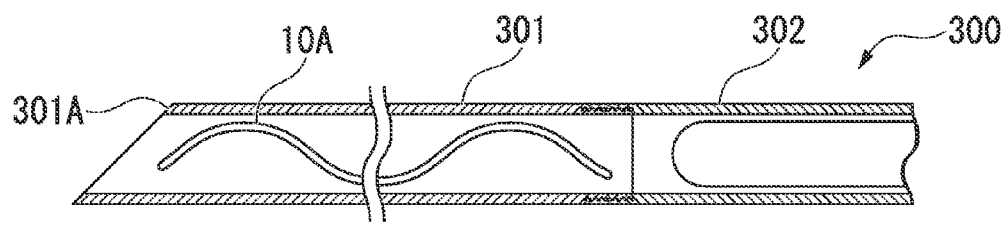

FIG. 77 and FIG. 78 show a modification of the piercing device.

In a piercing device 300 shown here, a tip portion 301 is a separate entity from a piercing device main unit 302, and hence is detachable by being threadingly fitted into the piercing device main unit 302.

When a tissue fastener 10A is previously inserted into a tip portion 301 of this piercing device to be used as a cartridge, it is possible to reuse the piercing device main unit 302 as a common portion by replacing a tip portion into which a tissue fastener 10A is inserted, as required. Furthermore, a needle tip portion 301A on the tip of the tip portion of the piercing device 300 is renewed for every use. Therefore, it is possible to secure a sharp edge.

Figure 79:
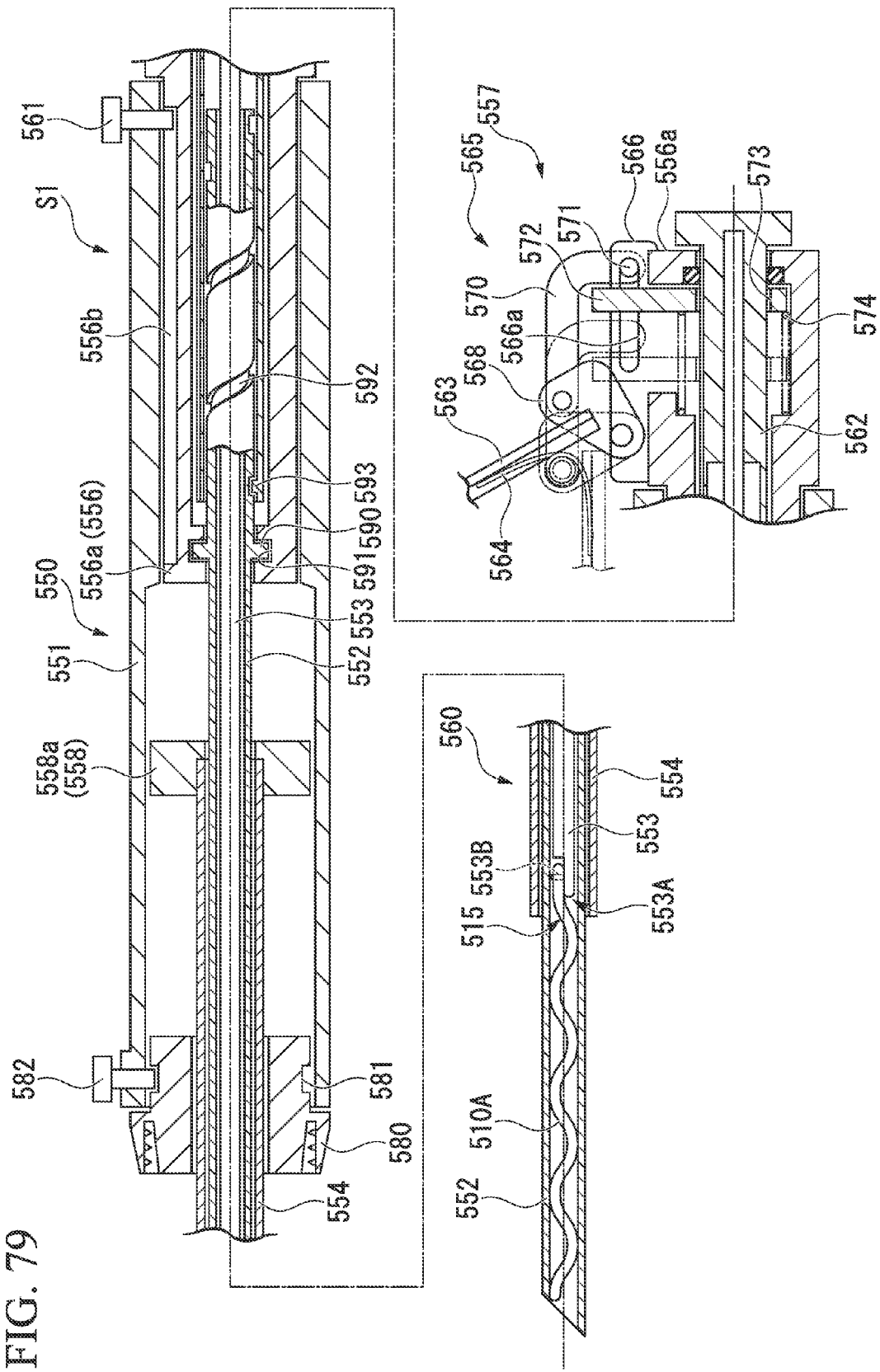
FIG. 79 is a cross-sectional view that shows the tissue fastening instrument and applicator in accordance with one embodiment of the present invention.

Hereinbelow an embodiment in accordance with the present invention shall be described. A tissue fastening device S1 of the present embodiment is a device that integrally fixes a first biological tissue and a second biological tissue, and performs a procedure that brings both tissues into communication. As shown in FIG. 79, it is provided with a tissue fastening instrument 510A and an applicator 550.

Here, the first and the second biological tissue do not necessarily denote different organs. For example, the case is also included in which a region of a certain organ serves as the first biological tissue, and another region of this organ serves as the second biological tissue, when these two regions being fixed. In the present embodiment, a description shall be given using as an example the procedure of the common bile duct serving as the second biological tissue being fixed to the duodenum serving as the first biological tissue, and bringing both organs into communication with one another.

Figure 80:
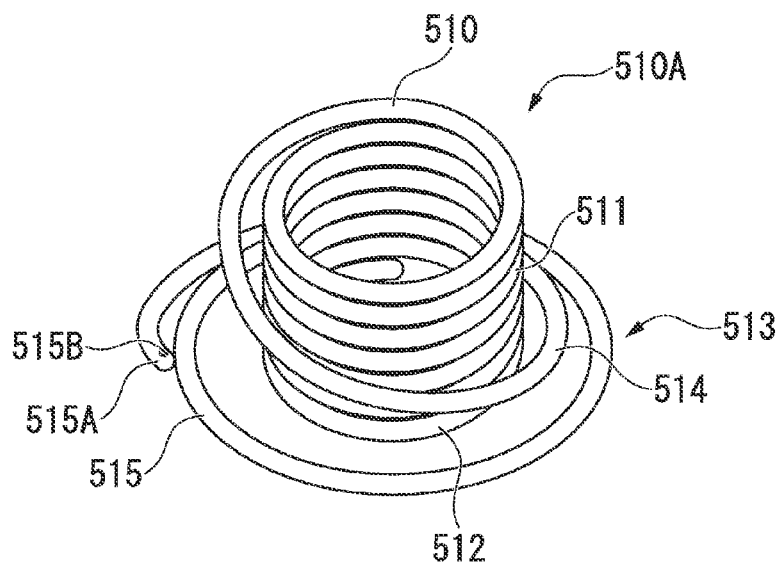
FIG. 80 is a perspective view of the same tissue fastening instrument.
Figure 81:
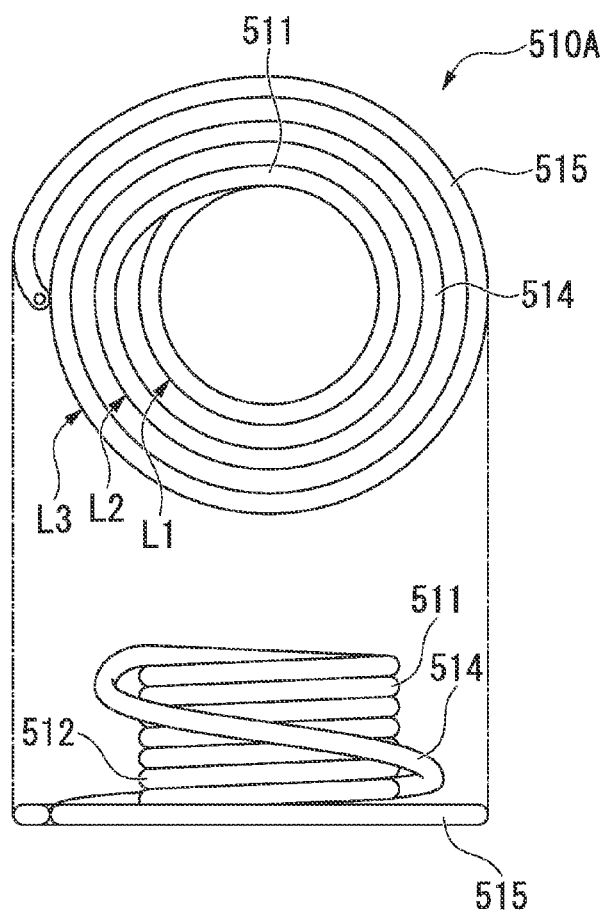
FIG. 81 is an elevation view and a plan view of the same tissue fastening instrument.

FIG. 80 and FIG. 81 are drawings that show the tissue fastening instrument 510A of the present embodiment. The tissue fastening instrument 510A is equipped with a first tissue fixing portion 511 that is engaged on the duodenum, a second tissue fixing portion 512 that is engaged on the common bile duct which is adjacent to the duodenum, and a peripheral spring portion 513 that is connected to the first tissue fixing portion 511 as shown in FIG. 80.

All of the sections of the tissue fastening instrument 510A, that is, the first tissue fixing portion 511, the second tissue fixing portion 512, and the peripheral spring portion 513, consist of a single high elasticity metal wire (hereinbelow simply referred to as a "metal wire") 510 that is wound in a coil shape. The first tissue fixing portion 511 and the second tissue fixing portion 512 are formed so as to have the same loop diameter, and with each other's loops being coaxial.

The peripheral spring portion 513 is provided with a spring portion 514 that extends from the end portion of the first tissue fixing portion 511, and an end turn portion 515 that extends from the end portion of the spring portion 514.

The spring portion 514 is extended from the end of the first tissue fixing portion 511 toward the second tissue fixing portion 512 while forming a loop that is larger than the first tissue fixing portion 511 and the second tissue fixing portion 512. The loop that the spring portion 514 forms gradually becomes large as it goes to the side of the second tissue fixing portion 512. Note that that shape is not essential to the present invention, and for example the spring portion 514 may extend toward the second tissue fixing portion 512 while forming a loop of the same diameter.

Since the spring portion 514 extends to the side of the second tissue fixing portion 512, the metal wire 510 that forms the spring portion 514, as shown in FIG. 81, has an angle so as to slope with respect to the axial line of the loop of the first tissue fixing portion 511 and the second tissue fixing portion 512 (hereinbelow called the "base loop").

Figure 82A:
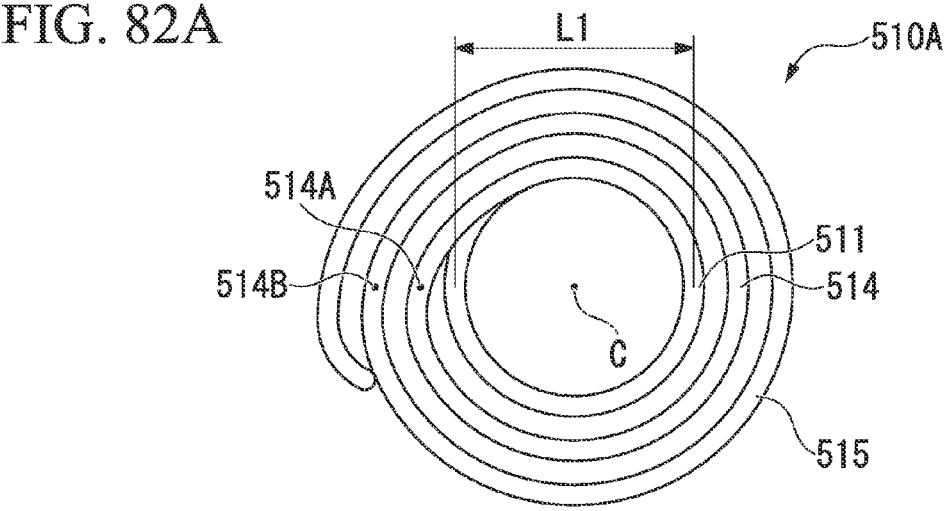
FIG. 82A and FIG. 82B are drawings that show the relationship of the peripheral spring of the same tissue fastening instrument and the force that acts.

The spring portion 514 is preferably formed so as to have an integer winding of 1 or more. An "integer winding of 1 or more" means that, when the tissue fastening instrument 510A is viewed from above as shown in FIG. 82A, an end portion 514A of the spring portion 514 on the side of the first tissue fixing portion 511 and an end portion 514B of the spring portion 514 on the side of the end turn portion 515 are aligned on the same straight line with a center C of a base loop L1 without sandwiching the center C.

Figure 82B:
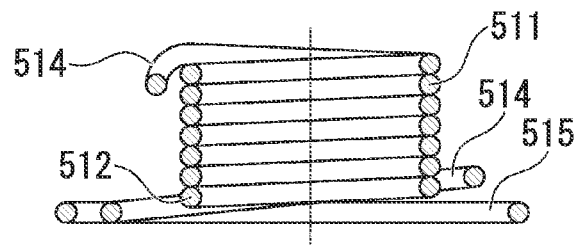
Figure 82C:
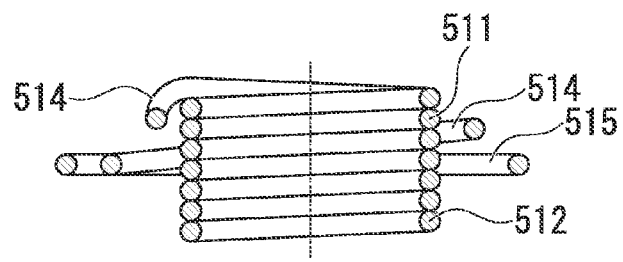
FIG. 82C and FIG. 82D are drawings that show the state of the tissue fastening instrument shown in FIG. 82A when placed in tissue.
Figure 82D:
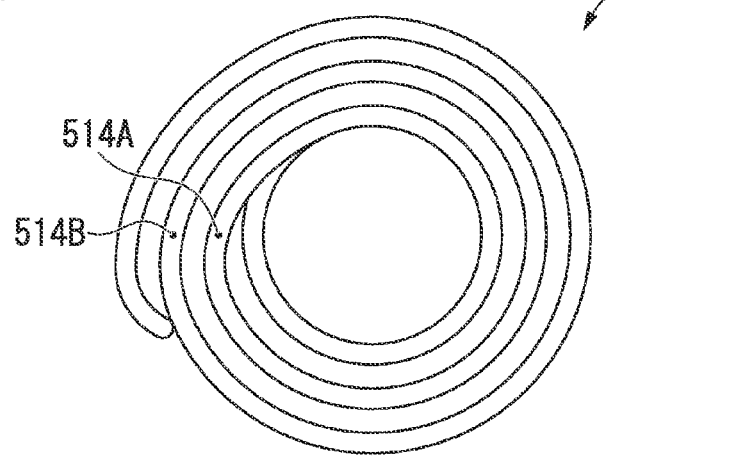

When the spring portion 514 is an integer winding of 1 or more, when the tissue fastening instrument 510A is viewed in cross section in the axial direction that passes through the center C, whichever cross section is taken, the spring portion 514 on the outer side in the diameter direction of the base loop L1 is in a state of being uniformly distributed as shown in FIG. 82B. Although FIG. 82B shows the state in which the spring portion 514 is set to one turn, provided it is an integer turn, the state is the same even for two or more turns. Therefore, the force of the spring portion 514 that acts in a direction perpendicular to the axial line of the base loop L1 (direction of a cross-section) becomes equal with respect to the first tissue fixing portion 511 and the second tissue fixing portion 512, and as shown in FIG. 4C and FIG. 4D, even when placed in tissue, the base loop of the first tissue fixing portion 511 and the second tissue fixing portion 512 does not cause axial discrepancy, and the shape is stable.

FIG. 83A to FIG. 83D show an example of the spring portion 514 set to ½ turn as an example of a non-integer turn. In this tissue fastening instrument 1110A, end portions 1114A and 1114B of a peripheral spring 1114 are aligned on the same straight line with the center C of the base loop L1, sandwiching the center C.

Figure 83A:
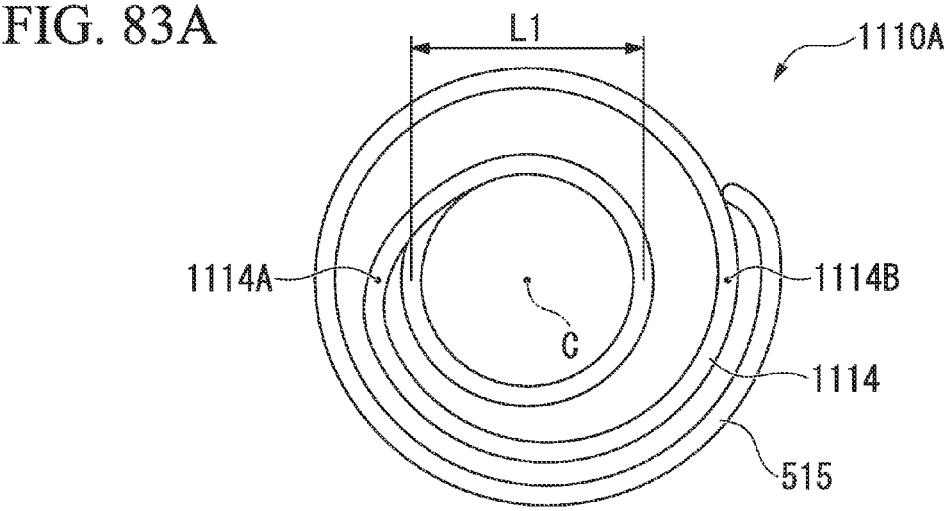
FIG. 83A and FIG. 83B are drawings that show the relationship of the peripheral spring of the same tissue fastening instrument and the force that acts.
Figure 83B:
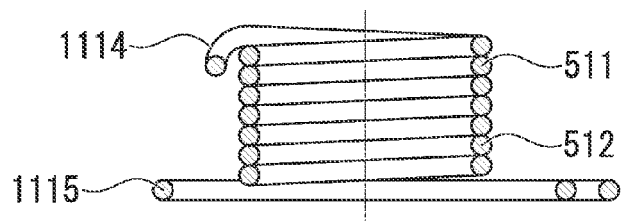
Figure 83C:
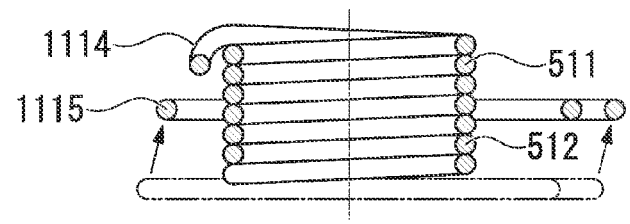
FIG. 83C and FIG. 83D are drawings that show the state of the tissue fastening instrument shown in FIG. 83A when placed in tissue.
Figure 83D:
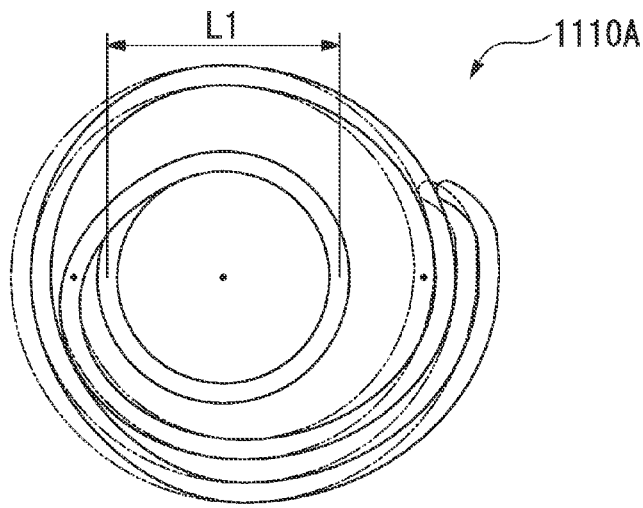

In this case, as shown in FIG. 83B, depending on how the cross-section in the axial direction passing through the center C is taken, the balance of the quantity of the spring portion 514 that exists on both sides of the first tissue fixing portion 511 and the second tissue fixing portion 512 is upset. When the tissue fastening instrument 1110A that has such a spring portion 1114 is placed in tissue, as shown in FIG. 83C and FIG. 83D, an axial discrepancy will arise between the base loop L1 and a loop L3 that the end turn portion 515 forms. As a result, a force that is out of balance acts in the cross-sectional direction, which becomes a hindrance to the first tissue fixing portion 511 and the second tissue fixing portion 512 sufficiently exhibiting the tissue fastening force mentioned later, which is not desirable.

The metal wire 510 changes its extension angle at the end portion 514B that corresponds to the connection portion of the spring portion 514 and the end turn portion 515, whereby the end turn portion 515 forms a loop that is perpendicular to the axial line of the base loop L1. Therefore, the loop of the end turn portion 515 is parallel to the base loop L1. As shown in FIG. 80, a through-hole 515B is formed at the end portion 515A of the end turn portion 515, and where the end turn portion 515 has formed a loop of one or more turns, the degree of bending is adjusted so that the end portion 515A touches another portion of the end turn portion 515.

The loop that the end turn portion 515 forms has a larger diameter than the loop that the spring portion 514 forms. Therefore, when the tissue fastening instrument 510A is viewed from the axial direction of the base loop L1 as shown by the plan view in FIG. 81, the base loop L1 is furthest to the inside the second loop L2 that the spring portion 514 forms is to the outside of that, and the third loop L3 that the end turn portion 515 forms is still further to the outside. The base loop L1, the second loop L2, and the third loop L3 are not mutually superimposed in the diameter direction of the base loop L1.

With the tissue fastening instrument 510A extended, one end is inserted in a biological tissue, and one tissue fixing portion, for example the second tissue fixing portion 512, is in turn passed through the intestinal wall of the duodenum and a tubular wall of the common bile duct. The shape of the second tissue fixing portion 512 that has passed through the intestinal wall of the duodenum and the tubular wall of the common bile duct is restored to the original coil shape by removing a restraint on the inner side of a common bile duct, and thus becomes caught on the common bile duct. The shape of the first tissue fixing portion 511 is restored to the original coil shape by removing a restraint on the inner side of the duodenum, and thus becomes caught on the duodenum. Due to the first tissue fixing portion 511 being caught on the duodenum and the second tissue fixing portion 512 being caught on the common bile duct, the intestinal wall of the duodenum and the tubular wall of the common bile duct are fastened and integrally fixed so as to be pressed against each other. At this time, the end turn portion 515 of the peripheral spring portion 513 abuts the intestinal wall of the duodenum around the first tissue fixing portion 511, and the spring portion 514 biases the end turn portion 515 so as to press the intestinal wall against the side of the common bile duct. These points are explained in detail in the explanation of the operation during use of the tissue fastening device S1.

The applicator 550 is an instrument for placing the tissue fastening instrument 510A in a body, and is provided with a main body 551, a needle tube 552, a stylet (fastening instrument pusher) 553, and a sheath 554 as shown in FIG. 79.

The main body 551 is formed in a cylindrical shape and has a needle tube control portion 556, a stylet control portion 557, and a ring member (sheath control portion) 558a for advancing and retracting the sheath 554 with respect to the main body 551. The needle tube 552, the stylet 553, and the sheath 554 all have flexibility, and are placed in a mutually coaxial shape. These constitute the insertion portion 560, which is pushed into a work channel of an insertion portion of an endoscope, with the insertion portion 560 naturally being longer than the work channel of the endoscope.

The needle tube 552 is used by being accommodated in a cavity with the tissue fastening instrument 510A in an extended state. The distal end surface of the needle tube 552 is formed slanted with respect to the lengthwise direction of the needle tube 552. Thereby, the distal end of the needle tube 552 is finished sharp. The base end of the needle tube 552 is connected to the needle tube control portion 556 provided at the rear of the main body 551.

Note that an electrode is provided at the distal end of the needle tube 552, and so the needle tube 552 may be inserted to pierce the intestinal wall of the duodenum and the tubular wall of the common bile duct while cauterizing biological tissue by passing electricity to the distal end. In this case, the distal end of the needle tube 552 may not be formed with a sharp tip.

The stylet 553 forms a shaft shape, is inserted inside the needle tube 552 in a manner capable of moving, and pushes out the tissue fastening instrument 510A that has been inserted in the needle tube 552 from the distal end of the needle tube 552. A projection 553B is formed at a distal end 553A of the stylet 553, and as shown in FIG. 79, the tissue fastening instrument 510A is accommodated in the needle tube 552 in the state of the through-hole 515B of the end turn portion 515 and the projection 553B being engaged.

For this reason, the tissue fastening instrument 510A becomes integrated with the stylet 553 and capable of moving forward and backward in the needle tube 552, and when the stylet 553 is rotated about the axis line, rotates together with the stylet 553. The gap between the inner cavity of the needle tube 552 and the stylet 553 is set to be smaller than the wire diameter of the metal wire 510 that constitutes the tissue fastening instrument 510A. Therefore, the engagement of the through-hole 515B and the projection 553B does not come apart within the needle tube 552. In addition, in making the gap between inner cavity of the needle tube 552 and the stylet 553 small, the diameter of the stylet 553 may be enlarged, and also the projection length of the projection 553B may be lengthened. Furthermore, instead of making the gap between inner cavity of the needle tube 552 and the stylet 553 small, the maximum diameter of the metal wire 510 may be enlarged, and so by restricting the movable range of the metal wire 510 in the needle tube 552, the aforementioned engagement release may be restricted.

The base end of the stylet 553 is connected to the stylet control portion 557 provided in the inside of the needle tube control portion 556 described below.

The sheath 554 is a tubular member that has flexibility, and the needle tube 552 is inserted in the inner cavity in a movable manner. The distal end face of the sheath 554 is formed flat so as to be orthogonal to the lengthwise direction of the sheath 554.

The needle tube control portion 556 is provided with a cylindrical first shaft 556a that is inserted in the inner side from the rear end of the main body 551. The outer diameter of the first shaft 556a is slightly smaller than the inner diameter of the rear portion of the main body 551. Therefore, the first shaft 556a is capable of sliding on the inner surface of the rear portion of the main body 551. The base end of the needle tube 552 is fixed to the distal end surface of the first shaft 556a that is inserted in the main body 551 so as to cause the lengthwise direction of the needle tube 552 to coincide with the lengthwise direction of the first shaft 556a. The needle tube 552, by causing the first shaft 556a to slide with respect to the main body 551, can change its relative position with the main body 551.

A female screw hole is formed in the diameter direction of the main body 551 at the rear portion of the main body 551, and a external thread 561 is screwed into this female screw hole. The distal end of the external thread 561 projects into the inner cavity of the main body 551. A slot 556b is formed on the outer surface of the first shaft 556a along the lengthwise direction of the first shaft 556a. The distal end of the external thread 561 is loosely fitted in the slot 556b. Thereby, the slot 556b regulates the movable range of the first shaft 556a with respect to the main body 551. By screwing the external thread 561 further into the female screw hole to make the distal end thereof press against the bottom surface of the slot 556b, it is possible to hold the first shaft 556a at any position with respect to the main body 551.

The stylet control portion 557 has a cylindrical second shaft 562 that is inserted from the rear end of the first shaft 556a to the inner side, a lever 563 that is swingably supported by the first shaft 556a that supports the needle tube 552, a twisted coil spring 564 that biases the lever 563 in a direction away from the main body 551, and a link mechanism 565 that changes the swing movement of the lever 563 to a linear movement along the piercing tool 552 of the stylet 553.

The base end of the stylet 553 is inserted from the distal end of the second shaft 562 to the inside thereof and fixed to the second shaft 562 so as to make the lengthwise direction of the stylet 553 coincide with the lengthwise direction of the second shaft 562. The stylet 553, by causing the second shaft 562 to slide with respect to the first shaft 556a, can change the relative position with the needle tube 552.

A projection 590 is formed on the periphery of the needle tube 552, and this projection 590 is fitted to a ring slot 591 formed on the circumference of the distal end portion of the needle tube control portion 556. By this, the needle tube 552 is capable of relative rotation with respect to the needle tube control portion 556 while incapable of relative movement in the axial direction. A spirally shaped slot 592 is formed on the outer circumferential surface of the base end side of the needle tube 552 beyond the projection 590.

A pin-shaped projection 593 is provided on the inner circumferential surface of the second shaft 562 that faces the outer circumferential surface of the needle tube 552, and this projection 593 engages with the spirally shaped slot 592 (hereinbelow referred to as "spiral slot 592"). Moreover, a longitudinal groove 594 is formed on the outer circumference of the second shaft 562, and a plate member 572 is attached to the outer side of the second shaft 562 (refer to FIG. 86B). A projection 595 is formed in the inner circumferential portion of the plate member 572, and this projection 595 is fitted in the longitudinal groove 594. Thereby, the second shaft 562 is capable of relative movement in the axial direction in the state of being prevented from rotating with respect to the plate member 572. Due to the mutual correspondence of the ring slot 591 and the projection 590, and the spiral slot 592 and the projection 593, a rotation mechanism 596 is constituted that causes the needle tube 552 to rotate when the second shaft 562 that is prevented from rotating moves forward or backward along the axial direction.

The shape of the spiral slot 592 is set so that when the needle tube 552 rotates with movement of the second shaft 562 in the axial direction, the rotation direction of the needle tube 552 and the coil winding direction of the tissue fastening instrument 510A become reversed. Furthermore, although the stylet 553 pushes out the tissue fastening instrument 510A from the distal end of the needle tube 552 by movement of the second shaft 562 in the axial direction, the shape of the spiral slot 592 is set so that the needle tube 552 completes one rotation each time the tissue fastening instrument 510A is pushed out by only the length of one coil portion from the distal end of the needle tube 552. Therefore, the length of the spiral slot per a rotation of the needle tube differs in the region of the spiral slot 592 that is engaged with the projection 593 when the first tissue fixing portion 511 and the second tissue fixing portion 512 are being pushed out and the region of the spiral slot 592 that is engaged with the projection 593 when the peripheral spring portion 513 is being pushed out.

In addition, although the present embodiment provides the spiral slot 592 in the outer circumference of the needle tube 552 and the projection 593 in the inner circumference of the second shaft 562, it is not limited thereto. Instead, a projection may be provided on the outer circumference of the needle tube 552, the spiral slot may be provided on the inner circumference of the second shaft 562, the spiral shape may be a convexity instead of a slot, and the rotation mechanism may be constituted using a projection or the like that is capable of engagement therewith.

The link mechanism 565 is provided with a base member 566, a bracket 568, a bar 570, a plate member 572, and a compression coil spring 574. The base member 566 is fixed to the outside surface of the first shaft 556a. The bracket 568 is pivotally supported by the base member 566. The lever 563 is fixed to the lower end of the bracket 568. The bar 570 is pivotally supported by the bracket 568 at one end, and is pivotally supported by the base portion material 566 at the other end. A pin 571 provided at the other end of the bar 570 is fitted in a long hole 566a formed in the base member 566 along the sliding direction of the second shaft 562 in a manner providing play.

A hole 573 with a diameter that is larger than the outer diameter of the second shaft 562 is formed in the plate member 572, and the second shaft 562 that is inserted in the first shaft 556a is passed through this hole 573. The difference of the outer diameter of the second shaft 562 and the inner diameter of a hole 573 is extremely small, and by leaning the plate member 572 to move in the lengthwise direction of the second shaft 562, that is, the insertion direction of the second shaft 562 in the first shaft 556a, the inner surface of the hole 573 interferes with the outer surface of the second shaft 562 to cause friction, whereby a force that is added to the plate member 572 acts on the second shaft 562.

The compression coil spring 574 is disposed inside of the first shaft 556a, and biases the plate member 572 in the opposite direction of the insertion direction of the second shaft 562 in the first shaft 556a.

When the lever 563 is moved in the direction of approaching the main body 551, the bar 570 is pulled towards the front of the main body 551 via the bracket 568, and the other end of the bar 570 moves along the long hole 66a. The plate member 572 is pushed by the other end of the bar 570 and moves in the insertion direction of the second shaft 562 in the first shaft 556a, resisting the compression coil spring 574. Since friction is produced between the second shaft 562 and the plate member 572 as a result of the latter tilting slightly, the force that is added to the plate member 572 acts on the second shaft 562, and the second shaft 562 is thrust into the first shaft 556a.

When the lever 563 is released, the twisted coil spring 564 causes the lever 563 to separate from the main body 551, and the compression coil spring 574 pushes only the plate member 572 back to its initial position without causing friction with the second shaft 562.

Since the amount of movement of the other end of the bar 570 per operation of the lever 563 is always constant, the insertion length of the second shaft 562 into the first shaft 556a per operation of a lever 563 is also always constant. Therefore, it is possible to control the insertion length of the second shaft 562 into the first shaft 556a, that is, the insertion length of the stylet 553 into the needle tube 552 according to the number of times of operation of the lever 563. This means that it is possible to control the length of the tissue fastening instrument 510A pushed out from the distal end of the needle tube 552 according to the number of times of operation of the lever 563.

When the tissue fastening instrument 510A forms a coil shape that has a loop outside of the needle tube 552 as in the present embodiment, the insertion length of the stylet 553 per operation of the lever 563 is preferably about n times of the loop of the tissue fastening instrument 510A or about 1/n times (n being a natural number).

For example, if the insertion length of the stylet 553 per operation of the lever 563 is almost equal to the circumference of the tissue fastening instrument 510A, whenever the lever 563 is operated once, the tissue fastening instrument 510A will be pushed out from the distal end of the needle tube 552 by an amount corresponding to one turn. Moreover, when the second tissue fixing portion 512 is a two-turn portion of the tissue fastening instrument 510A, by operating the lever 563 two times, it is possible to push out only the second tissue fixing portion 512 from the distal end of the needle tube 552.

Moreover, if the insertion length of the stylet 553 per operation of the lever 563 is almost equal to half of the circumference of the tissue fastening instrument 510A, whenever the lever 563 is operated once, the tissue fastening instrument 510A will be pushed out from the distal end of the needle tube 552 by an amount corresponding to half a turn. Furthermore, when the second tissue fixing portion 512 is a two-turn portion of the tissue fastening instrument 510A, by operating the lever 563 four times, it is possible to push out only the second tissue fixing portion 512 from the distal end of the needle tube 552.

Moreover, regarding the spring portion 514 and the end turn portion 515 of the peripheral spring portion 513, by setting the length thereof to an integral multiple of the insertion length of the stylet 553 per single operation of the lever 563, it is possible to push out only the spring portion 514 or the end turn portion 515 from the needle tube 552.

A mouth ring 580 is inserted at the distal end of the main body 551. An inner screw 580A is formed in the mouth ring 580, and by screwing the inner screw 580A into a cap of an endoscope, it is possible to fix the applicator 550 to the endoscope. On the outer surface of the mouth ring 580, a groove 581 is formed along the circumferential direction. A female screw hole that extends in the diameter direction is formed in the main body 551, and an external thread 582 is screwed into this female screw hole. The distal end of the external thread 582 projects to the inside of the main body 551. The distal end of the external thread 582 loosely fits into the groove 581 of the mouth ring 580. Thereby, it is possible to freely rotate the entire applicator 550 with respect to the mouth ring 580 that is fixed to the endoscope. By further screwing the external thread 582 into the female screw hole to make the distal end thereof press against the bottom surface of the groove 581, it is possible to position and hold the main body 551 at any position in the circumferential direction with respect to the mouth ring 580.

Figure 84:
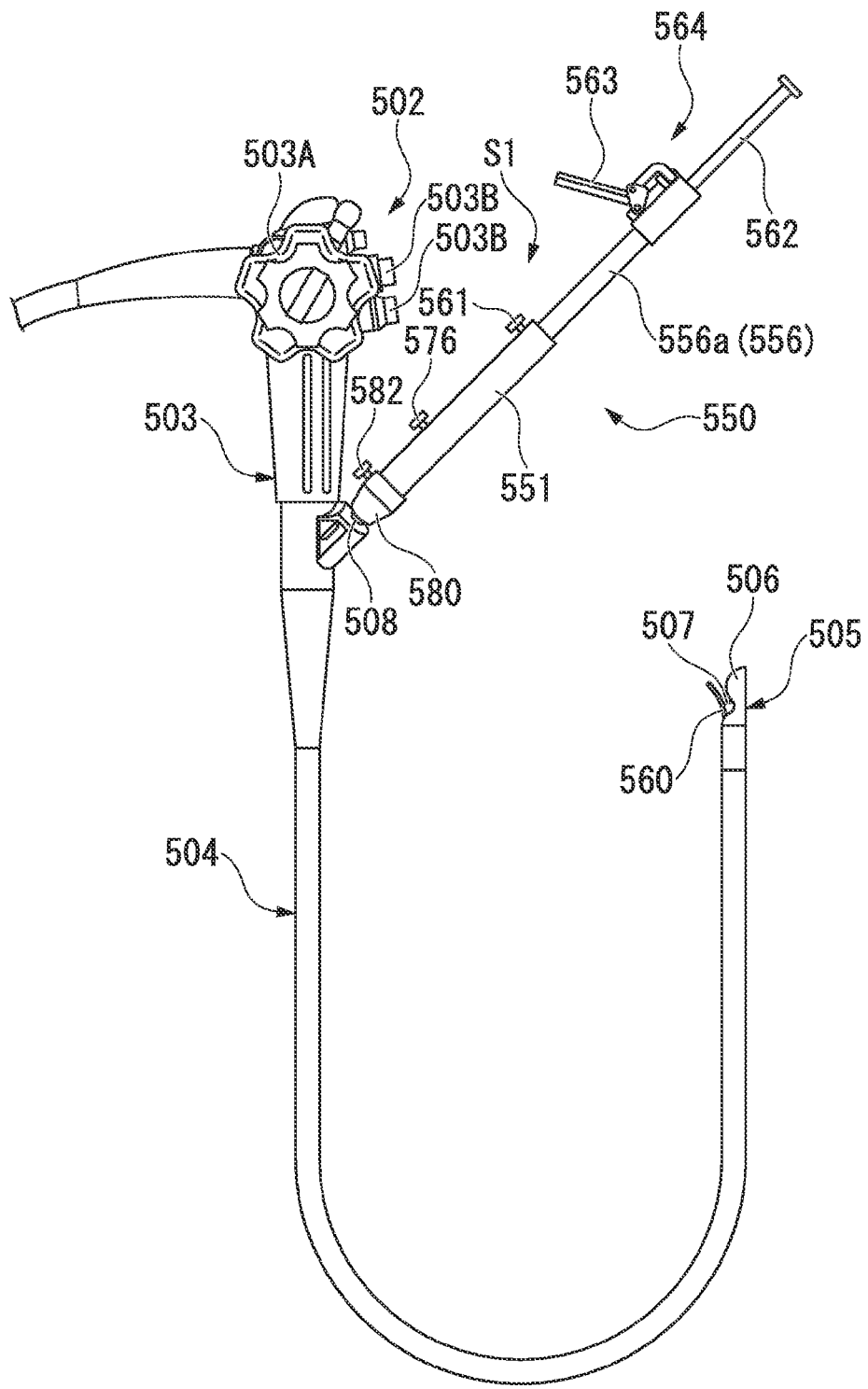
FIG. 84 is a drawing that shows the state of the same applicator inserted in an endoscope.

FIG. 84 shows a linear scanning-type ultrasonic endoscope (hereinbelow simply referred to as an "endoscope") 502 as an example of an endoscope that is used together with the tissue fastening device S1. The endoscope 502 is provided with a flexible insertion portion 504 that extends from the control portion 503 that is used outside a body.

A knob 503A and various buttons 503B that cause the distal end portion of the insertion portion 504 to curve are provided in the control portion 503. A cover 505 is attached to the distal end of the insertion portion 504. An ultrasonic device 506 is attached to this cover 505.

The ultrasonic device 506 bulges out on a plane that includes the axial line of the insertion portion 504, and a plurality of ultrasonic transducers are arranged along the circular periphery. Moreover, an elevator base 507 is provided so as to feed the distal end portion of the applicator 550 to the side. By operating the elevator base 507 proximally, it is possible to adjust the direction of the insertion portion 60 of the applicator 550 that is fed out from the distal end of the insertion portion 504. Note that the endoscope 502 may also be provided with another probe-type ultrasonic endoscope. Also, it is possible to use an endoscope that does not have the ultrasonic device 506. In this case, an ultrasonic device that is used outside of the body, an X-ray device, a magnetic resonance imaging device, or a computerized tomography device are used in combination.

Figure 85:
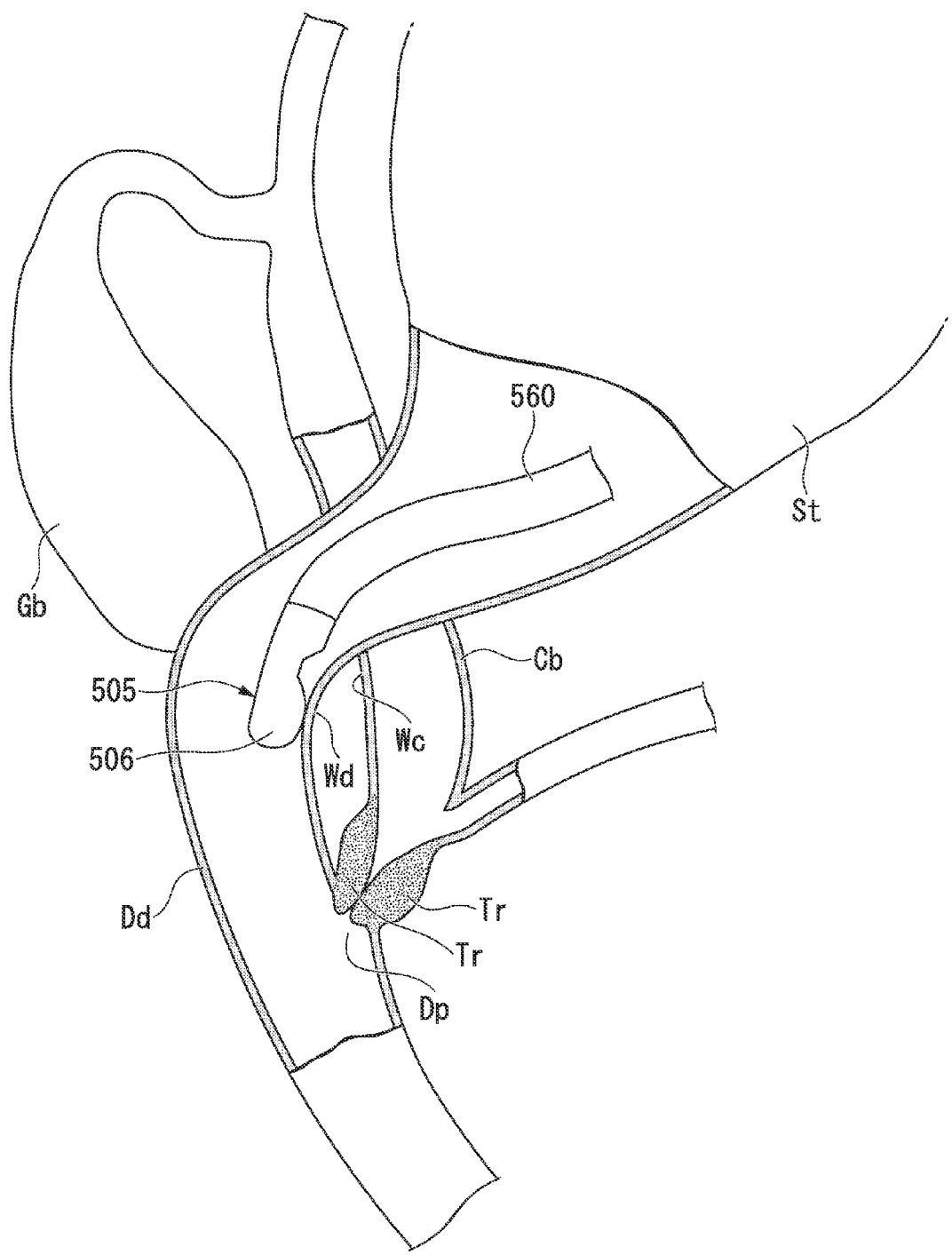
FIG. 85 is a drawing that shows the operation of the same endoscope during use of the same applicator.

Next, a procedure shall be explained of placing the tissue fastening instrument 510A in an abdominal cavity using the tissue fastening device S1 constituted as mentioned above, integrally fixing the duodenum and the common bile duct, and forming a hole that brings both into communication. This kind of procedure, as shown for example in FIG. 85, is carried out in the case of the discharge of bile being prevented by blockage of the duodenal papilla Dp by a tumor Tr, causing jaundice in which the bile is absorbed into blood. By this procedure, it is possible to directly discharge the bile from the common bile duct Cb to the duodenum Dd.

First, the insertion portion 4 of the endoscope 502 is inserted from a patient's mouth. The endoscope 502 is inserted in the duodenum Dd which is the upper part of the gastrointestinal tract. The state of the outer side of the duodenum Dd is investigated with the ultrasonic endoscope 506, and a location suitable for the procedure near the common bile duct Cb is searched for on the stomach St side from the duodenal papilla Dp.

The operator in advance retracts the needle tube 552 with respect to the main body 551 by operating the first shaft 556a of the applicator 550, and retracts the stylet 553 with respect to the main body 551 by operating the second shaft 562, as shown in FIG. 83A. Furthermore, by operating the ring member 558a, the sheath 554 is retracted with respect to the main body 551, In this state, the distal end of the needle tube 552 in which the tissue fastening instrument 510A has been inserted is drawn to the inside of the sheath 554.

The operator inserts the insertion portion 560 of the applicator 550 in the work channel of the endoscope 502 and makes it move forward, and engages the mouth ring 580 with a forceps plug 508 of the endoscope to fix the applicator 550 to the endoscope 502. Thereby, the distal end of the insertion portion 560 is protruded from the distal end of the insertion portion 504 of the endoscope 502. Then, the direction of the protruded insertion portion 560 is adjusted by the elevator base 507.

Figure 87:
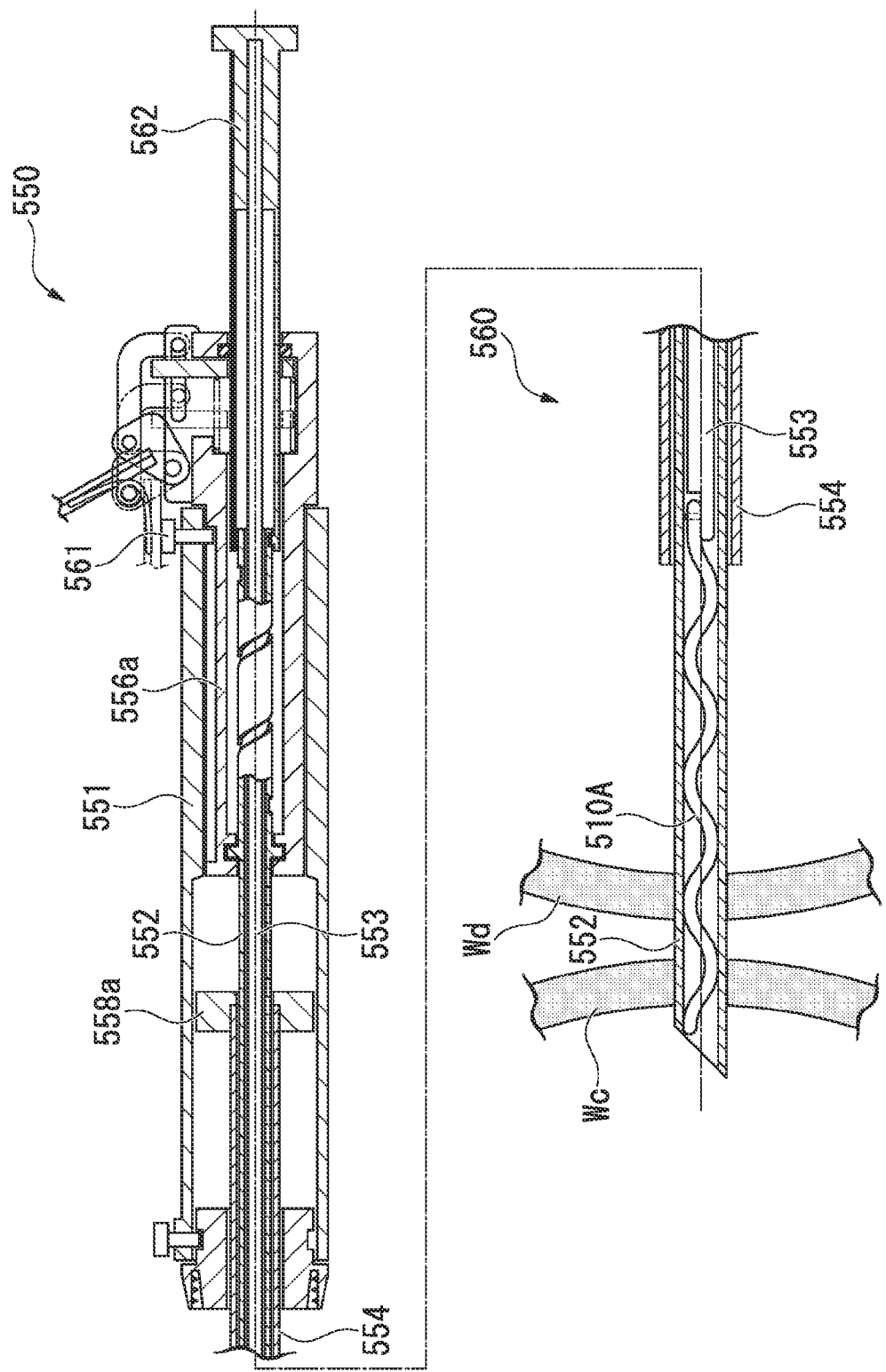
FIG. 87 to FIG. 89 are drawings that show the operation during use of the same tissue fastening instrument and the same applicator.

The common bile duct Cb beyond the duodenum Dd is scanned using the ultrasonic device 506 provided in the endoscope 502, and the location to insert the needle tube 552 in the common bile duct Cb is determined. As shown in FIG. 87, the external thread 561 is loosened, the first shaft 556a is pushed into the main body 551, and the distal end of the needle tube 552 is made to project from the distal end of the sheath 554. Thereby, the sharp distal end of the needle tube 552 pierces through the intestinal wall Wd of the duodenum Dd from the inside to the outside, and successively pierces through the wall We of the common bile duct Cb from the outside to the inside. The operator then tightens the external thread 561 to fix the first shaft 556*a* to the main body 551.

Figure 88:
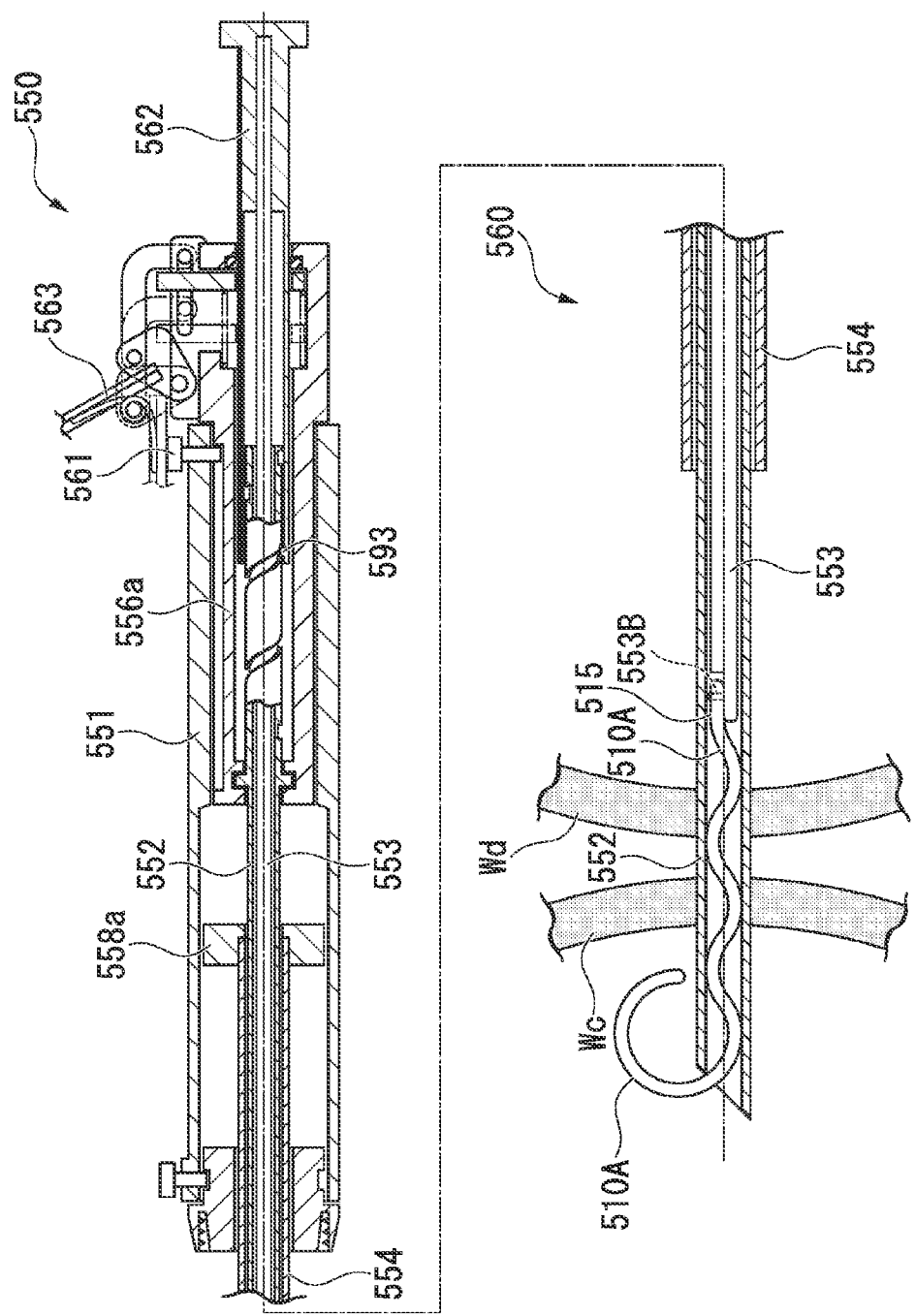

The operator, as shown in FIG. 88, operates the lever 563 to push the second shaft 562 into the first shaft 556*a* by a predetermined amount. For example, the lever 563 may be operated a definite number of times. Thereby, the stylet 553 changes the relative position with the needle tube 552, and the second tissue fixing portion 512 of the tissue fastening instrument 510A is pushed out from the distal end of the needle tube 552. At this time, along with the advance of the second shaft 562, the projection 593 provided in the second shaft 562 moves along the spiral slot 592 of the needle tube 552. Meanwhile, rotation of the second shaft 562 is restricted by the projection 595 of the plate member 572 being engaged in the longitudinal groove 594 formed in the outer circumference. As a result, the needle tube 552 rotates with the advance of the second shaft 562. Since the tissue fastening instrument 510A and the stylet 553 are united at this time by the projection 553B being engaged in the through-hole 515B of the end turn portion 515, the advance and retreat as well as rotation of the stylet are suitably transmitted to the tissue fastening instrument 510A.

As the rotation direction of the needle tube 552 when viewed from the base end side of the main body 551 becomes the opposite to the coil winding direction of the tissue fastening instrument 510A to be pushed out from the distal end of the needle tube 552, the second tissue fixing portion 512 to be pushed out from the needle tube 552 promptly reverts to the coil shape prior to being accommodated in the needle tube 552 without twisting (this is explained in detail below), and catches onto and holds the inner side of the wall Wc of the common bile duct Cb.

The external thread 561 is loosened, the first shaft 556*a* is pulled out a little from the main body 551, and the projection length from the distal end of the sheath 554 of the needle tube 552 is shortened. Then, the external thread 561 is tightened to again fix the first shaft 556*a* to the main body 551. Thereby the distal end of the needle tube 552 is spaced a little away from the internal surface of the intestinal wall Wd of the duodenum Dd.

As shown in FIG. 89, the lever 563 is again operated to push the second shaft 562 into the first shaft 556 by a predetermined amount. For example, the lever 563 may be operated a definite number of times. Thereby, the stylet 553 changes the relative position with the needle tube 552, and the first tissue fixing portion 511 of the tissue fastening instrument 510A is pushed out from the distal end of the needle tube 552. At this time, similarly to during the pushing out of the second tissue fixing portion 512, the needle tube 552 rotates in the opposite direction to the coil winding direction of the tissue fastening instrument 510A. As a result, when the first tissue fixing portion 511 is pushed out from the needle tube 552, it promptly reverts to the initial coil shape without twisting (this is explained in detail below), and catches onto and holds the inner side of the intestinal wall Wd of the duodenum Pd.

Below, the action of the tissue fastening instrument 510A pushed out from the distal end of the needle tube 552 in the procedure mentioned above is explained in detail.

First, the tissue fastening instrument 510A is pushed out from the distal end of the needle tube 552 that has penetrated the intestinal wall Wd of the duodenum Dd and the wall Wc of the common bile duct Cb, so that only the second tissue fixing portion 512 is projected. The second tissue fixing portion 512, in the process of being pushed out from the distal end of the needle tube 552, successively reverts to its original coil shape and catches onto and holds the wall Wc of the common bile duct Cb.

Figure 90A:
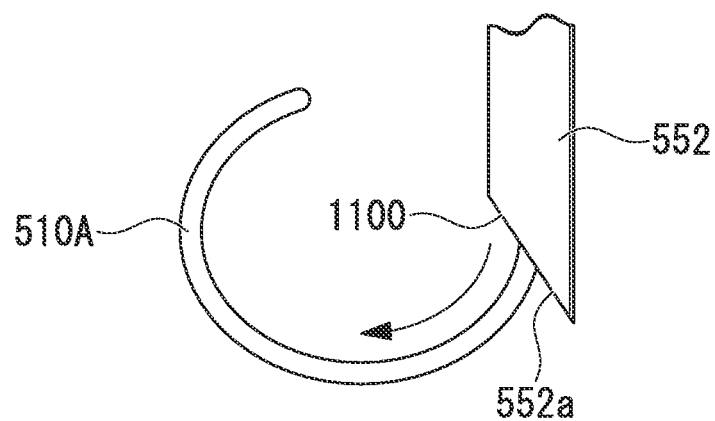
FIG. 90A and FIG. 90B are drawings that show the operation when the same tissue fastening instrument is pushed out from the needle tube of the same applicator.
Figure 90B:
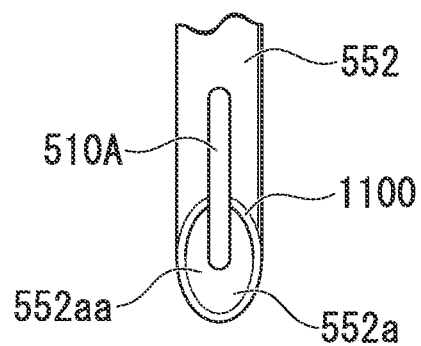

The tissue fastening instrument 510A that is loaded in the extended state in the needle tube 552 always tries to return to its original coil shape outside of the needle tube 552 due to the elastic force. As a result, when pushed out from the distal end of the needle tube 552, as shown in FIG. 90A and FIG. 90B, it is pushed out at an opening portion 1100 that is closest to the root side at the distal end of the needle tube 552 while heading to the surface that becomes the inside of the loop. Here, in the case of the distal end of the needle tube 552 having a sloped opening 552*a* that obliquely slopes like a hypodermic needle, the tissue fastening instrument 510A is pushed out from the most root side of the sloped opening 552*a*, and so tries to return to the original shape while existing on a plane that is approximately perpendicular with respect to a sloped opening plane 552*aa*.

Therefore, if the needle tube 552 is rotated simultaneously while pushing out the tissue fastening instrument 510A from the sloped opening 552*a* of the needle tube 552, the tissue fastening instrument 510A will rotate united with the needle tube 552.

In the event of pushing out the tissue fastening instrument 510A from the needle tube 552, when the tissue fastening instrument 510A cannot make contact with the surrounding common bile duct wall Wc, the tissue fastening instrument 510A correctly returns to its original shape. However, when the tissue fastening instrument 510A can make contact with the surrounding common bile duct wall Wc and the like, the tissue fastening instrument 510A may be unable to return to the original shape.

Figures 91A, 91B, 91C:
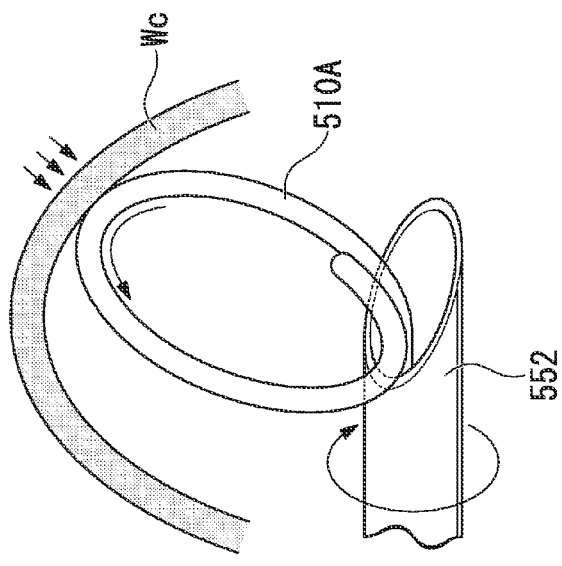
FIG. 91A to FIG. 91D are drawings that show the operation of the same tissue fastening instrument and the same needle tube.

This phenomenon shall be described using as an example the case where the tissue fastening instrument 150A is a clockwise-wound (Z winding) coils If the tissue fastening instrument 510A is further pushed out from the needle tube 552 from the state of FIGS. 512A and 512B, ordinarily it returns to the original clockwise-wound coil as shown in FIG. 91A. However, in the case of the tissue fastening instrument 510A making contact with the common bile duct wall Wc as shown in FIG. 91B, there is a possibility of the tissue fastening instrument 510A being pushed by the common bile duct wall Wc and becoming a counterclockwise-wound coil (S winding) coil that is the opposite from the original.

In order to prevent this, as shown in FIG. 91C, the tissue fastening instrument 510A should be pushed out from the needle tube 552 while causing it to rotate integrally with the needle tube 552 so as to rotate in the opposite direction from the winding direction of the tissue fastening instrument 510A as shown in FIG. 91C, that is, if the tissue fastening instrument 510A is a clockwise-wound coil, to rotate to the left if viewing the needle tube 552 from the base end. By doing so, the tissue fastening instrument 510A will rotate to the left with the needle tube 552, and push the common bile duct wall Wc. Thereby, the tissue fastening instrument 510A returns to the original clockwise winding coil.

Figure 91D:
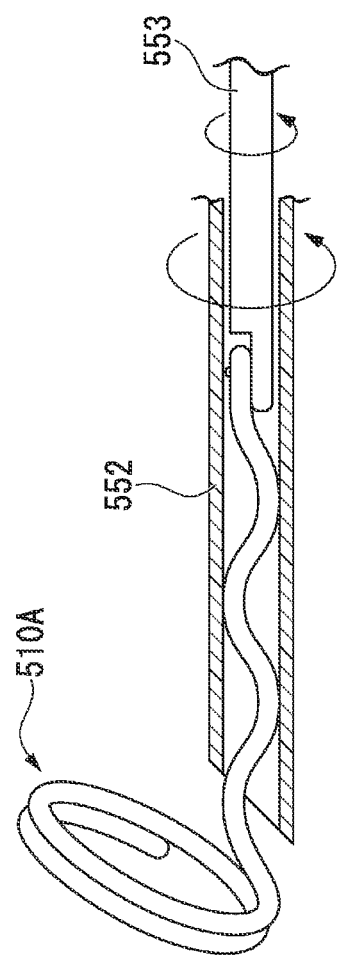

In the applicator 550 of the present embodiment, the shape of the spiral slot 592 is set so that the rotation direction of the needle tube 552 may rotate in a counterclockwise manner toward the distal end side, which is the opposite from the winding direction of the tissue fastening instrument 510A. Accordingly, when letting out the tissue fastening instrument 510A, the needle tube 552 and the stylet 553 are rotated in the counterclockwise direction. Furthermore, since the tissue fastening instrument 510A and the stylet 553 are engaged, rotation of the stylet 553 is favorably transmitted to the tissue fastening instrument 510A, whereby the tissue fastening instrument 510A is let out from the needle tube 552 while being reliably rotated. By these actions, as shown in FIG. 91), the tissue fastening instrument 510A that is pushed out to the outside of the needle tube 552 favorably reverts to the original clockwise wound loop shape, and so tangling and a reduction in tissue fastening strength due to changes in the winding direction are prevented.

After the second tissue fixing portion 512 of the tissue fastening instrument 510A is pushed out from the needle tube 552 in the common bile duct Cd, the first tissue fixing portion 511 is pushed out from the distal end of the needle tube 552 that has been pulled out from the intestinal wall Wd of the duodenum Dd and the wall Wc of the common bile duct Cb. At this time as well, since the needle tube 552 is rotated simultaneously while pushing out the tissue fastening instrument 510A from the sloped opening 552a of the needle tube 552, the portion of the base loop of the tissue fastening instrument 510A is smoothly placed.

Figure 92:
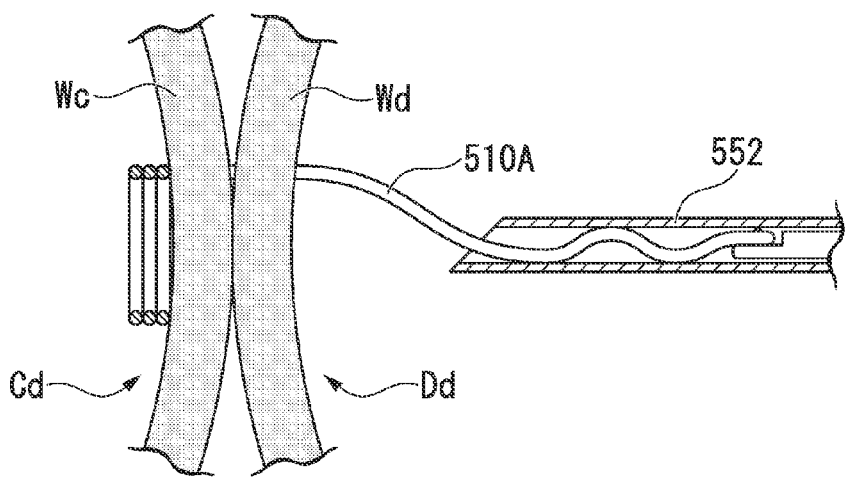
FIG. 92 to FIG. 94 are drawings that show the state of an irregularity occurring during placement of the same tissue fastening instrument.
Figure 93:
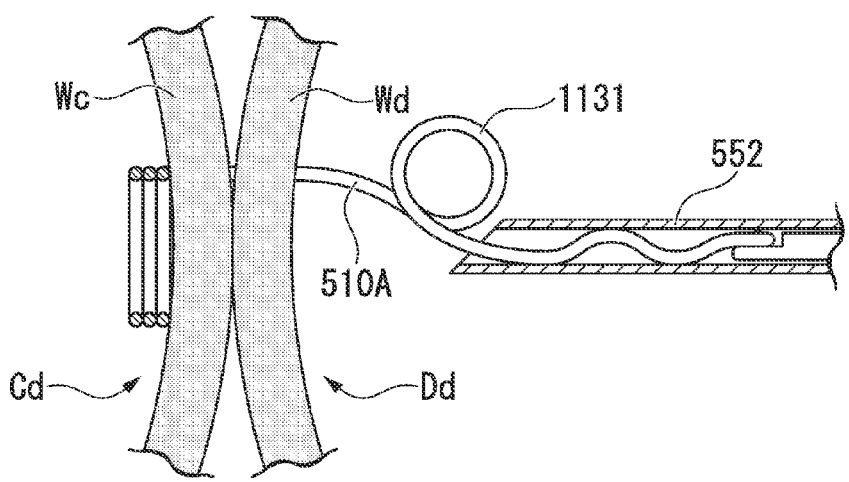
Figure 94:
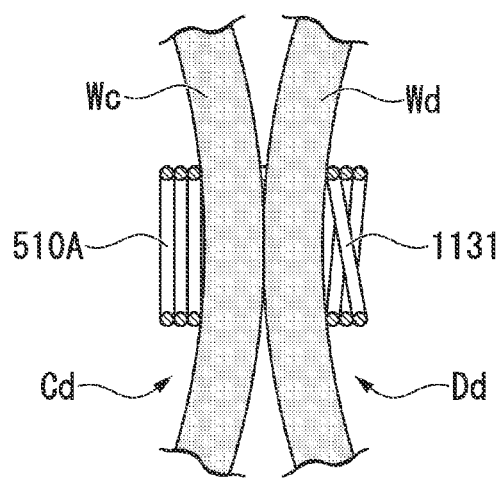

After the tissue fastening instrument 510A is latched onto the second biological tissue, FIG. 92 to FIG. 94 are drawings that explain the problem when being latched onto the first biological tissue. As shown in these drawings, after the tissue fastening instrument 510A is latched onto, for example, the wall Wc of the common bile duct Cd that is the second biological tissue, when being latched onto for example the intestinal wall Wd of duodenum Dd that is the first biological tissue, due to the force of the tissue fastening instrument 510A trying to return to its original coil shape, a twisted portion 1131 occurs as shown in FIG. 93, and finally as shown in FIG. 94, the tissue fastening instrument 510A may be placed in a tangled state starting from the twisted portion 1131.

In the tissue fastening instrument 510A and the applicator 550 of present embodiment, the above tangling is suitably prevented. This is explained in detail below.

Since the motion of the tissue fastening instrument 510A returning to the coil shape on the intestinal wall Wd of the duodenum Dd at the time of placing is also a rotating motion above the intestinal wall Wd as shown in FIG. 95 to FIG. 99, if the motion of this tissue fastening instrument 510A and the rotation of the needle tube 552 are synchronized, placing of the tissue fastening instrument 510A goes smoothly.

Figure 95:
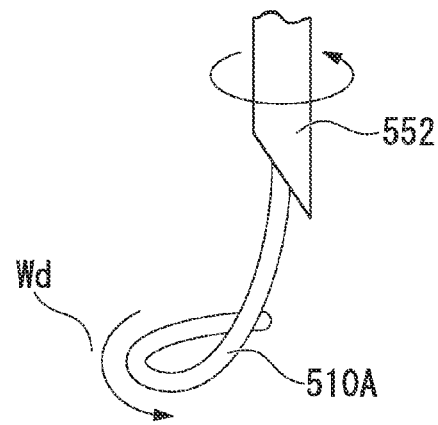
FIG. 95 to FIG. 99 are drawings that show the operation of the same tissue fastening instrument and the same needle tube in order to suitably place the same tissue fastening instrument.
Figure 96:
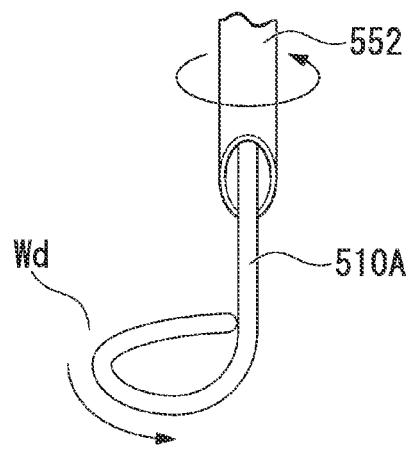
Figure 97:
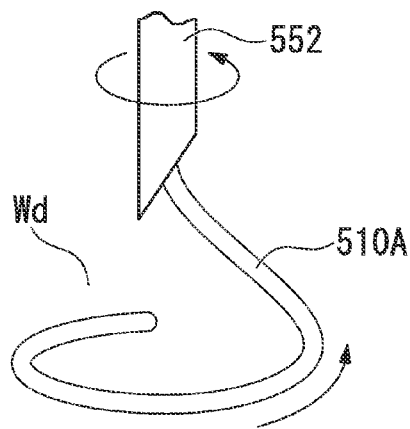
Figure 98:
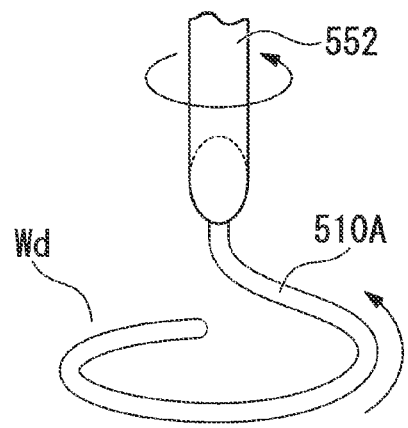
Figure 99:
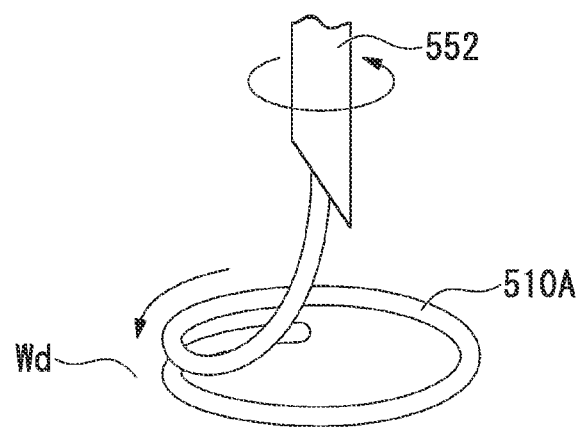

Specifically, in the case of the tissue fastening instrument 510A being wound clockwise, the metal wire 510 that constitutes the tissue fastening instrument 510A, when viewed from the base end side, extends in the counterclockwise direction toward the base end side. Therefore, as shown in FIG. 95 from FIG. 99, as a result of the needle tube 552 rotating counterclockwise when viewed from the base end side, the rear end side of the tissue fastening instrument 510A is smoothly let out to the outside of the needle tube 552, and reverts to the clockwise loop shape as shown in FIG. 99 without causing twisting or tangling. Furthermore, since the rotating mechanism 596 is set so that the needle tube 552 rotates approximately one revolution when the tissue fastening instrument 510A is pushed out by a length equivalent to approximately one turn of a loop from the distal end of the needle tube 552, when the needle tube 552 completes one revolution, one turn of the loop of the tissue fastening instrument 510A is reverted outside the needle tube 552. As a result, the rotation operation of the needle tube 552 and the placement operation of the tissue fastening instrument 510A are synchronized at a high level, and the placement becomes easier.

Figure 100:
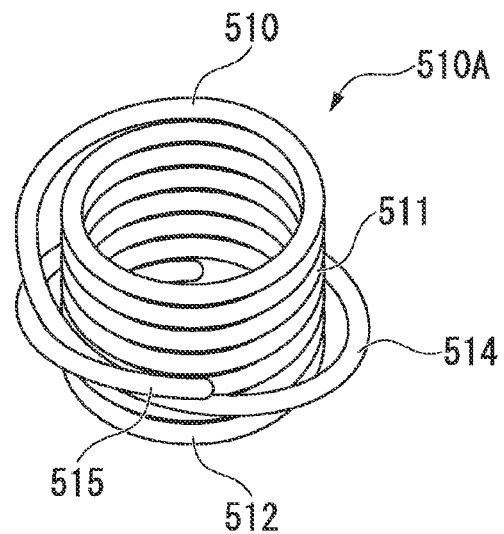
FIG. 100 is a drawing that shows the state of the end turn portion having run onto the peripheral spring.

After placement of the first tissue fixing portion 511 is completed, the spring portion 514 and the end turn portion 515 are let out to the outside of the needle tube 552 continuously. Also at this time, since the needle tube 552 is rotated in the counterclockwise direction as mentioned above when viewed from the base end, each part of the peripheral spring portion 513 is smoothly let out and reverts to the loop shape of prior to being accommodated in the needle tube 552. Since the loop diameter of the end turn portion 515 is larger than the loop diameter of the spring portion 514, as shown in FIG. 100, the end turn portion 515 runs onto the spring portion 514, and there is no reduction in the amount of pressing-down force of the intestinal wall Wd described below.

Figure 89:
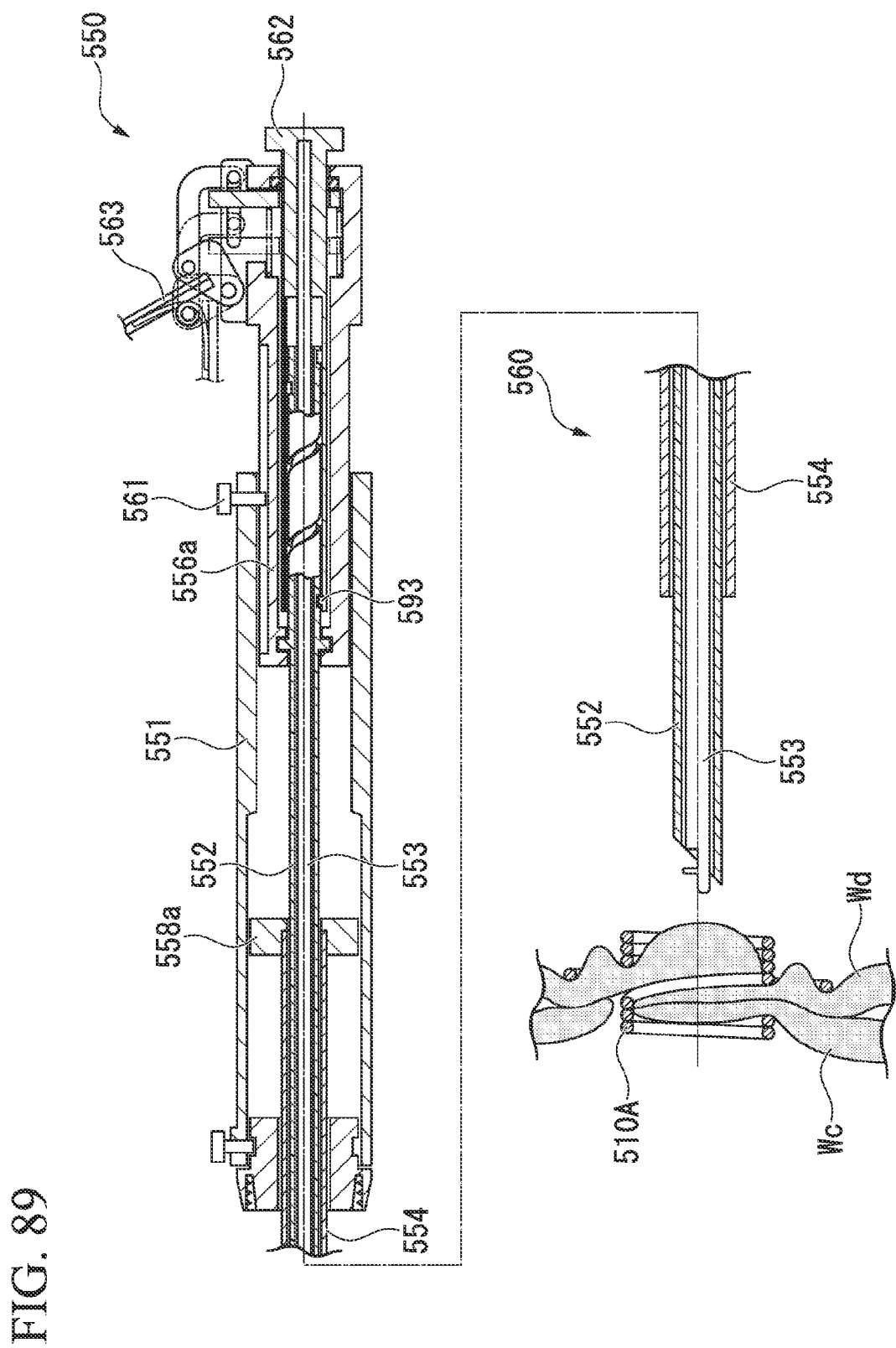
Figure 101:
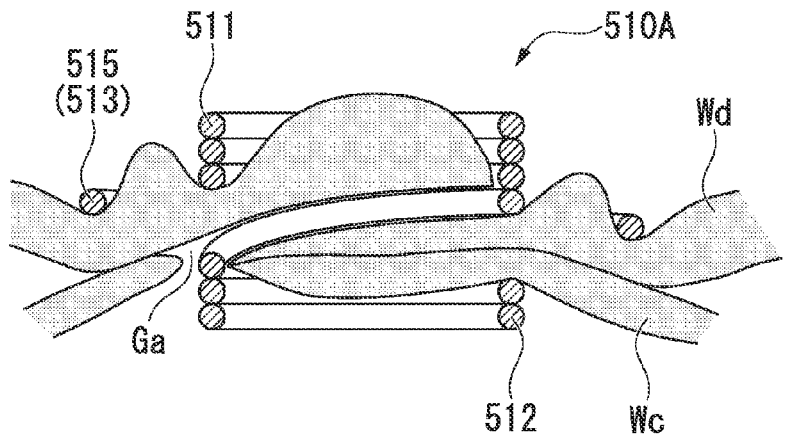
FIG. 101 is a drawing that shows the state of the same tissue fastening instrument placed in tissue.

When the entire tissue fastening instrument 510A is pushed out to the outside of the needle tube 552, the engagement of the through-hole 515B in the end portion 515A of the end turn portion 515 and the projection 553B of the stylet 553 will naturally be released, and the tissue fastening instrument 510A will be separated from the stylet 553. In this way as shown in FIG. 89 and FIG. 101, placement of the tissue fastening instrument 510A is completed. By placement of the tissue fastening instrument 510A, the first tissue fixing portion 511 and the second tissue fixing portion 512 fasten the intestinal wall Wd of the duodenum and the wall Wc of the common bile duct so as to be firmly attached, and the peripheral spring portion 513 presses the intestinal wall Wd to the side of the duct wall Wc.

Figure 102A:
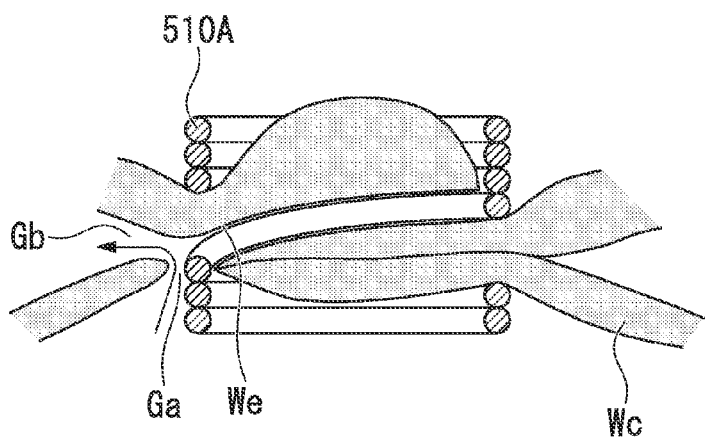
FIG. 102A is a drawing that describes the problem point when placing a tissue fastening instrument with no peripheral spring.
Figure 102B:
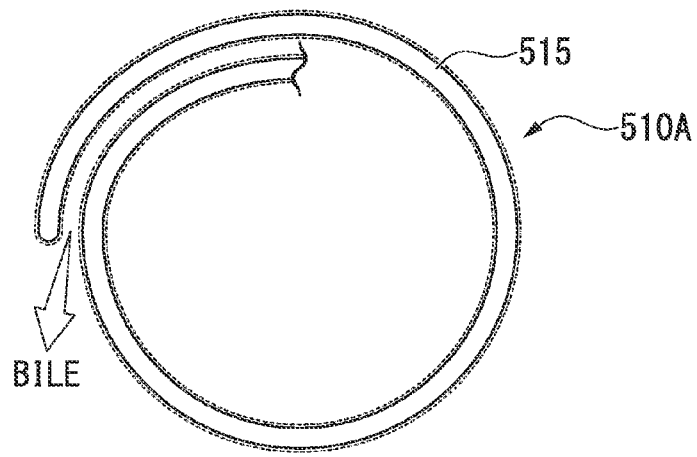
FIG. 102B is a drawing that describes the problem point when placing a tissue fastening instrument in which the shape of the same peripheral spring is not suitable.

When the tissue fastening instrument 510A is not provided with the peripheral spring portion 513, as shown in FIG. 102A, when punctured by the needle tube 552, a gap Ga is formed between a hole We that is formed in the wall Wc of the common bile duct and the metal wire 510 that is arranged to pass through the hole We, and a phenomenon occurs in which a bodily fluid such as bile or the like flows out through this gap Ga and leaks into the abdominal cavity through a gap Gb between the intestinal wall Wd of the duodenum and the wall We of the common bile duct. In the case of the bodily fluid being bile, there is the possibility of causing bile peritonitis. Also, even if the peripheral spring portion is present, when the end turn portion 515 that is firmly attached to the intestinal wall Wd does not form a closed loop, as shown in FIG. 102B, a gap arises in the intestinal wall Wd being pressed, and so there is a possibility of a leakage of a bodily fluid similarly occurring.

Figure 103A:
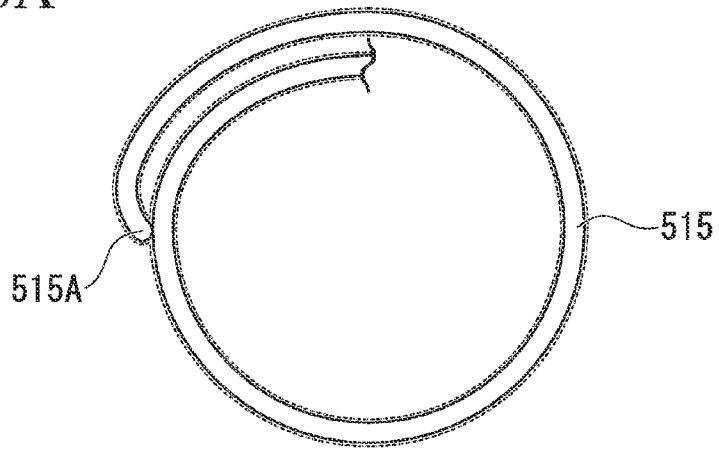
FIG. 103A and FIG. 103B are drawings that show the shape in a plan view of the end turn portion.

In the tissue fastening instrument 510A of the present embodiment, since the end portion 515A of the end turn portion 515 is in contact with a portion of the end turn portion 515 that has completed at least one rotation, as shown in FIG. 103A, a loop closed by the end turn portion 515 is formed. As a result, since the intestinal wall Wd on the outside of the base loop L1 is pressed in the shape of a closed ring, even if the tissue fastening instrument 510A is placed without generating the gap Gb, and bodily fluid such as bile does leak out through the gap Ga, this bodily fluid does not leak from the gap between the intestinal wall Wd of the duodenum and the wall We of the common bile duct into the abdominal cavity.

Figure 104A:
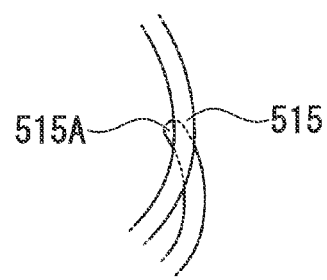
FIG. 104A and FIG. 104B are drawings that show other aspects of the same end turn portion.
Figure 104B:
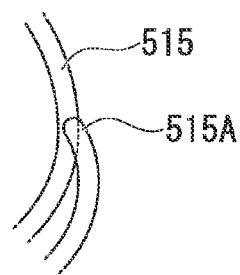
Figure 105:
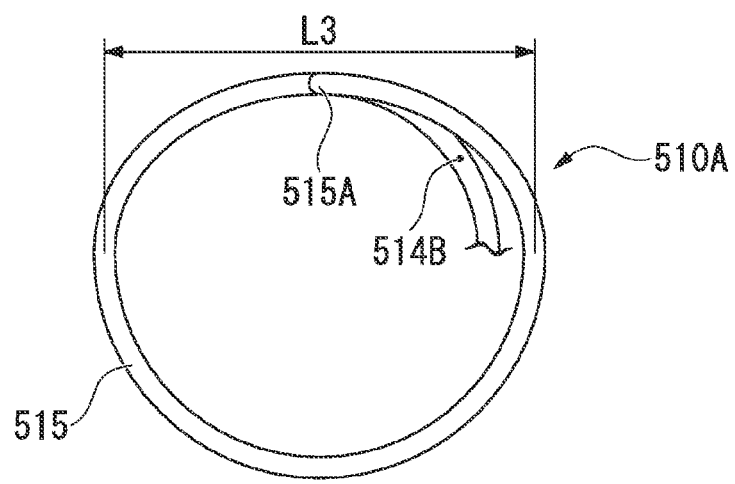
FIG. 105 is a drawing that shows another aspect of the same end turn portion.
Figure 106:
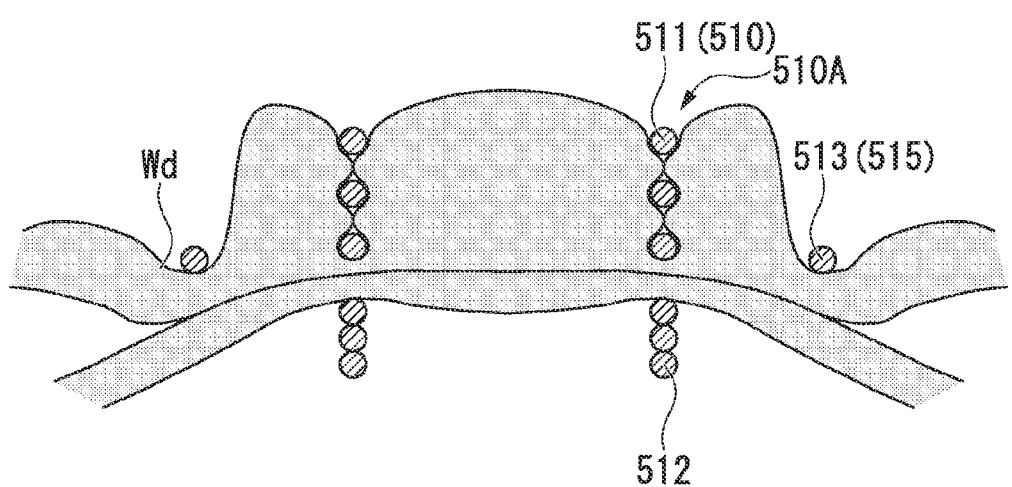
FIG. 106 is a drawing that show the state in which the fastening force of the tissue fastening instrument being insufficient.

Provided the end turn portion 515 forms a closed loop, there is no particular restriction on the aspect of connection between the end portion 515A and another section of the end turn portion 515. Therefore, as shown in FIG. 526A, the end portion 515A may tuck under another portion of the end turn portion 515, and as shown in FIG. 104B, the end portion 515A may run onto the top of another portion of the end turn portion 515. Furthermore, as shown in FIG. 105, the end portion 514B of the peripheral spring that serves as a boundary point of the spring portion 514 and the end turn portion 515 may be located inside the third loop L3 that the end turn portion 515 forms. Also, when the end turn portion 515 forms a loop of one or more turns, the section that extends from after the first turn may be completely superimposed on another end turn portion in the diameter direction of the third loop L3.

Figure 103B:
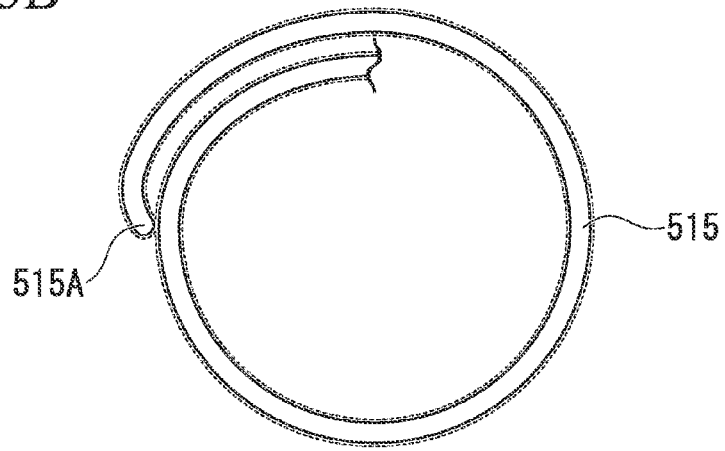

Note that the end portion 515A does not need to touch the end turn portion 515 with certainty, and provided the gap between the end portion 515A and another portion of the end turn portion 515 is small enough as shown in FIG. 103B, as the entire end turn portion 515, it can press down the intestinal wall Wd without a gap. Even in such a case, the end turn portion 515 can be said to substantially form the closed loop, and so there is no problem. Furthermore, the shape of the peripheral spring portion 513 may be set so as to form an essentially closed loop when the tissue fastening instrument 510A has been placed in tissue and the end turn portion 515 abuts the first biological tissue, with the end portion 515A and another portion of the turn portion 515 not making contact when the tissue fastening instrument 510A has not been placed.

After the tissue fastening instrument 510A has been placed, the operator recovers the needle tube 552 of the applicator 550 into the sheath 554, removes the applicator 550 and the endoscope 502 to outside of the body, and ends the procedure.

The intestinal wall Wd of the duodenum and the wall Wc of the common bile duct that are located in the base loop L1 are bound tight by the first tissue fixing portion 511 and the second tissue fixing portion 512, whereby the flow of blood is blocked, and in due time pressure necrosis is caused, Simultaneously, the intestinal wall Wd and the duct wall Wc carry out adhesion bonding around the base loop L1.

The necrosed tissue and the tissue fastening instrument 510A drop out of the placement position. Since the first tissue fixing portion 511 and the second tissue fixing portion 512 are always biased by the peripheral spring portion 513 to the side of the cavity of the duodenum, when the tissue fastening instrument 510A drops from the other tissue, it always drops to the side of the cavity in the duodenum, and the tissue fastening instrument 510A is quickly excreted out of the body through the small intestine and the large intestine. Since the end portion 515A of the end turn portion 515 which was engaged with the stylet 553 extends to another portion of the end turn portion 515, there is no damage to other tissue in the body during the excretion process.

Although the peripheral spring portion 513 presses the intestinal wall Wd of the duodenum onto the duct wall Wc side of the common bile duct, the reaction force at this time acts as a force that pulls the first tissue fixing portion 511 away from the intestinal wall Wd. Therefore, when the initial tension of the first tissue fixing portion 511 is less than the biasing force of the peripheral spring portion 513, as shown in FIG. 103, the fastening force between the first tissue fixing portion 511 and the second tissue fixing portion 512 weakens, and gaps form between the metal wire 510 of the first tissue fixing portion 511.

In this way, if the force that binds the intestinal wall Wd and the duct wall Wc becomes weak, the flow of the blood between the intestinal wall Wd and the duct wall Wc cannot be sufficiently blocked. Moreover if gaps appear between the metal wire 510 that constitutes the first tissue fixing portion 511, flow of blood will occur between the tissue in the base loop L1 and the tissue outside thereof. For that reason, the tissue in the base loop L1 will not necrose. Accordingly, the tissue fastening instrument 510A will not drop and so it will subsequently also not be possible to form a fistula.

In the tissue fastening instrument 510A of the present embodiment, the initial tension of the first tissue fixing portion 511 is set to such an extent that, in the event of the tissue fastening instrument 510A of present embodiment being placed in the body, in the case of receiving the reaction force when the distal end of the peripheral spring portion 513 has pressed down the intestinal wall Wd, the first tissue fixing portion 511 is not pulled away from the intestinal wall Wd as shown in FIG. 101, and gaps do not form between the metal wire 510. As a result, at the time of placement, it is possible to maintain the joined state without gaps appearing between the metal wire 510 of the first tissue fixing portion 511. Therefore, the flow of blood to the tissue in the base loop L1 is favorably blocked, and the tissue concerned reliably necroses. Thereafter, the tissue fastening instrument 510A and the necrosed tissue fall out, and a fistula that connects the intestinal wall Wd of the duodenum and the duct wall Wc of the common bile duct is formed.

According to the tissue fastening instrument 510A of the present embodiment, the first tissue fixing portion 511 and the second tissue fixing portion 512 favorably fasten the first biological tissue and the second biological tissue, and necrose a portion of both while bonding another portion of both, and so it is possible to readily form a fistula that brings the first biological tissue and the second biological tissue into communication.

Moreover, in the peripheral spring portion 513, the second loop L2 that the spring portion 514 forms is larger than the base loop L1 that the first tissue fixing portion 511 and the second tissue fixing portion 512 form, and the third loop L3 that the end turn portion 515 forms is set to be larger than the second loop L2, and these loops are set so as not to mutually overlap in the diameter direction of the base loop L1.

Therefore, it is possible to safely use in a manner such that each section reliably exhibits the respective predetermined fastening force or biasing force without twisting or tangling of the metal wires in the loops occurring.

Furthermore, since the end portion 515A of the end turn portion 515 extends toward another part of the end turn portion 515, the end turn portion 515 forms a closed loop, and in addition to suitably preventing leakage of a bodily fluid as mentioned above, the end portion 515A is not exposed, and injury to other tissue is hindered in the process of the tissue fastening instrument 510A being discharged to outside of the body.

Moreover, according to the applicator 550 of the present embodiment, in the state of the tissue fastening instrument 510A being accommodated in the needle tube 552, since the tissue fastening instrument 510A and the stylet 553 are engaged, forward/backward movement and rotation of the stylet 553 are suitably transmitted to the tissue fastening instrument 510A as mentioned above.

When the stylet 553 and the tissue fastening instrument 510A are not engaged, due to the restoring force of the tissue fastening instrument 510A trying to return to its original form outside the needle tube 552, it may deviate to outside of the needle tube 552 to a region not intended, and so the tissue fastening instrument 510A may not return to its shape of before accommodation. If the stylet 553 and the tissue fastening instrument 510A are connected, such unintended deviation of the tissue fastening instrument 510A is suppressed, and the tissue fastening instrument 510A reliably reverts to the shape of prior to being accommodated and is placed.

Moreover, when the tissue fastening instrument 510A and the stylet 553 can be engaged, by retracting the stylet 553 in the needle tube 552 while causing it to rotate, it is possible to readily accommodate the tissue fastening instrument 510A in the needle tube 552.

Furthermore, as for the tissue fastening instrument 510A and the stylet 553, since the engagement is naturally released outside of the needle tube 552, it is possible to carry out placement of the tissue fastening instrument 510A without requiring the operator to perform a special operation for releasing the engagement.

Figure 107A:
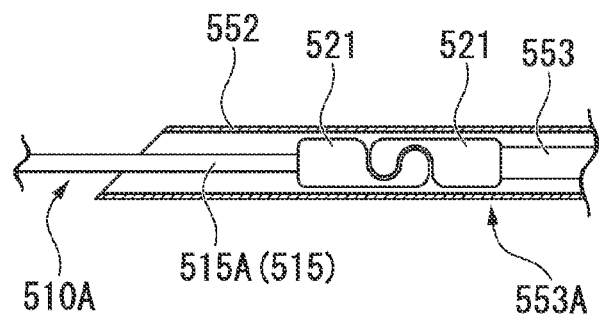
FIG. 107A and FIG. 107B are drawings that show the joining aspect of the tissue fastening instrument and the stylet in accordance with a modification of the present invention.
Figure 107B:
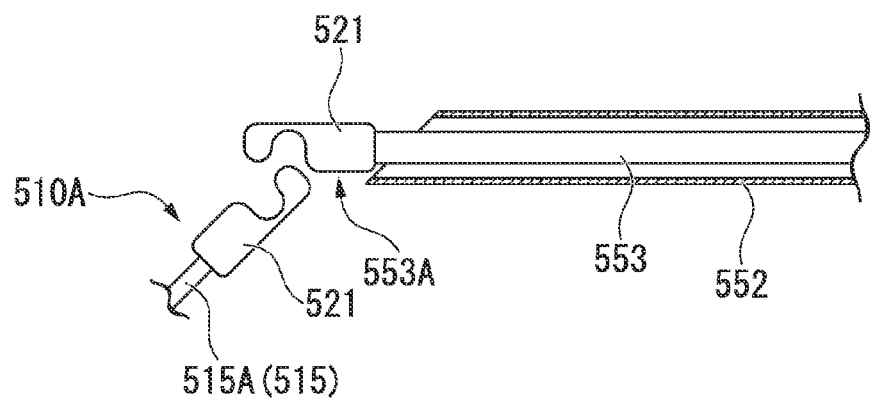

The joining aspect of the tissue fastening instrument 510A and the stylet 553 is not limited to that mentioned above, and various aspects may be adopted. For example, as shown by the modification in FIGS. 107A and 107B, hooks 521 that are mutually engagable are provided at the distal end 553A of the stylet 553 and the end portion 515A of the end turn portion 515 of the tissue fastening instrument 510A, and both may be detachably connected in the needle tube 552. In providing the hooks 521, grinding or the like may be performed on the distal end 553A and the end portion 515A, or a member is shaped like the hook 521 may be attached to the distal end 553A and the end portion 515A by caulking or welding and the like. Moreover, in the above-mentioned modification, although the example was described of the distal end 553A and the end portion 515A having the identical hooks 521, as long as engagement/disengagement is possible, hooks of different shapes may be respectively attached. However, if identical hooks are used, by reducing the number of parts, it is possible to raise manufacturing efficiency.

Figure 108A:
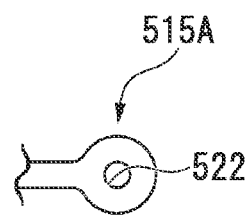
FIG. 108A and FIG. 108B are drawings that show end portions of the tissue fastening instrument in accordance with modifications of the present invention.
Figure 108B:
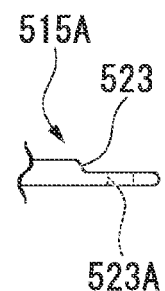
Figure 109:
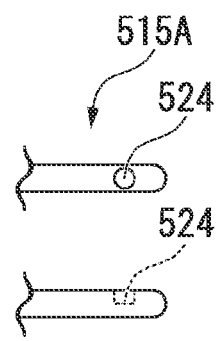
FIG. 109 is a drawing that shows the end portion of the tissue fastening instrument in accordance a modification of the present embodiment.

Moreover, when providing a through-hole in the end portion 515A, in the manner of the modification shown in FIG. 108A, the end portion 515A may be lengthened, and a through-hole 522 may be formed, and in the manner of the modification shown in FIG. 108B, a step portion 523 may be formed by grinding or the like, and a through-hole 523A may be formed in the step portion 523. Furthermore, in the manner of the modification shown in FIG. 109, a bottomed concavity 524 may be provided in place of a through-hole.

Figure 110A:
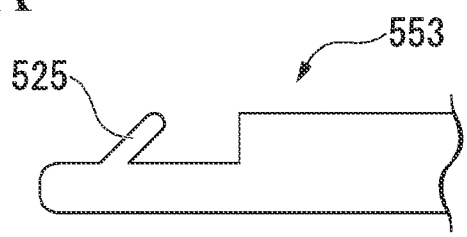
FIG. 110A and FIG. 110B are drawings that show another example of a joining aspect of the same tissue fastening instrument and the same stylet.
Figure 110B:
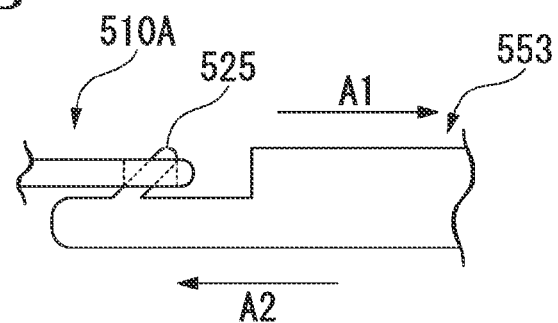
Figure 111:
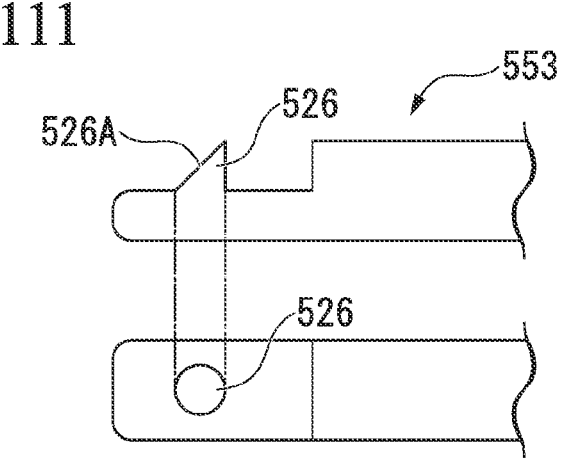
FIG. 111 is a drawing that shows the end portion of the stylet in accordance with a modification of the present embodiment.

Moreover, the distal end of a projection that is provided on the stylet 553 may be formed sloping to the base end side in the manner of a projection 525 shown in FIG. 110A. By doing so, when moving the stylet 553 in the direction of arrow A1 shown in FIG. 110B, since the engagement with the tissue fastening instrument 510A is hindered from separating, it is easy to accommodate the tissue fastening instrument 510A in the needle tube 552 at the time of manufacture etc. When moving the stylet 553 in the direction of arrow A2, the engagement of both is easily separated, and smooth operation during placement is possible. In this case as sell, by suitably setting the dimensions of the stylet 553 and the tissue fastening instrument 510A with respect to the needle tube 552, it is possible to suitably prevent the engagement from coming apart in the needle tube 552 by reducing the movable width in the cross-sectional direction of the stylet 553 and the tissue fastening instrument 510A in the needle tube 552. The above-mentioned effect can be similarly obtained even in the case of forming at the base end side a projection 526 so as to have a slope 526A that forms an acute angle with the axial line of the stylet 553 as in the modification shown in FIG. 111.

Figure 112:
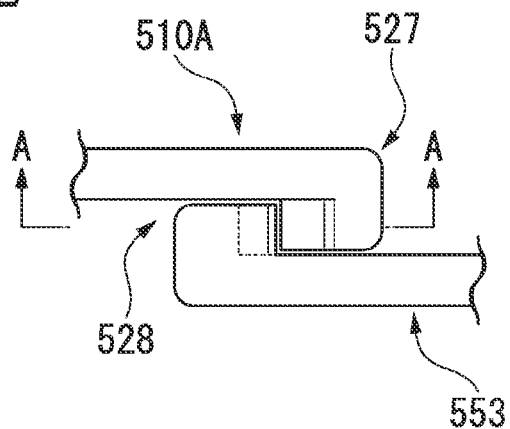
FIG. 112 to FIG. 114 are drawings that show another example of a joining aspect of the same tissue fastening instrument and the same stylet.
Figure 113:
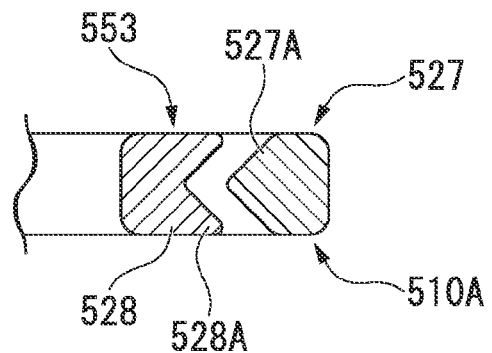
Figure 114:
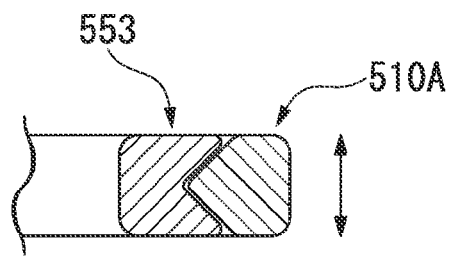
Figure 115:
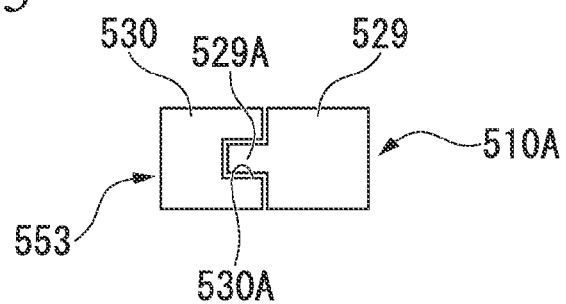
FIG. 115 is a drawing that shows another example of a joining aspect of the same tissue fastening instrument and the same stylet.

Furthermore, in the manner of the modification shown in FIG. 112 and FIG. 113 (a sectional view along line A-A of FIG. 113), an engaging portion 527 and an engaged portion 528 may be formed so as to respectively have restriction portions 527A and 528A that enable engagement/disengagement of the tissue fastening instrument 510A and the stylet 553 and restrict their relative movement in the width direction. By doing so, as shown in FIG. 114, since movement of the tissue fastening instrument 510A and the stylet 553 in the width direction (the direction shown by the arrows in FIG. 114) is restricted, it is easy to accommodate the tissue fastening instrument 510A in the needle tube 552 while engaged with the stylet 553 during manufacturing. The shapes of the restriction portions are not particularly limited provided they are capable of restricting movement of the tissue fastening instrument 510A and the stylet 553 in the width direction. For example, an engaging portion 529 and an engaged portion 530 that have as restriction portions a convex portion 529A and a concave portion 530A, respectively, as shown in FIG. 115 may be provided in the tissue fastening instrument 510A and the stylet 553, respectively.

Figure 116A:
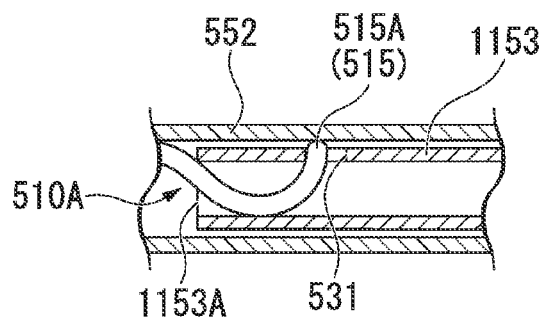
FIGS. 116A and 116B are drawings that show another example of a joining aspect of the same tissue fastening instrument and the same stylet.
Figure 116B:
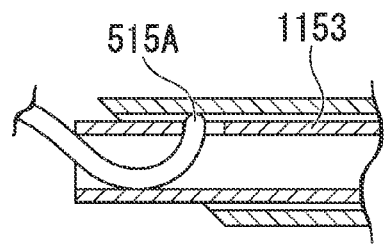
Figure 117A:
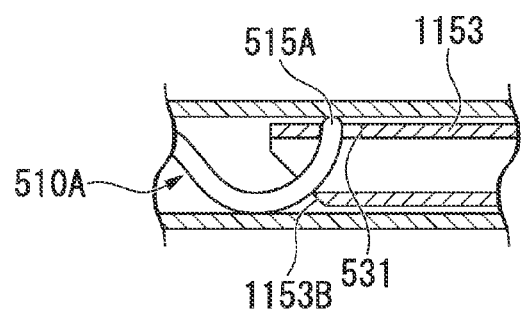
FIG. 117A and FIG. 117B are drawings that show another example of a joining aspect of the same tissue fastening instrument and the same stylet.
Figure 117B:
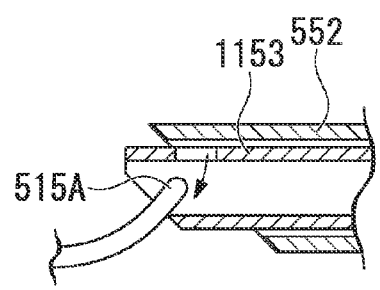

Furthermore, as shown in FIG. 116A, a region of a fixed length on the distal end side of at least a stylet 1153 may be formed in a hollow shape that has an inner cavity, and a through-hole 531 may be formed on the outer periphery surface, and by causing the end portion 515A of the end turn portion 515 of the tissue fastening instrument 510A to enter the inner cavity and project from the through-hole 531, the stylet 1153 and the tissue fastening instrument 510A may be engaged. However, in this case, when an opening end face 1153A at the distal end of the stylet 1153 is shaped so as to be perpendicular to the axial line of the stylet 1153, as shown in FIG. 116B, the peripheral surface of the end portion 515A may catch on the inner surface of the stylet 1153, and the engagement may be hindered from release outside of the needle tube 552. For this reason, as shown in FIG. 117A, it is good to set the shape of an opening end face 1153B so that the length of the stylet 1153 is shortest at the position facing the through-hole 531, sandwiching the axial line of the stylet 1153. When doing so, as shown in FIG. 117B, during the release of the engagement, it is preferred to hinder the peripheral surface of the end portion 515A from abutting the inner surface of the stylet 1153 in order to facilitate release of the engagement outside of the needle tube 552.

Note that in the modification shown from FIG. 116A to FIG. 117B, the end portion 515A of the end turn portion 515 of the tissue fastening instrument 510A may be bent so as to facilitate engagement in the through-hole 531.

Figure 118A:
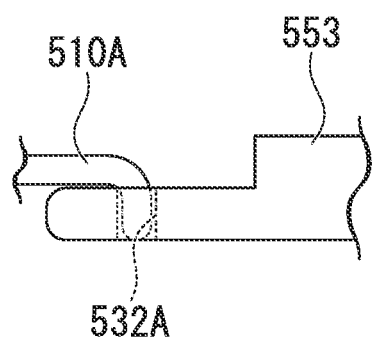
FIG. 118A and FIG. 118B are drawings that show another example of a joining aspect of the same tissue fastening instrument and the same stylet.
Figure 118B:
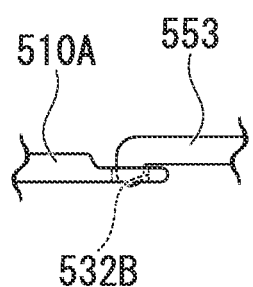

Also, instead of providing a projection on one of the tissue fastening instrument 510A or the stylet 553, the end portion of one may be bent and engaged in a through-hole 532A or 532B that is provided in the end portion of the other and has a larger diameter than the wire diameter of the other shown in FIG. 118A and FIG. 118B. In this case, in order to enable entry of the end portion of one, a through-hole with a diameter that is comparatively larger is required, so it is good to provide the though-hole 522 or the like by the method shown in FIG. 108A in the tissue fastening instrument 510A or the stylet 553.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of operating a needle tube provided with a tissue fastening instrument to form a through hole that communicates a first hollow organ tissue and a second hollow organ tissue adjacent to the first hollow organ tissue, wherein the tissue fastening instrument comprises a first tissue fixing portion, a second tissue fixing portion, and an end turn portion, provided in that order, wherein the tissue fastening instrument is configured to be held within the needle tube in an extended state, and to revert to a coiled state from the extended state upon discharge from within the needle tube, wherein in the coiled state, the first tissue fixing portion is configured to be wound in a first coil shape, the second tissue fixing portion is configured to be wound in a second coil shape, and the end turn portion is configured to be wound in a loop shape, wherein a diameter of the loop shape is larger than a diameter of the second coil shape, and wherein the method comprises:
 operating the needle tube holding the tissue fastening instrument in the extended state to puncture the first hollow organ tissue from an inside of the first hollow organ tissue to an outside of the first hollow organ tissue, and then to puncture the second hollow organ tissue from an outside of the second hollow organ tissue to an inside of the second hollow organ tissue;

operating the needle tube to discharge the first tissue fixing portion from within the needle tube to the inside of the second hollow organ tissue, such that the first tissue fixing portion reverts to the coiled state to be wound in the first coil shape and to engage the second hollow organ tissue;

operating the needle tube to discharge the second tissue fixing portion from within the needle tube to the inside of the first hollow organ tissue, such that the second tissue fixing portion reverts to the coiled state to be wound in the second coil shape and to engage a first part of the first hollow organ tissue such that the first hollow organ tissue and the second hollow organ tissue are fastened between the first tissue fixing portion and the second tissue fixing portion; and operating the needle tube to discharge the end turn portion from within the needle tube to the inside of the first hollow organ tissue, such that the end turn portion reverts to the coiled state to be wound in the loop shape and to engage a second part of the first hollow organ tissue that surrounds the first part of the first hollow organ tissue engaged by the second coil shape of the second tissue fixing portion, wherein the tissue fastening instrument further comprises a spring portion provided between the second tissue fixing portion and the end turn portion, wherein in the coiled state of the tissue fastening instrument, the spring portion is configured to be outside of an outer periphery of the second coil shape of the second tissue fixing portion, and wherein the method further comprises operating the needle tube to discharge the spring portion from within the needle tube to the inside of the first hollow organ tissue, such that the spring portion reverts to the coiled state.

2. The method according to claim 1, further comprising:
causing necrosis of a portion of the first hollow organ tissue and a portion of the second hollow organ tissue fastened together by the first tissue fixing portion and the second tissue fixing portion.

3. The method according to claim 1,
wherein at least an end part of the end turn portion is disposed in a biased direction from an outer periphery of the end turn portion to an outer periphery of the first tissue fixing portion.

4. The method according to claim 1,
wherein in the coiled state of the tissue fastening instrument, the spring portion is configured to be wound in a helical shape outside an outer periphery of the first coil shape of the first tissue fixing portion and the outer periphery of the second coil shape of the second tissue fixing portion, and wherein the needle tube is operated to discharge the spring portion from within the needle tube to the inside of the first hollow organ tissue, such that the spring portion reverts to the coiled state and a force of the helical shape of the spring portion acts in a direction perpendicular to an axial line of the first coil shape.

5. The method according to claim 1,
wherein an end part of the end turn portion reverted to the coiled state is positioned within the inside of the first hollow organ tissue and presses the second part of the first hollow organ tissue that surrounds the first part of the first hollow organ tissue.

6. A method of operating a needle tube provided with a tissue fastening instrument to form a through hole that communicates a first hollow organ tissue and a second hollow organ tissue adjacent to the first hollow organ tissue, wherein the tissue fastening instrument comprises a first tissue fixing portion, a second tissue fixing portion, and an end turn portion, provided in that order, wherein the tissue fastening instrument is configured to be held within the needle tube in an extended state, and to revert to a coiled state from the extended state upon discharge from within the needle tube, wherein in the coiled state, the first tissue fixing portion is configured to be wound in a first coil shape, the second tissue fixing portion is configured to be wound in a second coil shape, and the end turn portion is configured to be wound in a loop shape, wherein a diameter of the loop shape is larger than a diameter of the second coil shape, and wherein the method comprises:
operating the needle tube holding the tissue fastening instrument in the extended state to puncture the first hollow organ tissue from an inside of the first hollow organ tissue to an outside of the first hollow organ tissue, and then to puncture the second hollow organ tissue from an outside of the second hollow organ tissue to an inside of the second hollow organ tissue;

operating the needle tube to discharge the first tissue fixing portion from within the needle tube to the inside of the second hollow organ tissue, such that the first tissue fixing portion reverts to the coiled state to be wound in the first coil shape and to engage the second hollow organ tissue;

operating the needle tube to discharge the second tissue fixing portion from within the needle tube to the inside of the first hollow organ tissue, such that the second tissue fixing portion reverts to the coiled state to be wound in the second coil shape and to engage a first part of the first hollow organ tissue such that the first hollow organ tissue and the second hollow organ tissue are fastened between the first tissue fixing portion and the second tissue fixing portion; and operating the needle tube to discharge the end turn portion from within the needle tube to the inside of the first hollow organ tissue, such that the end turn portion reverts to the coiled state to be wound in the loop shape and to engage a second part of the first hollow organ tissue that surrounds the first part of the first hollow organ tissue engaged by the second coil shape of the second tissue fixing portion, wherein the needle tube is operated to discharge the end turn portion from within the needle tube to the inside of the first hollow organ tissue, such that the end turn portion reverts to the coiled state to be wound in the loop shape that is a closed loop shape outside of the second coil shape of the second tissue fixing portion, and wherein the closed loop shape of the end turn portion presses the first hollow organ tissue.

7. The method according to claim 6, wherein the needle tube is operated to discharge the end turn portion from within the needle tube to the inside of the first hollow organ tissue, such that the end turn portion reverts to the coiled state to press the second part of the first hollow organ tissue forward towards the second hollow organ tissue to seal a gap formed between the first hollow organ tissue and the second hollow organ tissue on a periphery of the second coil shape of the second tissue fixing portion.

8. The method according to claim 6, wherein when the needle tube is operated to discharge the end turn portion from within the needle tube to the inside of the first hollow organ tissue, the end turn portion reverts to the coiled state to press the second part of the first hollow organ tissue forward towards the second hollow organ tissue to seal a gap formed between the first hollow organ tissue and the second hollow organ tissue on a periphery of the second coil shape of the second tissue fixing portion.

9. The method according to claim 6, wherein the tissue fastening instrument further comprises a spring portion provided between the second tissue fixing portion and the end turn portion, wherein in the coiled state of the tissue fastening instrument, the spring portion is configured to be outside of an outer periphery of the second coil shape of the second tissue fixing portion, and wherein the method further comprises operating the needle tube to discharge the spring portion from within the needle tube to the inside of the first hollow organ tissue, such that the spring portion reverts to the coiled state.

10. The method according to claim 6, wherein in the coiled state of the tissue fastening instrument, at least an end part of the end turn portion is disposed in a biased direction from an outer periphery of the end turn portion to an outer periphery of the first tissue fixing portion.

11. A method of operating a needle tube provided with a tissue fastening instrument to form a through hole that communicates a first hollow organ tissue and a second hollow organ tissue adjacent to the first hollow organ tissue, wherein the tissue fastening instrument comprises a first tissue fixing portion, a second tissue fixing portion, and an end turn portion, provided in that order, wherein the tissue fastening instrument is configured to be held within the needle tube in an extended state, and to revert to a coiled state from the extended state upon discharge from within the needle tube, wherein in the coiled state, the first tissue fixing portion is configured to be wound in a first coil shape, the second tissue fixing portion is configured to be wound in a second coil shape, and the end turn portion is configured to be wound in a loop shape, wherein a diameter of the loop shape is larger than a diameter of the second coil shape, wherein the method comprises:

operating the needle tube holding the tissue fastening instrument in the extended state to puncture the first hollow organ tissue from an inside of the first hollow organ tissue to an outside of the first hollow organ tissue, and then to puncture the second hollow organ tissue from an outside of the second hollow organ tissue to an inside of the second hollow organ tissue;

operating the needle tube to discharge the first tissue fixing portion from within the needle tube to the inside of the second hollow organ tissue, such that the first tissue fixing portion eve s to the coiled state to be wound in the first coil shape and to engage the second hollow organ tissue;

operating the needle tube to discharge the second tissue fixing portion from within the needle tube to the inside of the first hollow organ tissue, such that the second tissue fixing portion reverts to the coiled state to be wound in the second coil shape and to engage a first part of the first hollow organ tissue such that the first hollow organ tissue and the second hollow organ tissue are fastened between the first tissue fixing portion and the second tissue fixing portion;

operating the needle tube to discharge the end turn portion from within the needle tube to the inside of the first hollow organ tissue, such that the end turn portion reverts to the coiled state to be wound in the loop shape and to engage a second part of the first hollow organ tissue that surrounds the first part of the first hollow organ tissue engaged by the second coil shape of the second tissue fixing portion; and causing necrosis of a portion of the first hollow organ tissue and a portion of the second hollow organ tissue fastened together by the first tissue fixing portion and the second tissue fixing portion, wherein the first hollow organ tissue is an intestinal wall of a duodenum, wherein the second hollow organ tissue is a wall of a common bile duct, and wherein the method further comprises causing a necrosed portion of the intestinal wall of the duodenum, a necrosed portion of the common bile duct, and the tissue fastening instrument to fall to an inside of the intestinal wall of the duodenum.

12. The method according to claim 11, wherein the needle tube is operated to discharge the end turn portion from within the needle tube to the inside of the first hollow organ tissue, such that the end turn portion reverts to the coiled state to press the second part of the first hollow organ tissue forward towards the second hollow organ tissue to seal a gap formed between the first hollow organ tissue and the second hollow organ tissue on a periphery of the second coil shape of the second tissue fixing portion.

13. The method according to claim 11, wherein the tissue fastening instrument further comprises a spring portion provided between the second tissue fixing portion and the end turn portion, wherein in the coiled state of the tissue fastening instrument, the spring portion is configured to be outside of an outer periphery of the second coil shape of the second tissue fixing portion, and wherein the method further comprises operating the needle tube to discharge the spring portion from within the needle tube to the inside of the first hollow organ tissue, such that the spring portion reverts to the coiled state.

14. The method according to claim 13, wherein at least an end part of the end turn portion is disposed in a biased direction from an outer periphery of the end turn portion to an outer periphery of the first tissue fixing portion.

15. The method according to claim 11, further comprising:

moving an opening of the needle tube from which the tissue fastening instrument is discharged from the inside of the second hollow organ tissue to the inside of the first hollow organ tissue, after discharging the first tissue fixing portion to the inside of the second hollow organ tissue and before discharging the second tissue fixing portion to the inside of the first hollow organ tissue.

* * * * *